(12) United States Patent
Millis et al.

(10) Patent No.: US 11,793,544 B2
(45) Date of Patent: Oct. 24, 2023

(54) MEASURING DEVICE

(71) Applicant: Fidmi Medical Ltd., Caesarea (IL)

(72) Inventors: Shahar Millis, Pardes Hanna-Karkur (IL); Ishay Benuri-Silbiger, Jerusalem (IL)

(73) Assignee: Fidmi Medical Ltd., Caesarea (IL)

( * ) Notice: Subject to any disclaimer, the term of this patent is extended or adjusted under 35 U.S.C. 154(b) by 424 days.

(21) Appl. No.: 16/920,780

(22) Filed: Jul. 6, 2020

(65) Prior Publication Data

US 2020/0330125 A1 Oct. 22, 2020

Related U.S. Application Data

(63) Continuation of application No. 16/065,807, filed as application No. PCT/IL2016/051377 on Dec. 23, 2016, now Pat. No. 10,702,304.

(Continued)

(51) Int. Cl.
*A61B 90/00* (2016.01)
*A61B 17/34* (2006.01)
*A61J 15/00* (2006.01)

(52) U.S. Cl.
CPC .......... *A61B 17/3415* (2013.01); *A61B 90/06* (2016.02); *A61J 15/0015* (2013.01);
(Continued)

(58) Field of Classification Search
CPC ................ A61B 17/3415; A61B 90/06; A61B 2017/3484; A61B 2017/3488;
(Continued)

(56) References Cited

U.S. PATENT DOCUMENTS 3,834,394 A 9/1974 Hunter et al.
4,471,779 A 9/1984 Antoshkiw et al.
(Continued)

FOREIGN PATENT DOCUMENTS

CN 1780599 5/2006
CN 101905058 12/2010
(Continued)

OTHER PUBLICATIONS

Notice of Reason(s) for Rejection dated Jan. 29, 2021 From the Japan Patent Office Re. Application No. 2018-552933 and Its Translation Into English. (7 Pages).
(Continued)

*Primary Examiner* — Amber R Stiles

(57) ABSTRACT

In some embodiments a PEG feeding device includes a tube sized to bridge a channel between a stomach and an outer abdominal surface; an internal bolster, and an external bolster. Optionally the bolsters are connected to the tube. The internal bolster may be sized to resist movement out of the stomach through the stoma. The external bolster may be sized to resist movement into the stoma from the outer abdominal surface. The external bolster may include an underside which extends from the tube in a radial direction between the external bolster and the outer abdominal surface. The underside of the outer bolster may contact the outer abdominal surface at a distance from an external opening of the stoma. Optionally the distance between the internal bolster and the external bolster is adjustable. Optionally an angle between one or both of the bolsters and the tube is adjustable.

18 Claims, 55 Drawing Sheets

Related U.S. Application Data

(60) Provisional application No. 62/356,482, filed on Jun. 29, 2016.

(52) U.S. Cl.
CPC ....... *A61J 15/0038* (2013.01); *A61J 15/0057* (2013.01); *A61J 15/0065* (2013.01); *A61J 15/0092* (2013.01); *A61B 2017/3484* (2013.01); *A61B 2017/3488* (2013.01); *A61B 2017/3492* (2013.01); *A61B 2090/062* (2016.02); *A61B 2090/3937* (2016.02); *A61J 15/0019* (2013.01); *A61J 15/0076* (2015.05); *A61J 15/0096* (2013.01)

(58) Field of Classification Search
CPC ...... A61B 2017/3492; A61B 2090/062; A61B 2090/3937; A61J 15/0015; A61J 15/0038; A61J 15/0057; A61J 15/0065; A61J 15/0092; A61J 15/0019; A61J 15/0076; A61J 15/0096; A61J 15/0042; A61J 15/0061; A61M 25/06; A61M 2025/0008; A61M 2039/0255
See application file for complete search history.

(56) References Cited

U.S. PATENT DOCUMENTS

| | | | |
|---|---|---|---|
| 4,710,169 | A | 12/1987 | Christopher |
| 4,944,732 | A | 7/1990 | Russo |
| 5,073,166 | A | 12/1991 | Parks et al. |
| 5,356,382 | A | 10/1994 | Picha et al. |
| 5,356,391 | A | 10/1994 | Stewart |
| 5,391,159 | A | 2/1995 | Hirsch et al. |
| 5,556,385 | A | 9/1996 | Andersen |
| 5,716,347 | A | 2/1998 | Gibbs et al. |
| 5,797,939 | A | 8/1998 | Yoon |
| 6,039,714 | A | 3/2000 | Cracauer et al. |
| 6,045,536 | A | 4/2000 | Meier et al. |
| 6,186,985 | B1 | 2/2001 | Snow |
| 6,485,476 | B1 | 11/2002 | von Dyck et al. |
| 6,666,853 | B2 | 12/2003 | Chu et al. |
| 6,976,980 | B2 | 12/2005 | Brenner et al. |
| 7,582,072 | B2 | 9/2009 | McMichael |
| 7,637,915 | B2 | 12/2009 | Parmer et al. |
| 8,475,430 | B2 | 7/2013 | Adams et al. |
| 8,480,652 | B2 | 7/2013 | Renaux et al. |
| 8,834,370 | B2 | 9/2014 | Evert et al. |
| 10,426,708 | B2 | 10/2019 | Millis et al. |
| 2002/0198440 | A1 | 12/2002 | Snow |
| 2003/0163119 | A1 | 8/2003 | Chu et al. |
| 2003/0225376 | A1 | 12/2003 | Fournie et al. |
| 2004/0059293 | A1 | 3/2004 | Chu et al. |
| 2004/0092973 | A1 | 5/2004 | Chanduszko et al. |
| 2005/0033240 | A1 | 2/2005 | Oishi et al. |
| 2005/0059929 | A1 | 3/2005 | Bolmsjo et al. |
| 2006/0052752 | A1 | 3/2006 | McMichael |
| 2006/0116658 | A1 | 6/2006 | McMichael et al. |
| 2006/0206095 | A1 | 9/2006 | Chu et al. |
| 2007/0156117 | A1 | 7/2007 | Adams et al. |
| 2008/0091146 | A1 | 4/2008 | Solovay et al. |
| 2010/0022969 | A1 | 1/2010 | Renaux |
| 2010/0113880 | A1 | 5/2010 | Page |
| 2010/0185155 | A1 | 7/2010 | McMichael et al. |
| 2010/0312192 | A1 | 12/2010 | Fitzgerald et al. |
| 2011/0009828 | A1 | 1/2011 | Prechtel et al. |
| 2011/0082442 | A1 | 4/2011 | Solovay et al. |
| 2011/0144623 | A1 | 6/2011 | Renaux et al. |
| 2011/0288534 | A1 | 11/2011 | Aguirre et al. |
| 2011/0313359 | A1 | 12/2011 | Cohen |
| 2012/0010571 | A1 | 1/2012 | Adams et al. |
| 2012/0116303 | A1* | 5/2012 | Marx ................ A61B 17/3415 604/167.03 |
| 2012/0221032 | A1 | 8/2012 | Duperier et al. |
| 2012/0277541 | A1 | 11/2012 | Bhargava et al. |
| 2013/0165862 | A1 | 1/2013 | Griffith et al. |
| 2013/0158401 | A1 | 6/2013 | Evert et al. |
| 2014/0121658 | A1 | 5/2014 | Cosman, Jr. et al. |
| 2014/0276628 | A1 | 9/2014 | Gandras et al. |
| 2014/0330254 | A1 | 11/2014 | Rosenberger et al. |
| 2015/0038794 | A1 | 2/2015 | Pattison et al. |
| 2016/0143816 | A1 | 5/2016 | Benuri-Silbiger |
| 2017/0367932 | A1 | 12/2017 | Millis et al. |
| 2019/0021762 | A1 | 1/2019 | Millis et al. |
| 2020/0345393 | A1 | 11/2020 | Millis et al. |

FOREIGN PATENT DOCUMENTS

| | | |
|---|---|---|
| EP | 0824929 | 2/1998 |
| GB | 2243299 | 10/1991 |
| JP | 2015-535436 | 12/2015 |
| WO | WO 2010/075032 | 7/2010 |
| WO | WO 2010/115102 | 10/2010 |
| WO | WO 2014/104402 | 7/2014 |
| WO | WO 2014/203259 | 12/2014 |
| WO | WO 2016/103268 | 6/2016 |
| WO | WO 2017/109788 | 6/2017 |

OTHER PUBLICATIONS

Notice of Reason for Rejection dated Jul. 8, 2022 From the Japan Patent Office Re. Application No. 2018-552933 and Its Translation Into English. (6 Pages).
Notification of Office Action dated Nov. 4, 2019 From the National Intellectual Property Administration of the People's Republic of China Re. Application No. 201580076812.7 and Its Translation Into English. (21 Pages).
Applicant-Initiated Interview Summary dated Jan. 23, 2019 From the US Patent and Trademark Office Re. U.S. Appl. No. 16/065,807. (4 pages).
Applicant-Initiated Interview summary dated Apr. 24, 2019 From the US Patent and Trademark Office Re. U.S. Appl. No. 15/538,732.
Applicant-Initiated Interview Summary dated Apr. 24, 2019 From the US Patent and Trademark Office Re. U.S. Appl. No. 16/065,807. (3 Pages).
Applicant-Initiated Interview Summary dated Aug. 24, 2018 From the US Patent and Trademark Office Re. U.S. Appl. No. 14/900,160. (4 pages).
Applicant-Initiated Interview Summary dated Oct. 26, 2016 From the US Patent and Trademark Office Re. U.S. Appl. No. 14/900,160.
Communication Pursuant to Article 94(3) EPC dated Mar. 6, 2017 From the European Patent Office Re. Application No. 14814409.0. (5 Pages).
Communication Pursuant to Article 94(3) EPC dated Jun. 11, 2019 From the European Patent Office Re. Application No. 15872106.8. (7 Pages).
Communication Pursuant to Article 94(3) EPC dated Nov. 16, 2017 From the European Patent Office Re. Application No. 14814409.0. (4 Pages).
Communication Pursuant to Article 94(3) EPC dated Jun. 24, 2020 From the European Patent Office Re. Application No. 15872106.8. (6 Pages).
Communication Pursuant to Article 94(3) EPC dated Aug. 31, 2018 From the European Patent Office Re. Application No. 14814409.0. (5 Pages).
International Preliminary Report on Patentability dated Jul. 5, 2018 From the International Bureau of WIPO Re. Application No. PCT/IL2016/051377. (14 Pages).
International Preliminary Report on Patentability dated Jul. 6, 2017 From the International Bureau of WIPO Re. Application No. PCT/IL2015/051252. (8 Pages).
International Preliminary Report on Patentability dated Dec. 30, 2015 From the International Bureau of WIPO Re. Application No. PCT/IL2014/050559.
International Search Report and the Written Opinion dated Apr. 25, 2016 From the International Searching Authority Re. Application No. PCT/IL2015/051252.

(56) References Cited

OTHER PUBLICATIONS

International Search Report and the Written Opinion dated Mar. 29, 2017 From the International Searching Authority Re. Application No. PCT/IL2016/051377. (21 Pages).
International Search Report dated Oct. 21, 2014 From the International Searching Authority Re. Application No. PCT/IL2014/050559.
Notice of Allowance dated May 14, 2019 From the US Patent and Trademark Office Re. U.S. Appl. No. 15/538,732. (17 pages).
Notice of Allowance dated Feb. 19, 2020 From the US Patent and Trademark Office Re. U.S. Appl. No. 16/065,807. (11 pages).
Notice of Allowance dated Feb. 21, 2020 From the US Patent and Trademark Office Re. U.S. Appl. No. 14/900,160. (26 pages).
Notification of Non-Compliant Amendment dated Feb. 13, 2017 From the US Patent and Trademark Office Re. U.S. Appl. No. 14/900,160. (3 pages).
Notification of Office Action and Search Report dated Nov. 4, 2019 From the National Intellectual Property Administration of the People's Republic of China Re. Application No. 201580076812.7 and Its Translation of Office Action Into English. (18 Pages).
Notification of Office Action and Search Report dated Aug. 22, 2017 From the State Intellectual Property Office of the People's Republic of China Re. Application No. 201480036964. (7 Pages).
Official Action dated May 3, 2019 From the US Patent and Trademark Office Re. U.S. Appl. No. 16/065,807. (23 pages).
Official Action dated Jan. 4, 2019 From the US Patent and Trademark Office Re. U.S. Appl. No. 14/900,160. (40 pages).
Official Action dated Dec. 5, 2018 From the US Patent and Trademark Office Re. U.S. Appl. No. 16/065,807. (22 pages).
Official Action dated Aug. 10, 2016 From the US Patent and Trademark Office Re. U.S. Appl. No. 14/900,160.
Official Action dated Aug. 12, 2019 From the US Patent and Trademark Office Re. U.S. Appl. No. 14/900,160. (27 pages).
Official Action dated Jan. 12, 2018 From the US Patent and Trademark Office Re. U.S. Appl. No. 14/900,160. (47 pages).
Official Action dated Apr. 14, 2017 from the US Patent and Trademark Office Re. U.S. Appl. No. 14/900,160. (43 pages).
Official Action dated Sep. 14, 2018 From the US Patent and Trademark Office Re. U.S. Appl. No. 15/538,732. (30 pages).
Official Action dated Sep. 20, 2019 From the US Patent and Trademark Office Re. U.S. Appl. No. 16/065,807. (25 pages).
Official Action dated May 31, 2018 From the US Patent and Trademark Office Re. U.S. Appl. No. 14/900,160. (42 pages).
Restriction Official Action dated Jul. 6, 2018 From the US Patent and Trademark Office Re. U.S. Appl. No. 15/538,732. (5 pages).
Supplementary European Search Report and the European Search Opinion dated Feb. 7, 2017 From the European Patent Office Re. Application No. 14814409.0. (4 Pages).
Supplementary European Search Report and the European Search Opinion dated Jun. 15, 2018 From the European Patent Office Re. Application No. 15867972.0. (8 Pages).
Supplementary European Search Report and the European Search Opinion dated Jul. 19, 2019 From the European Patent Office Re. Application No. 16877906.4. (7 Pages).
Translation of Notification of Office Action dated Aug. 22, 2017 From the State Intellectual Property Office of the People's Republic of China Re. Application No. 201480036964. (3 Pages).
Written Opinion dated Oct. 21, 2014 From the International Searching Authority Re. Application No. PCT/IL2014/050559.
Kentec Medical "Ameritus Entral™ Feeding Tubes", Kentec Medical, Inc., Premarket Notification, KI00526, 5 P., Apr. 22, 2010.
NeoMed "NeoMed Polyurethane Feeding Tube", NeoMed Inc., K082238, 5 P., Oct. 1, 2008.
Notification of Office Action and Search Report dated Dec. 10, 2020 From the State Intellectual Property Office of the People's Republic of China Re. Application No. 201580076812.7 and Its Translation of Office Action Into English. (15 Pages).
Decision of Rejection dated Sep. 17, 2021 From the Japan Patent Office Re. Application No. 2018-552933 and Its Translation Into English. (4 Pages).
Decision to Refuse dated Nov. 9, 2022 From the European Patent Office Re. Application No. 15872106.8.(18 pages).
Official Action dated Sep. 20, 2022 From the US Patent and Trademark Office Re. U.S. Appl. No. 16/920,782. (31 pages).
Summons to Attend Oral Proceedings Pursuant to Rule 115(1) EPC dated Mar. 31, 2022 From the European Patent Office Re. Application No. 15867972.0. (5 Pages).
Notice of Reason for Rejection dated Dec. 9, 2022 From the Japan Patent Office Re. Application No. 2022-003669 and Its Translation Into English. (8 Pages).
Notice of Allowance dated Jan. 19, 2023 from the US Patent and Trademark Office Re. U.S. Appl. No. 16/920,782. (10 pages).

* cited by examiner

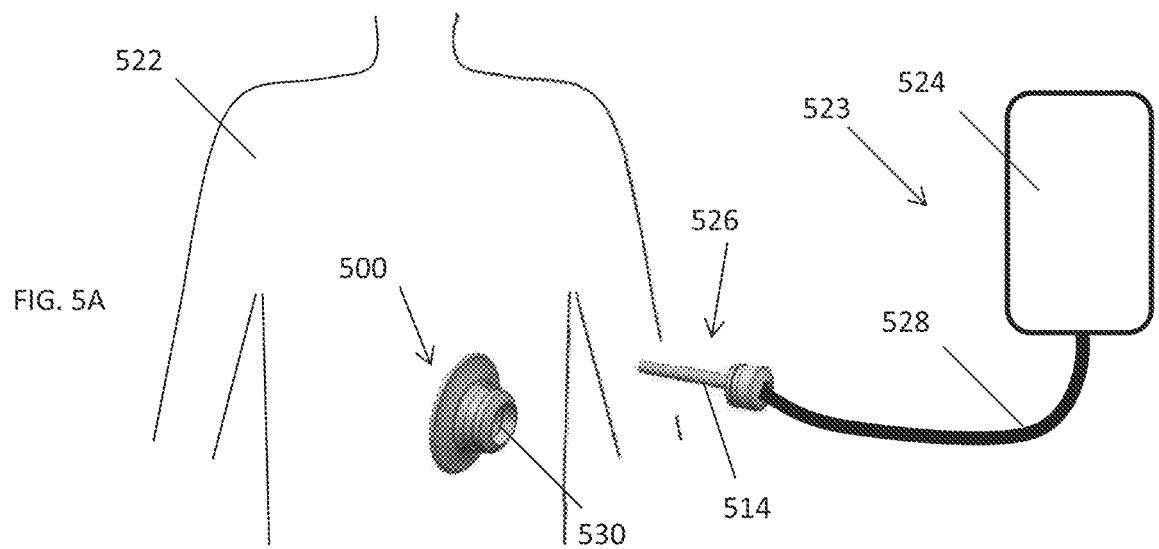
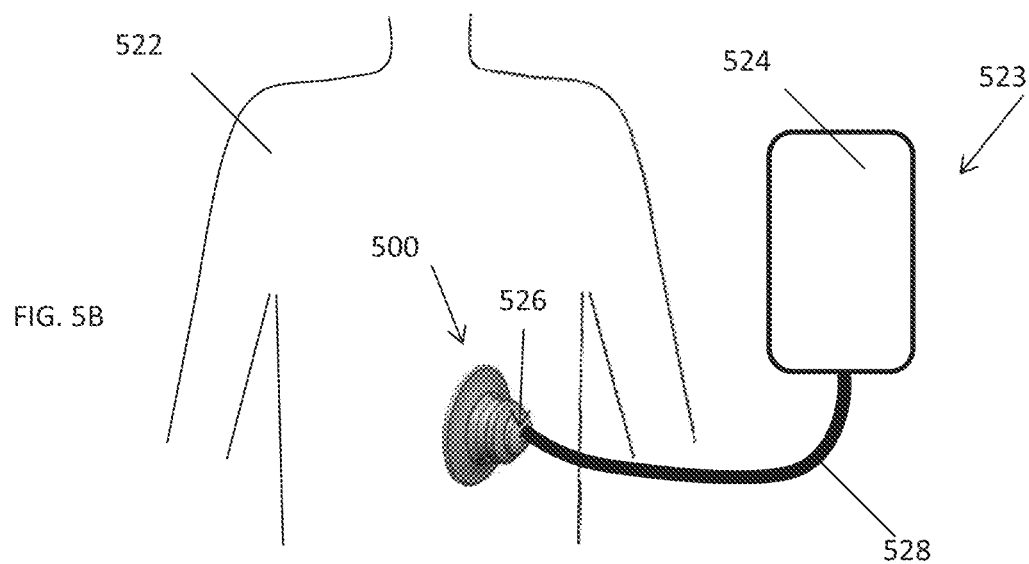
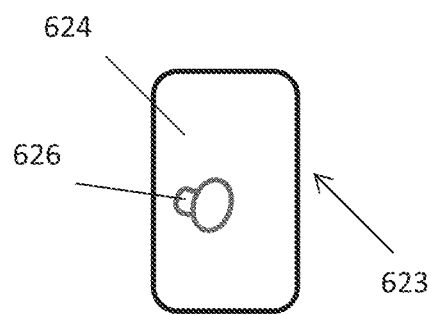
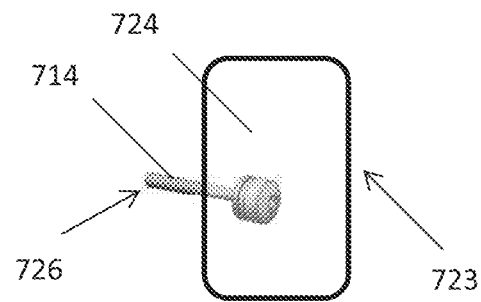
FIG. 5A
FIG. 5B
FIG. 6
FIG. 7

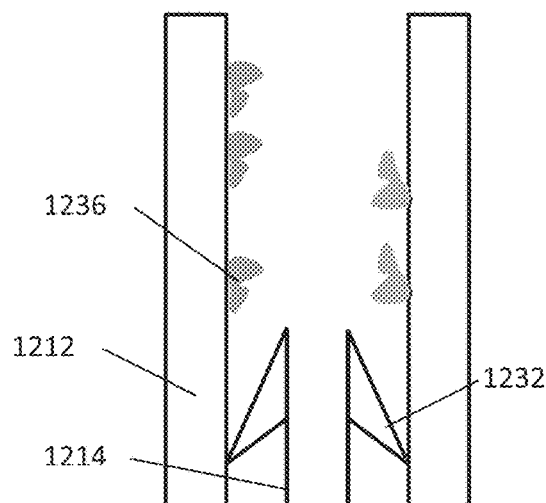
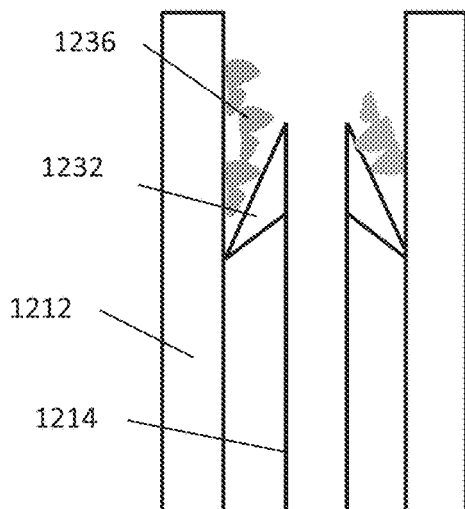
FIG. 12A  FIG. 12B
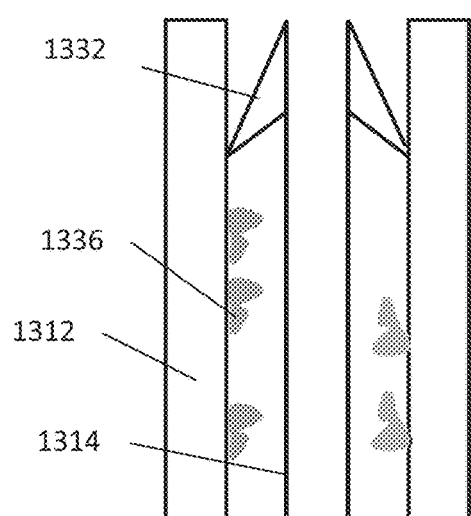
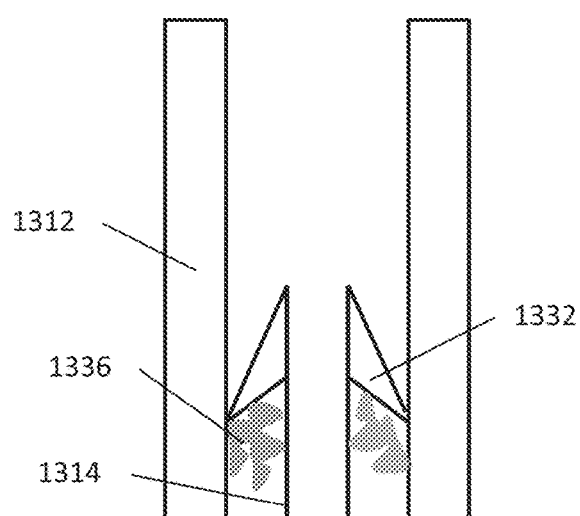
FIG. 13A  FIG. 13B

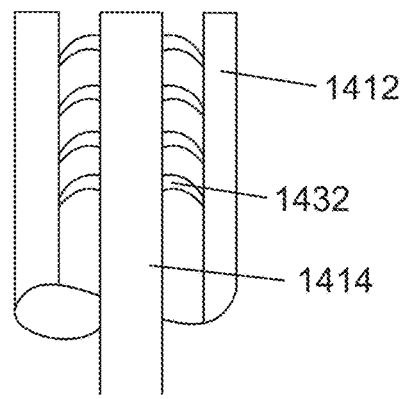
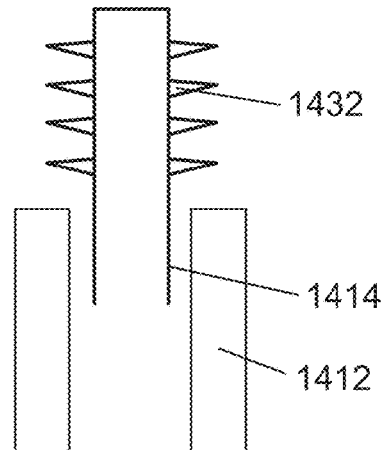
FIG. 14A
FIG. 14B
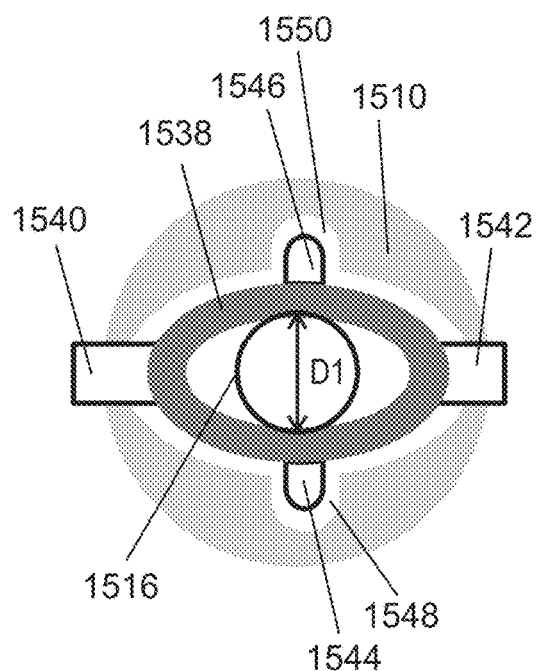
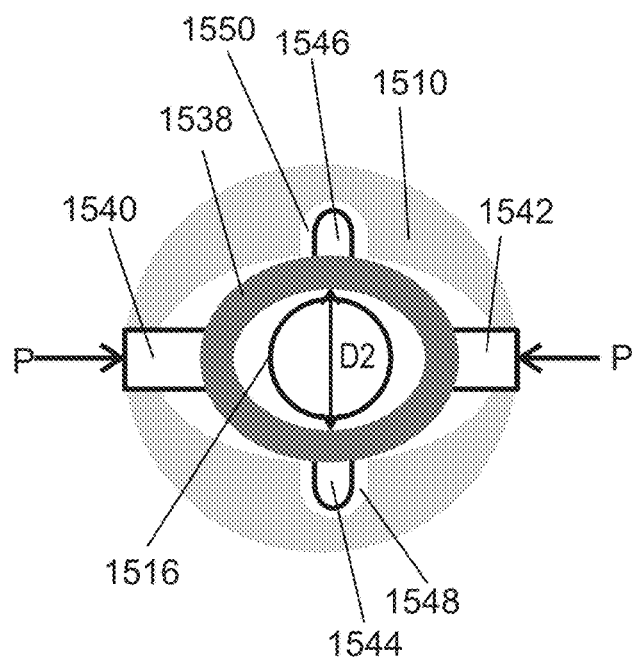
FIG. 15A
FIG. 15B

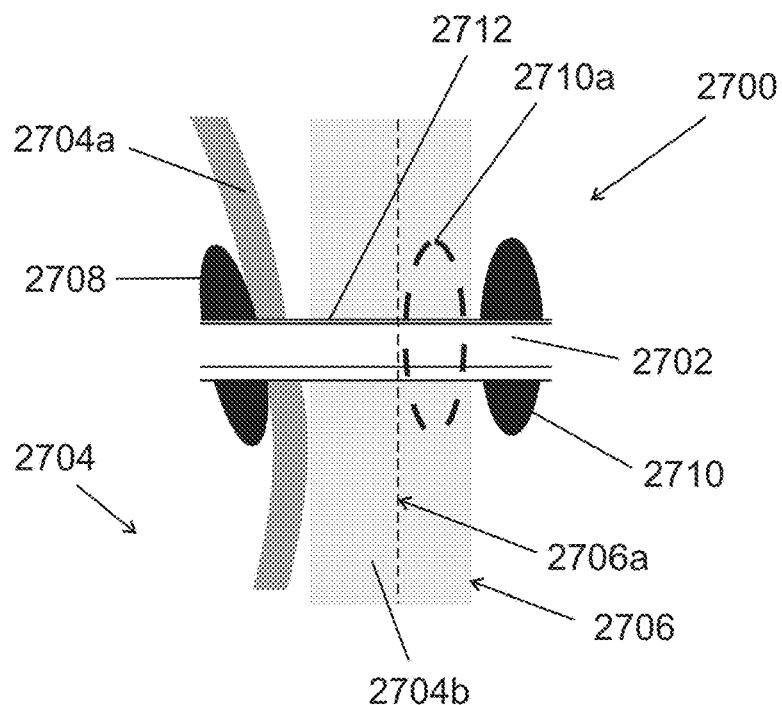
FIG. 27
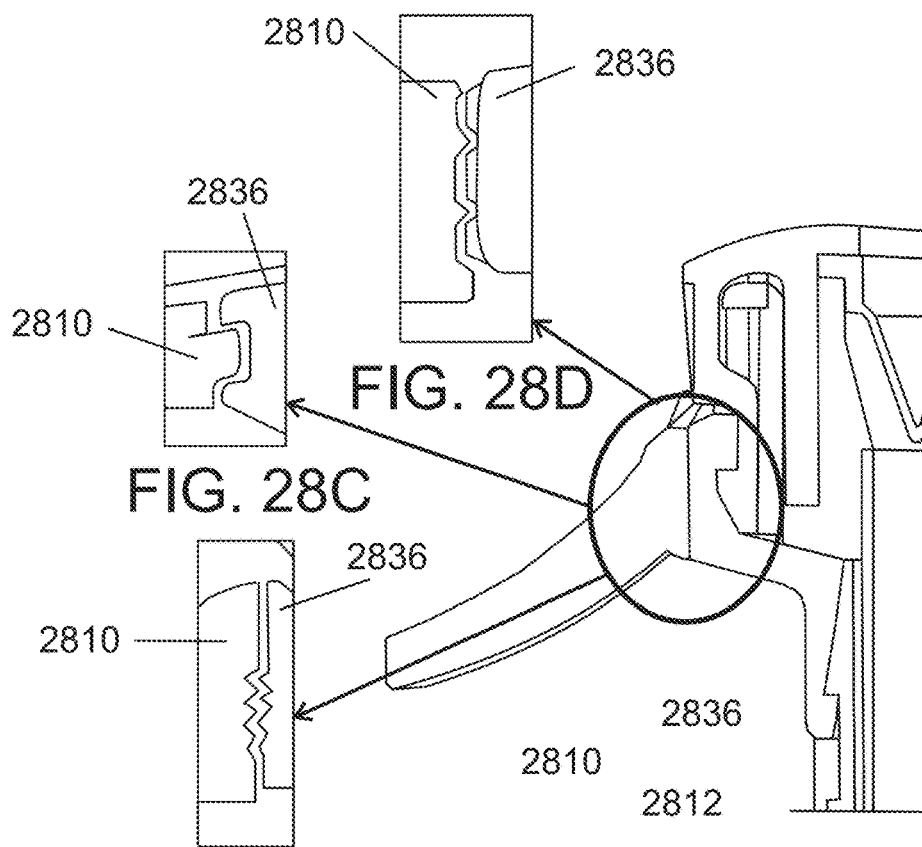
FIG. 28D
FIG. 28C
FIG. 28B  FIG. 28A

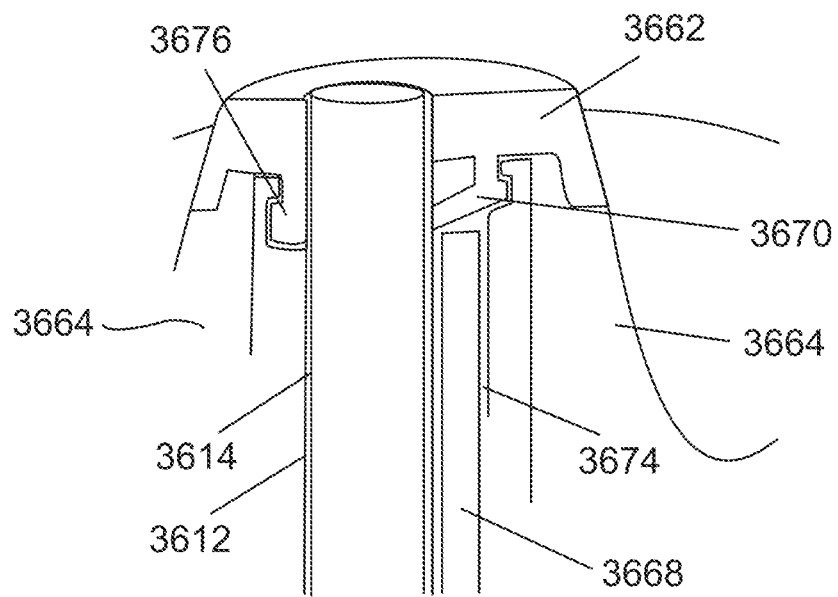
FIG. 36
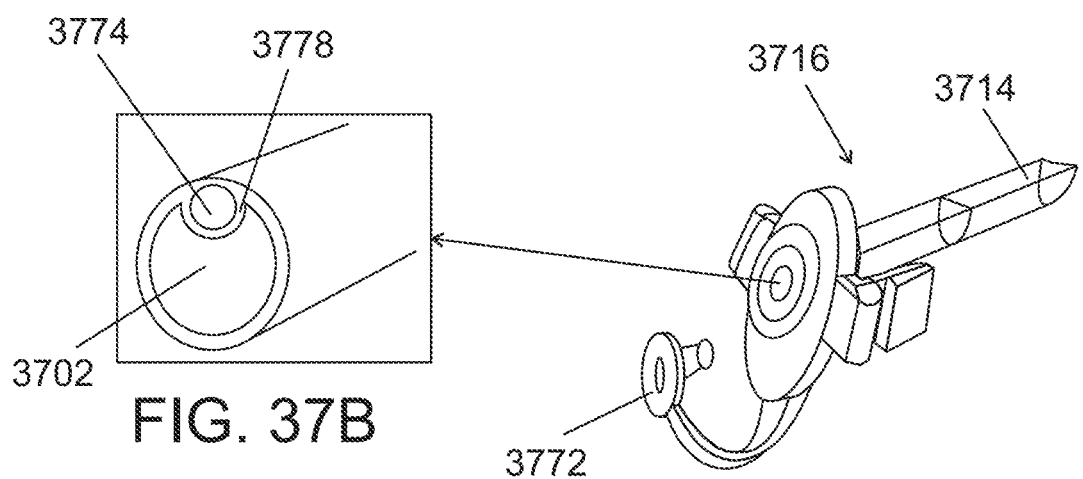
FIG. 37B
FIG. 37A

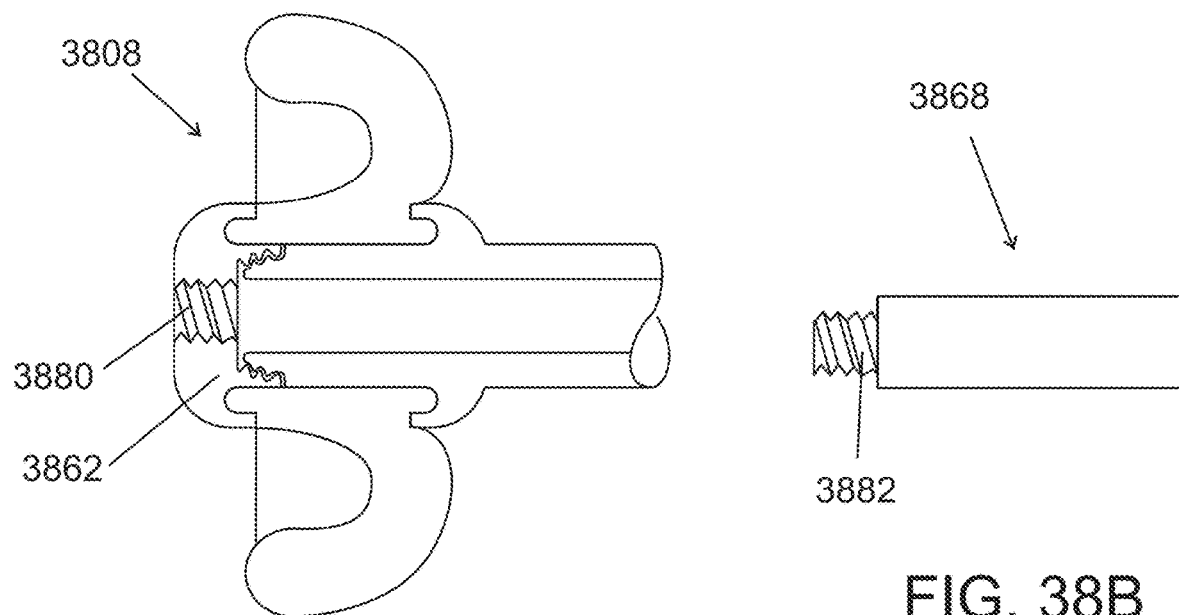
FIG. 38A
FIG. 38B
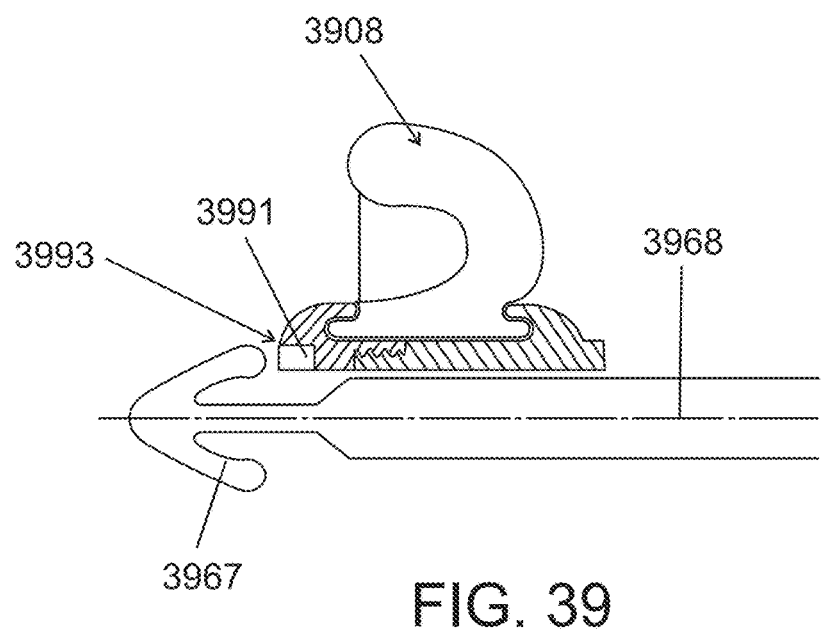
FIG. 39

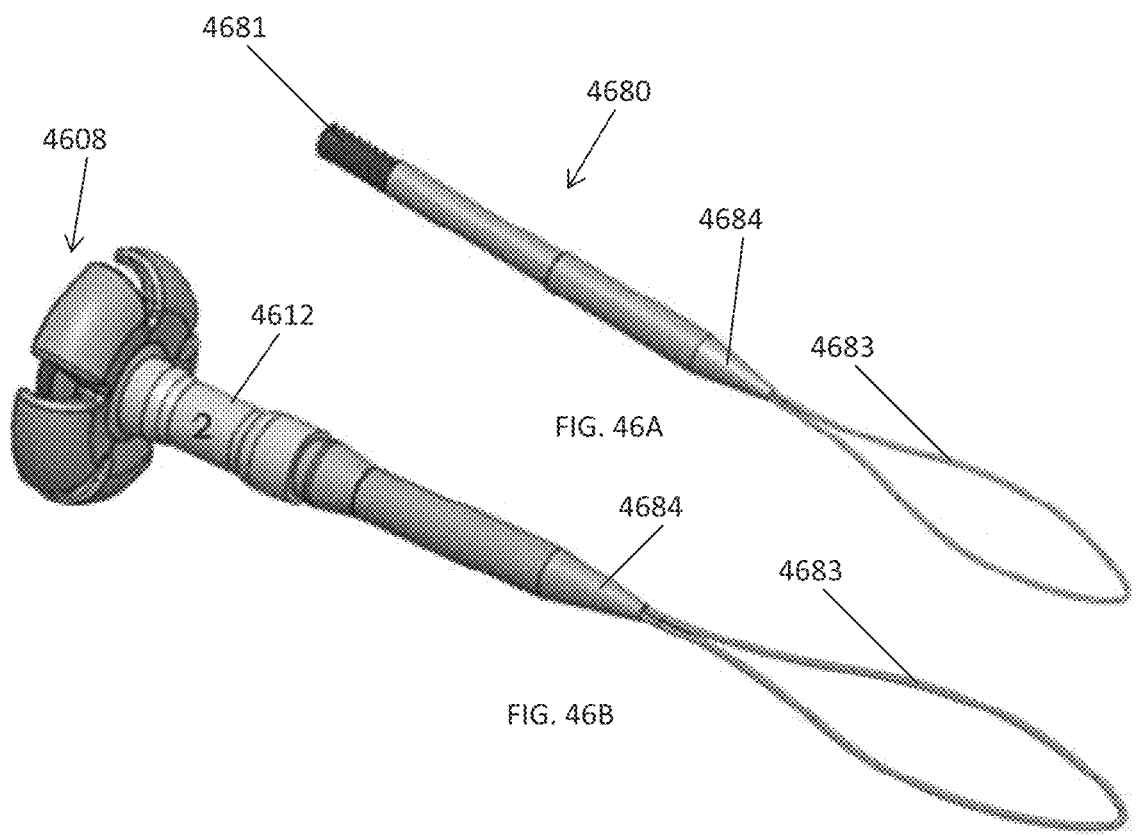
FIG. 46A
FIG. 46B
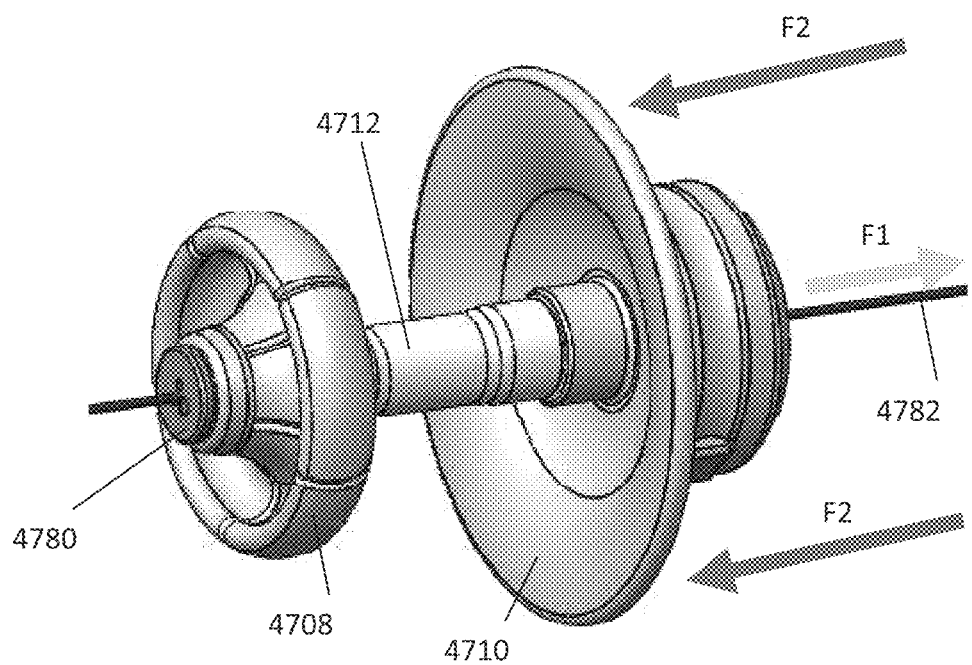
FIG. 47

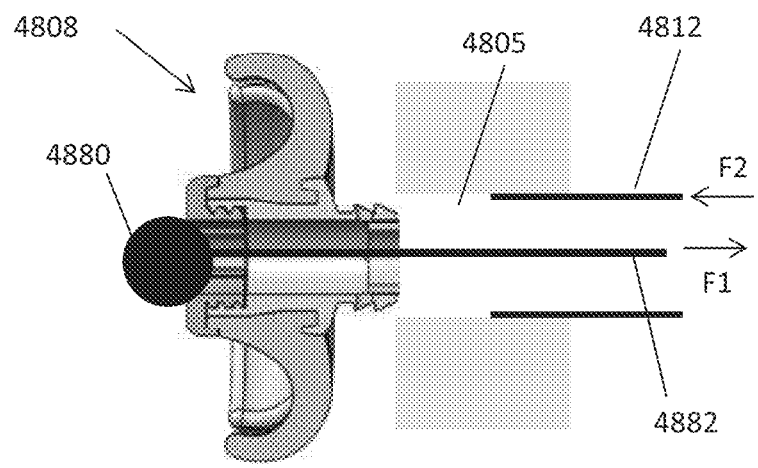
FIG. 48
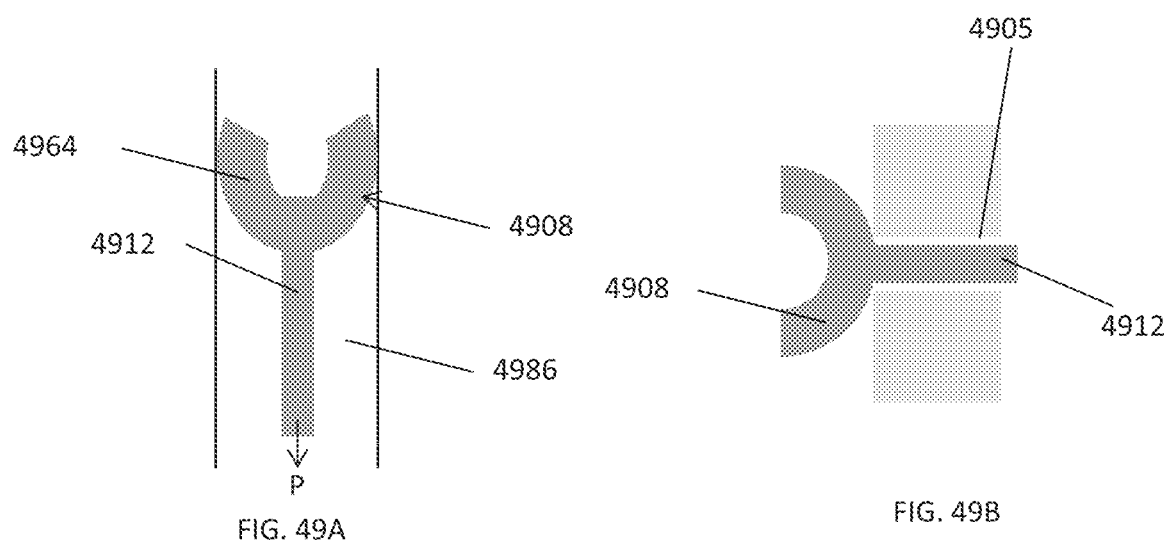
FIG. 49A
FIG. 49B
FIG. 49C
FIG. 49D

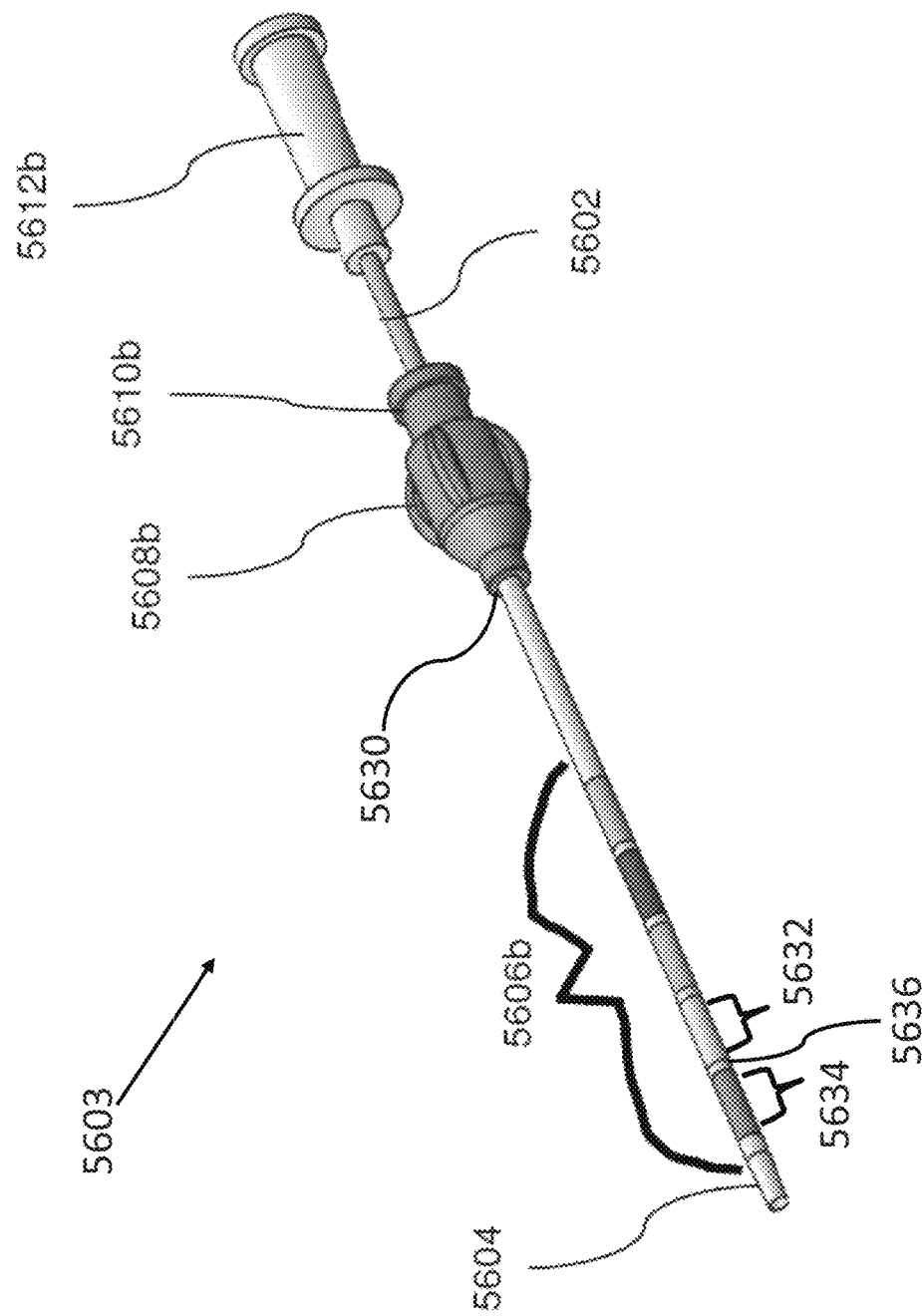

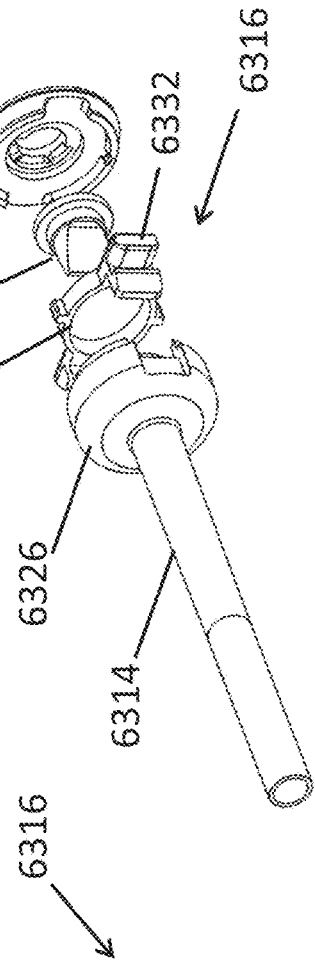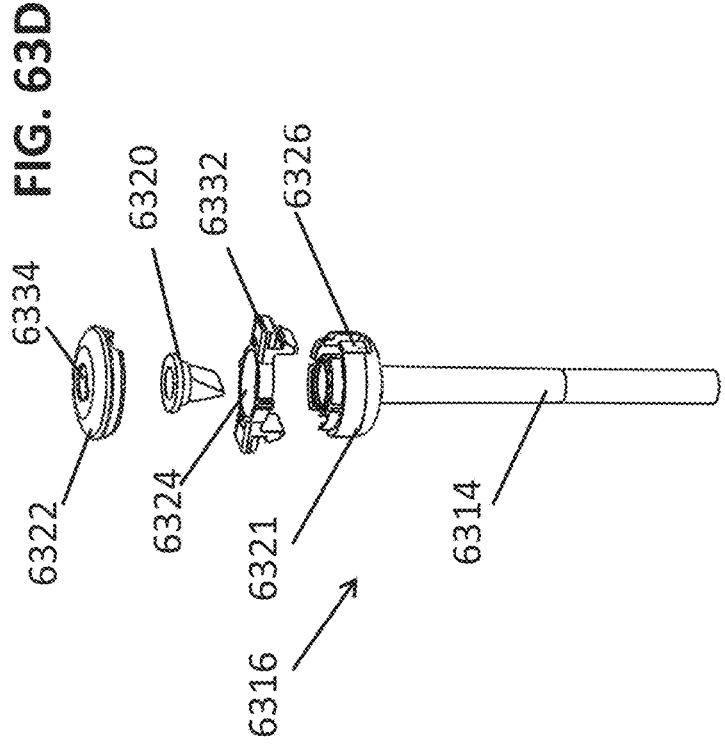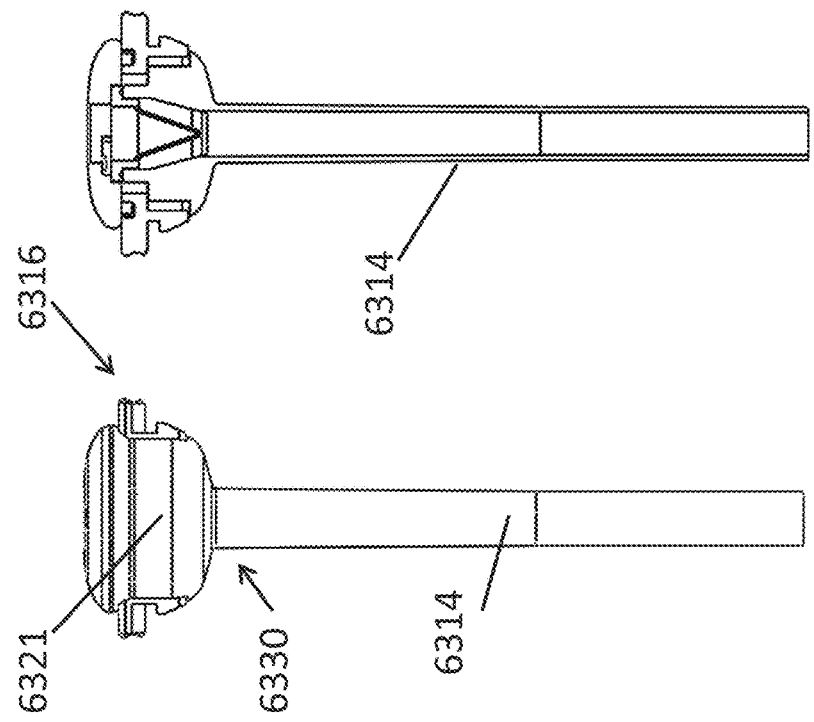

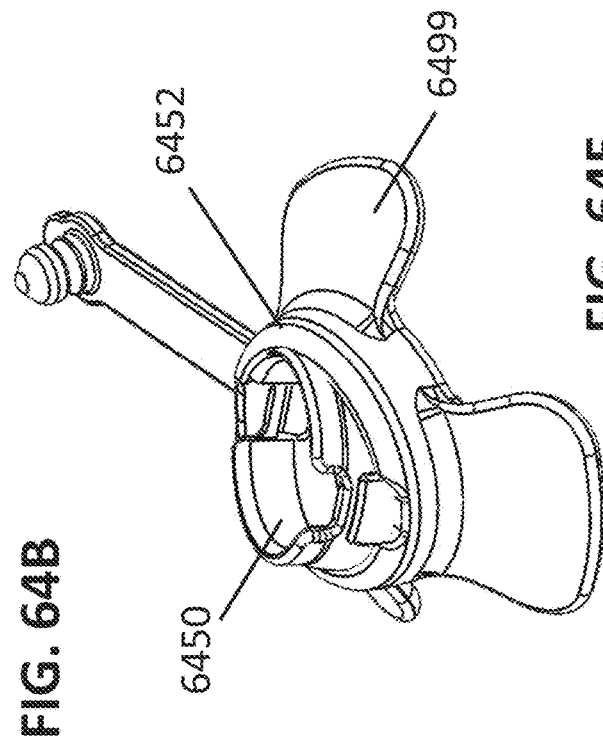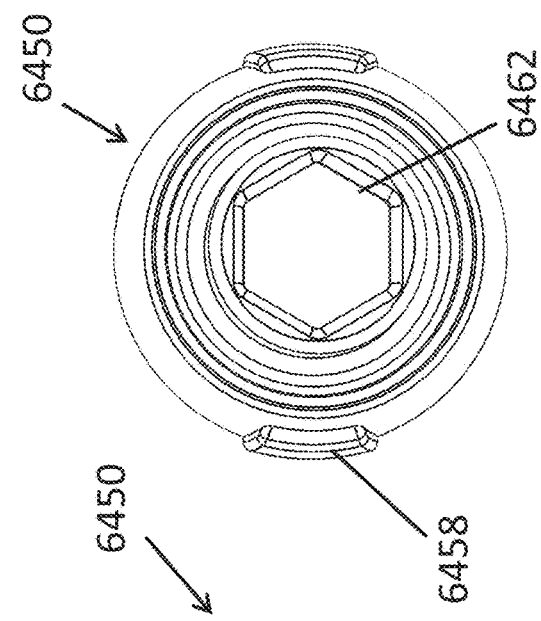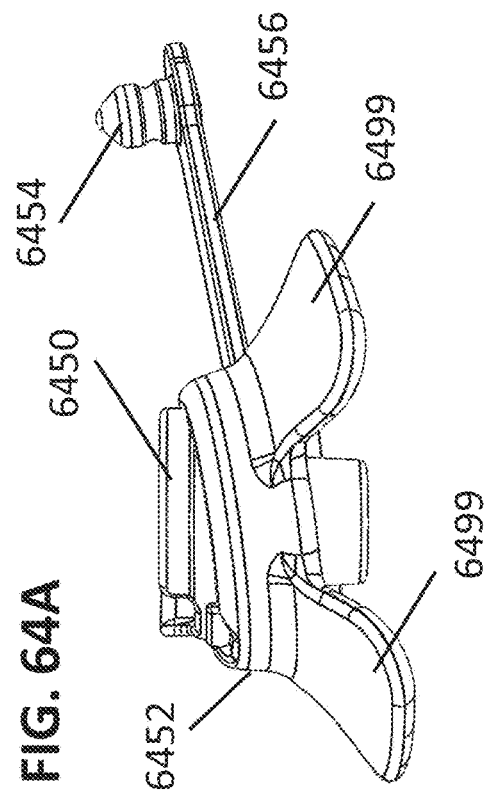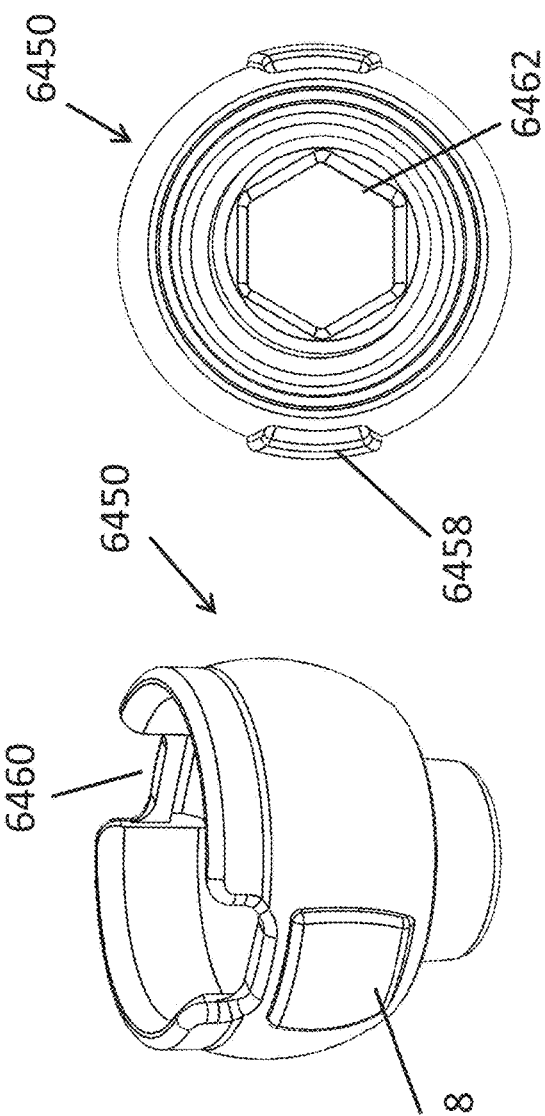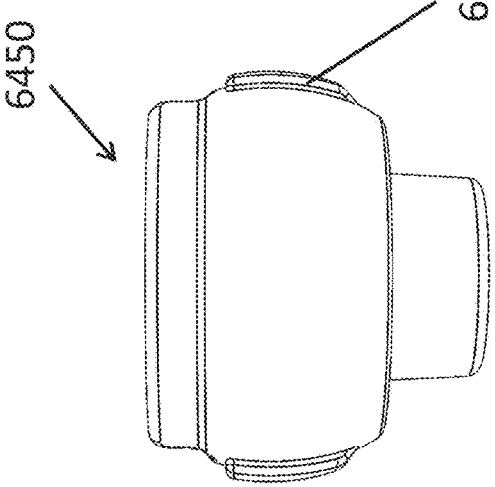

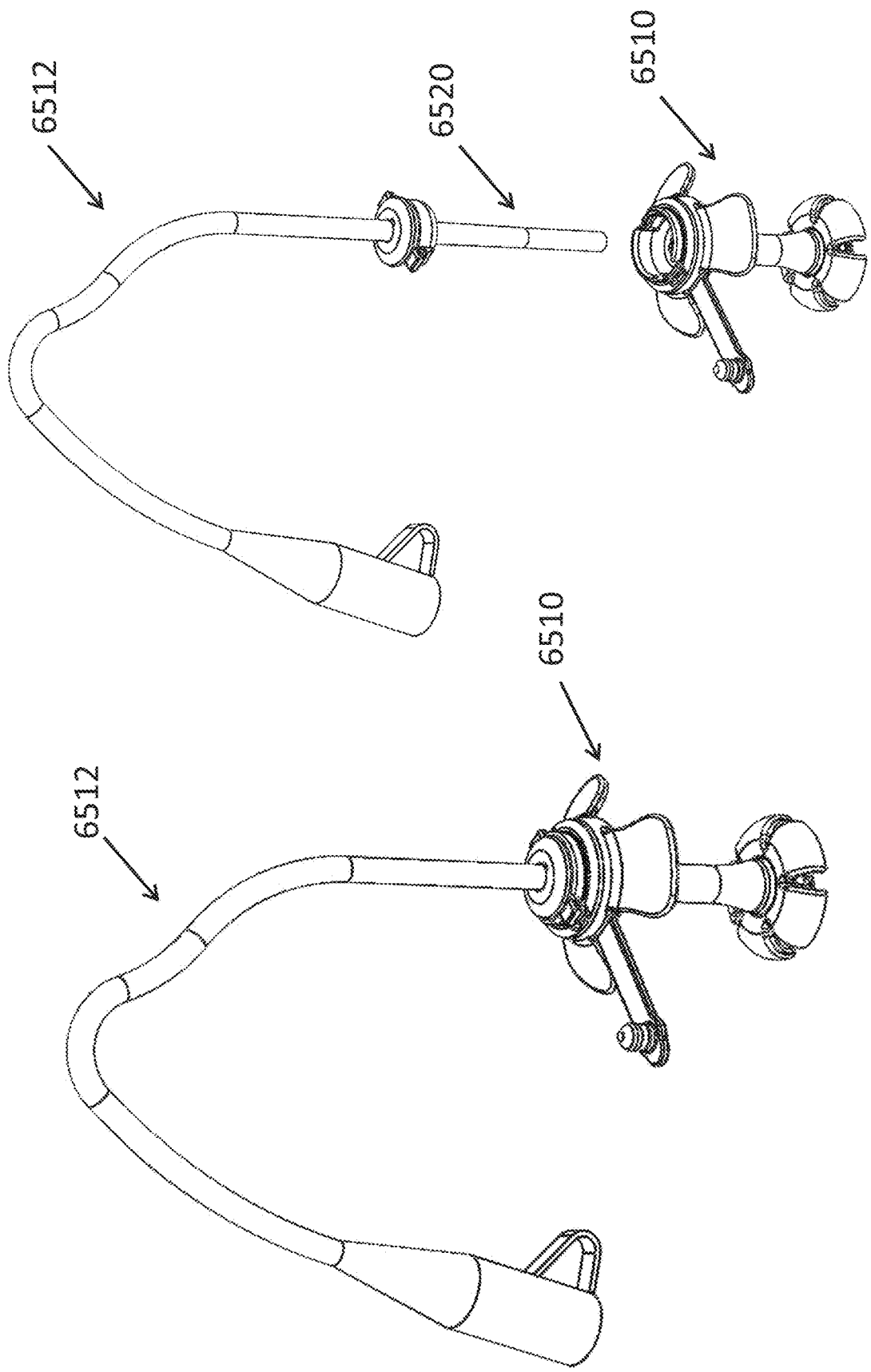

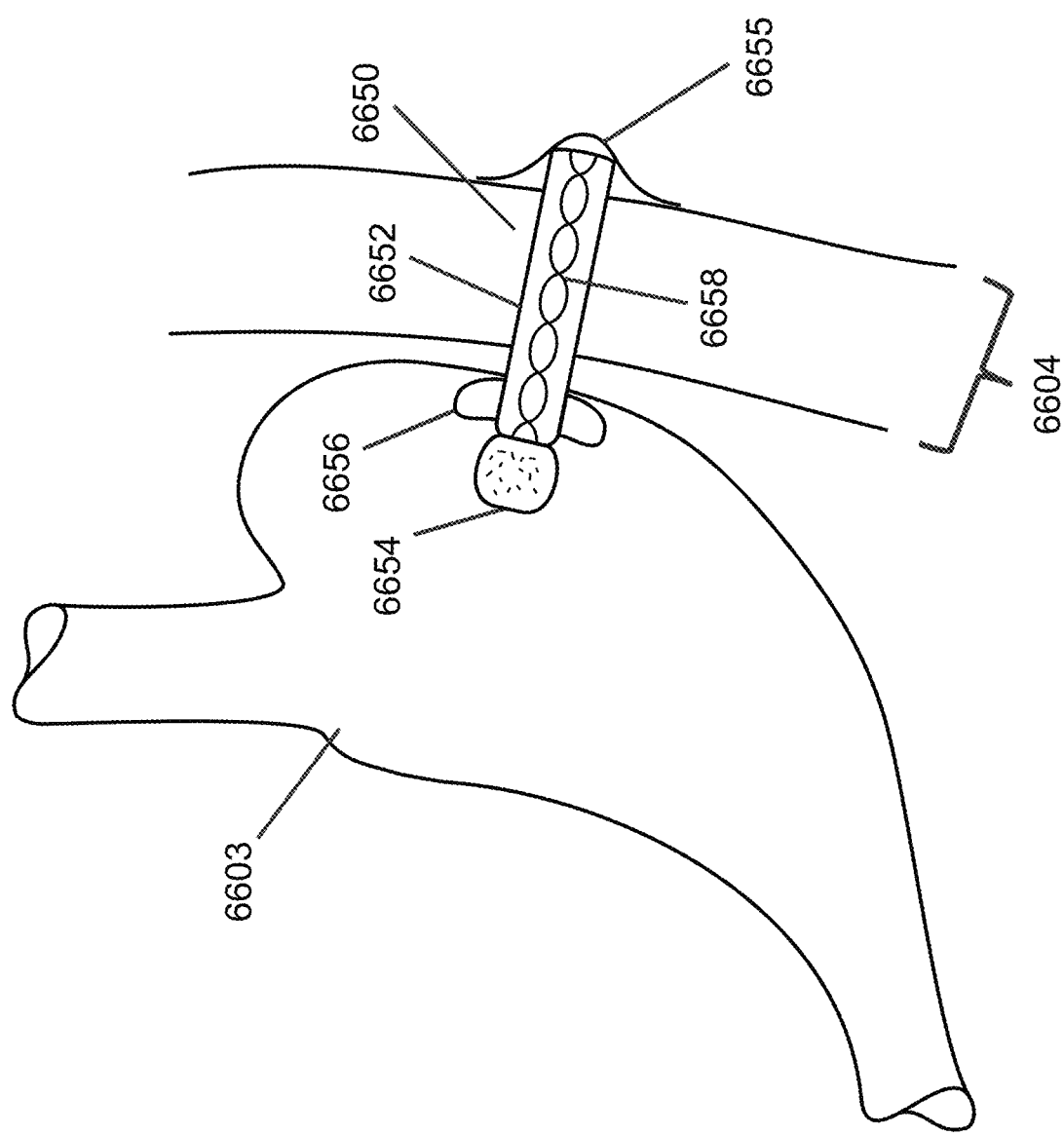

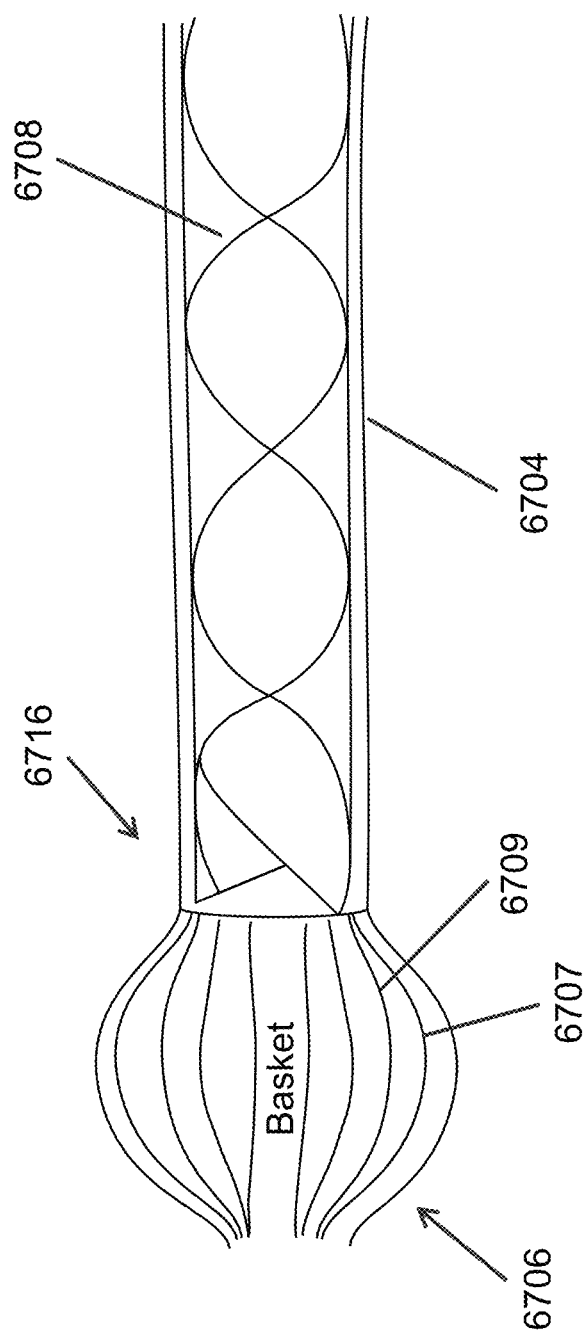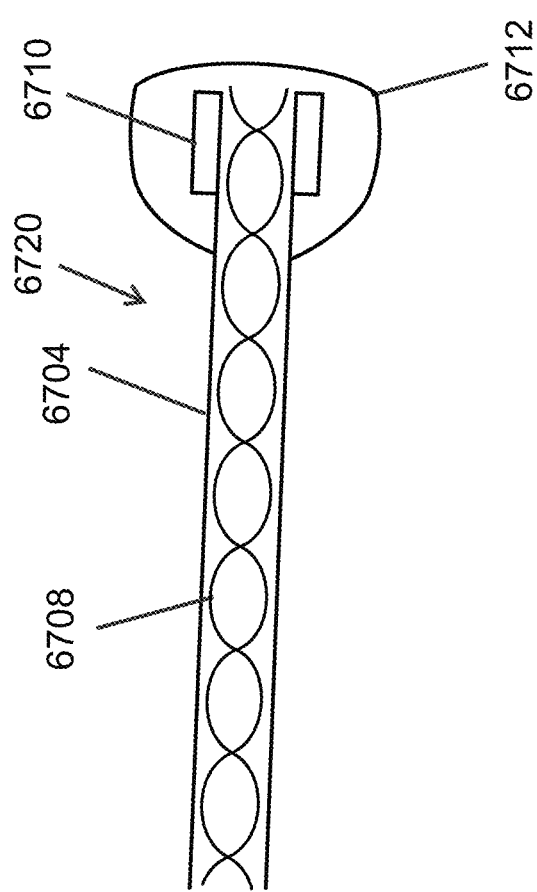

MEASURING DEVICE

RELATED APPLICATIONS

This application is a continuation of U.S. patent application Ser. No. 16/065,807 filed on Jun. 24, 2018, which is a National Phase of PCT Patent Application No. PCT/IL2016/051377 having International Filing Date of Dec. 23, 2016, which claims the benefit of priority under 35 USC § 119(e) of U.S. Provisional Patent Application No. 62/356,482 filed on Jun. 29, 2016.

The contents of the above applications are all incorporated by reference as if fully set forth herein in their entirety.

FIELD AND BACKGROUND OF THE INVENTION

The present invention, in some embodiments thereof, relates to port devices and procedures and, more particularly, but not exclusively, to devices and procedures for percutaneous endoscopic gastronomy (PEG).

U.S. Pat. No. 7,582,072 discloses "A device for creating a channel between the stomach lumen and the abdominal surface of a patient. The device includes a tube and a first bolster. The tube has a proximal end, a distal end, and a wall, the wall having an inner surface and an outer abdominal surface, and each end having an opening therein. The first bolster is attached to the distal end of the tube and the tube is adapted to slidably receive a feeding device having a shaft, wherein at least a portion of the outer diameter of the shaft of the feeding device is substantially the same size as that of the inner wall of the tube. The first bolster is adapted to sealingly engage with the patient so as to minimize or avoid fluid leakage about the tube. The present invention is also directed to a method of using an artificial stoma."

U.S. Patent Application Publication No. US2003/0163119 discloses "A medical catheter assembly including a removable inner sleeve. In one embodiment, the assembly is a low profile percutaneous endoscopic gastrostomy (PEG) device and comprises a body, a clamp, a feeding tube, a cap and an inner sleeve assembly. The body includes a base portion and a sleeve portion, the base portion being dimensioned to engage the skin of a patient and having a transverse bore, the sleeve portion extending upwardly from the base portion and having a longitudinal slot aligned with the transverse bore and a transverse slot intersecting the longitudinal bore. The clamp, which is slidably mounted on the base portion and across the transverse slot of the sleeve, comprises a plate having a transverse opening. The transverse opening has a wide region and a narrow region, the two regions being alternately alignable with the longitudinal bore to open and to close, respectively, the feeding tube. The feeding tube has a distal end adapted to be anchored to the inside of a patient and a proximal end inserted up through the base portion and the sleeve portion, including the transverse opening of the clamp situated within the sleeve, and then inverted over the top edge of the sleeve. The cap is then mounted on top of the sleeve so as to secure the inverted end of the catheter to the exterior of the sleeve. The cap is provided with an opening through which access to the catheter may be gained. An inner sleeve, sized to engage the inside surface of the feeding tube, is removably inserted through the cap and the feeding tube, the inner sleeve having a proximal end to which a tubular fitting is secured. Food and/or medications are dispensed to the patient through the fitting and the inner sleeve and, in this manner, prevent clogging of the feeding tube."

SUMMARY OF THE INVENTION

According to an aspect of a first embodiments of the invention, there is provided a PEG feeding device for conducting fluid through a stoma to a stomach comprising: a tube sized to bridge a channel between a stomach and an outer abdominal surface; an internal bolster, sized to resist movement out of the stomach through the stoma and connected to the tube; an external bolster, sized to resist movement into the stoma and connected to the tube; wherein the external bolster includes at least one element including an underside which extends from the tube in a radial direction and then towards the external bolster contacting the outer abdominal surface at a distance from an external opening of the stoma.

According to a second and optionally according to the first embodiments of the invention, the distance is at least 5 mm.

According to a third and optionally according to any of the first to the second embodiments of the invention, at least a portion of the external bolster is elastically deflectable in an axial direction.

In some embodiments, said reading comprises reading using an intrabody imager includes viewing said marker at said location.

According to a fourth and optionally according to any of the first to the third embodiments of the invention, the external bolster includes a plurality of portions which are individually elastically deflectable.

According to a fifth and optionally according to the fourth embodiments of the invention, the portions are at least partially circumferentially separated.

In some embodiments, said graduations comprise color-coded graduations.

According to a sixth and optionally according to any of the first to the fifth embodiments of the invention, at least a portion of the inner bolster is elastic with respect to a long axis of the tube.

In some embodiments, said marker comprises at least one separating section between adjacent graduations.

According to a seventh and optionally according to any of the first to the sixth embodiments of the invention, the internal bolster includes a plurality of parts connected by at least one connector.

There is provided in accordance with some embodiments, a method for inserting a PEG device into a stomach lumen, comprising:
determining a thickness of tissue between the stomach and skin to a precision of 4 mm or better;
selecting a permanent PEG tube having a bridging length corresponding to said determined thickness;
inserting said selected permanent PEG tube to bridge between said skin and said stomach; and
compensating for a mismatch between said bridging length and said thickness using at least one elastic bolster positioned against the skin and/or against the stomach wall.

According to an eighth and optionally according to any of the first to the seventh embodiments of the invention, the internal bolster includes circumferential separations.

In some embodiments of the invention, said compensating comprises attaching an elastic outer bolster to said tube.

According to a ninth and optionally according to any of the first to the eighth embodiments of the invention, the PEG feeding device comprises an inner tube sized to fit into the tube and to bridge a channel between a stomach and a patient outer abdominal surface.

In some embodiments of the invention, when said compensating, said at least one elastic bolster applies a pressure on said tissue lower than a tissue damaging pressure.

According to a tenth and optionally according to the ninth embodiments of the invention, the inner tube is permanently attached to a food reservoir.

In some embodiments of the invention, said determining comprises determining by visualizing markings of a measuring device that bridges said thickness, from within said stomach lumen.

According to an eleventh and optionally according to any of the ninth to tenth embodiments of the invention, the PEG feeding device comprises a rigid connector connecting the inner tube and the external bolster.

There is provided in accordance with some embodiments, a PEG feeding device comprising:
  a tube; wherein said tube is shaped and sized to be positioned between a stomach lumen and the outer surface of the skin;
  an internal bolster and an external bolster, at least one of which being elastic, connected to said tube, wherein said elasticity allows deformation of one or both of said bolster so as to vary the distance between the two bolsters by at least 4 mm, while not applying a tissue-damaging pressure to said lumen or said skin.

According to a twelfth and optionally according to any of the ninth to eleventh embodiments of the invention, the PEG feeding device according comprises a sealing element occluding a channel between the tube and the inner tube.

In some embodiments of the invention, said tube is connected to said external bolster by an interference mechanism configured to prevent both relative rotation and release of said external bolster from said tube.

According to a thirteenth and optionally according to any of the ninth to twelfth embodiments of the invention, the inner tube includes at least one cleaning portion sized to contact inner walls of the tube.

In some embodiments of the invention, said interference mechanism comprises matching geometries between said external bolster and said tube.

According to a fourteenth and optionally according to the thirteenth embodiments of the invention, the cleaning portion elastically applies radial pressure to the inner walls of the tube.

In some embodiments of the invention, said tube includes a geometric shape which guides a mounting of said bolster over said shape in an orientation matching an orientation of the interference mechanism.

According to a fifteenth and optionally according to any of the first to fourteenth embodiments of the invention, the tube connects to one of the internal bolster and the external bolster by a rigid connector.

There is provided in accordance with some embodiments, a kit for measuring tissue thickness, comprising:
  (a) a cannula having a proximal size adapted to remain outside the body and a distal side adapted to pierce tissue and enter the body;
  (b) a marked shaft sized to fit in said cannula and fixedly abut against a portion of said cannula which remains outside the body, when the shaft is moved axially through the cannula,
    wherein said shaft includes a plurality of markings which extend past said distal end of said cannula when said shaft fixedly abuts said portion of said cannula.

According to a sixteenth and optionally according to any of the first to the fifteenth embodiments of the invention, a height of the device above a patient outer abdominal surface is less than 5 cm.

There is provided in accordance with some embodiments, a PEG feeding device for conducting fluid through a stoma to a stomach comprising:
  a tube sized to bridge a channel between the stomach and an outer abdominal surface;
  an internal bolster, sized to resist movement out of the stomach through the stoma and connected to said tube; and
  an external bolster, sized to resist movement into the stoma and connected to said tube;
  wherein said external bolster includes at least one elastic element positioned between a connection to said tube and an interface contacting said outer abdominal surface and wherein a shortest path on said elastic element from said connection to said interface is at least 20% longer than a straight line joining said connection to said interface.

According to a seventeenth and optionally according to any of the first to the sixteenth embodiments of the invention, an axial height of the external bolster is less than 5 cm.

In some embodiments of the invention, said internal bolster further comprises a central shaft and at least 3 spaced apart petals connected to said central shaft via a connecting end of said petals.

According to a eighteenth and optionally according to any of the first to the seventeenth embodiments of the invention, the external bolster is connected to the outer tube by a rigid connector.

In some embodiments of the invention, said width of said connecting end is at least 5% larger than the cross-sectional geometry of an outer end of said petals.

According to an nineteenth and optionally according to any of the first to the eighteenth embodiments of the invention, the PEG further comprises: a variable angle joint joining the external bolster to the tube and allowing the external bolster to tilt with respect the tube.

In some embodiments of the invention, said central shaft has a hardness of at least 40 shore A.

According to an aspect of a twentieth embodiment of the invention, there is provided a PEG feeding device for conducting fluid through a stoma to a stomach comprising: a tube sized to bridge a channel between a stomach and an outer abdominal surface; a bolster sized to resist movement into the stoma; and a rigid connector comprising a lumen and connecting the tube to the bolster; wherein a portion of the rigid connector is disposed within a first end of the tube.

There is provided in accordance with some embodiments, a PEG feeding device for conducting fluid through a stoma to a stomach comprising:
  a tube sized to bridge a channel between the stomach and an outer abdominal surface;
  an internal bolster, sized to resist movement out of the stomach through the stoma and connected to said tube; and
  an external bolster, sized to resist movement into the stoma and connected to said tube;
  wherein said external bolster includes at least one elastic element positioned between a connection to said tube and an interface contacting said outer abdominal surface and wherein said elastic element is shaped and sized to transmit a force between said interface and said connection by means of an axial stress on the elastic element.

According to a twenty first and optionally according to the twentieth embodiments of the invention, the portion of the rigid connector comprises a fitted friction fit with the tube.

In some embodiments of the invention, said interface contacts said outer abdominal surface at a radial distance from an external opening of said stoma.

According to a twenty second and optionally according to any of the first to the twenty first embodiments of the invention, the first end of the tube comprises thickened walls.

In some embodiments of the invention, said interface includes an underside of said elastic element.

According to a twenty third and optionally according to any of the first to the twenty second embodiments of the invention, the tube comprises an internal supporting structure and within a sheath.

In some embodiments of the invention, said distance is at least 5 mm.

According to a twenty forth and optionally according to the twenty third embodiments of the invention, the internal structure includes a mesh.

In some embodiments of the invention, at least a portion of said external bolster is elastically deflectable in an axial direction.

According to a twenty fifth and optionally according to any of the first to the twenty fourth embodiments of the invention, the internal structure includes elongated elements.

In some embodiments of the invention, at least a portion of said external bolster is elastically deflectable in an axial direction.

According to a twenty sixth and optionally according to any of the first to the twenty fifth embodiments of the invention, the PEG feeding device comprises a second bolster sized to resist movement into the stoma; wherein the second bolster is connected to a second end of the tube.

In some embodiments of the invention, said portions are at least partially circumferentially separated.

According to a twenty seventh and optionally according to any of the first to the twenty sixth embodiments of the invention, the rigid connector connects to a rigid part of the bolster.

In some embodiments of the invention, at least a portion of said inner bolster is elastic with respect to a long axis of said tube.

According to a twenty eighth and optionally according to any of the first to the twenty seventh embodiments of the invention, the rigid connector connects to the bolster by an interference connection.

In some embodiments of the invention, said internal bolster includes a plurality of parts connected by at least one connector.

According to an aspect of a twenty ninth and optionally according to any of the first to the twenty eighth embodiments of the invention, there is provided a PEG feeding device for conducting fluid through a stoma to a stomach comprising: a tube sized to bridge a channel between a stomach and an outer abdominal surface; an internal bolster, sized to resist movement out of the stomach through the stoma and connected to the tube comprising: a plurality of parts held together by one or more connector; and an external bolster, sized to resist movement into the stoma and connected to the tube; wherein the plurality of parts overlap axially by less than 20%.

In some embodiments of the invention, said internal bolster includes circumferential separations.

According to a thirtieth and optionally according to any of the first to the twenty ninth embodiments of the invention, the connector includes a torque connection.

In some embodiments of the invention, the PEG feeding device comprising an inner tube sized to fit into said tube and to bridge a channel between a stomach and a patient outer abdominal surface.

According to an aspect of a thirty first embodiment of the invention, there is provided a method of installing a PEG feeding device comprising: selecting an approximately sized tube; installing the tube in a stoma connecting a stomach and an outer abdominal surface of a patient where an installed tube is held by an inner bolster disposed within the stomach and an external bolster at an abdominal outer surface; compensating for a discrepancy between the tube length and a length of the stoma.

In some embodiments of the invention, the PEG feeding device comprising a rigid connector connecting said inner tube and said external bolster.

According to a thirty second and optionally according to the thirty first embodiments of the invention, the compensating comprises: adjusting a minimum separation between the inner bolster and the external bolster.

In some embodiments, said inner tube is part of an inner tube section which is connected to said external bolster by a snap fit locking mechanism.

According to a thirty third and optionally according to the thirty second embodiments of the invention, the adjusting comprises changing a position of attachment of the bolster with respect to the tube.

In some embodiments of the invention, said inner tube portion comprises an external tube connector, wherein said external tube connector is configured to connect said inner tube portion to an external feeding tube with a greater resistance to a pull-out force than said snap fit locking mechanism.

According to a thirty fourth and optionally according to any of the thirty second to the thirty third embodiments of the invention, the adjusting comprises: selecting an axial extent of a compressible element between an inner bolster and a lumen inner wall.

In some embodiments, said tube connects to one of said internal bolster and said external bolster by a rigid connector.

According to a thirty fifth and optionally according to any of the thirty second to the thirty fourth embodiments of the invention, the adjusting comprises: axially elastically deflecting a portion of the external bolster.

In some embodiments of the invention, said tube comprises a flared section positioned at least partially within said stomach.

According to a thirty sixth and optionally according to any of the thirty second to the thirty fifth embodiments of the invention, the adjusting comprises: axially elastically deflecting a portion of the inner bolster.

There is provided in accordance with some embodiments, a PEG feeding device for conducting fluid through a stoma to a stomach comprising:
  a tube sized to bridge a channel between the stomach and an outer abdominal surface;
  a bolster sized to resist movement into the stoma; and
  a rigid connector comprising a lumen and connecting said tube to said bolster;
  wherein a portion of said rigid connector is disposed within a first end of said tube.

According to a thirty seventh and optionally according to any of the thirty second to the thirty sixth embodiments of the invention, the adjusting is self adjusting of the PEG device.

In some embodiments of the invention, said portion of said rigid connector comprises a fitted friction fit with said tube.

According to an aspect of a thirty eight and optionally according to any of the thirty first to the thirty seventh embodiments of the invention, there is provided a method of use of a PEG feeding device: installing a PEG feeding device comprising an inner and outer tube the outer tube forming a channel between a lumen and a patient outer abdominal surface, the inner tube forming a channel between a lumen and a patient outer abdominal surface and within the outer tube; and replacing the inner tube periodically.

In some embodiments of the invention, said tube comprises an internal supporting structure and within a sheath.

According to a thirty ninth and optionally according to any of the thirty first to the thirty eighth embodiments of the invention, the replacing comprises cleaning said outer tube.

In some embodiments of the invention, said internal structure includes a mesh.

According to a fortieth and optionally according to the thirty eighth embodiments of the invention, the method further comprises: pivoting an angle between at least one of the internal bolster and the external bolster with respect to the tube.

In some embodiments of the invention, said internal structure includes elongated elements.

According to a forty first and optionally according to the fortieth embodiments of the invention, pivoting compensates for a difference between an axis of the tube and a normal from at least one of an inner surface of a stomach and an outer surface of an abdomen at the location of a stoma.

In some embodiments of the invention, the PEG feeding device comprising a second bolster sized to resist movement into the stoma;
 wherein said second bolster is connected to a second end of said tube.

According to an aspect of a forty second and optionally according to any of the first to the thirtieth embodiments of the invention, there is provided a PEG feeding device for conducting fluid through a stoma to a stomach comprising: a tube sized to bridge a channel between a stomach and an outer abdominal surface; an external bolster, sized to resist movement into the stoma and connected to the tube; a variable angle joint joining the external bolster to the tube and allowing the external bolster to tilt with respect the tube.

There is provided in accordance with some embodiments, A PEG feeding device for conducting fluid through a stoma to a stomach comprising:
 a tube sized to bridge a channel between the stomach and an outer abdominal surface;
 an internal bolster, sized to resist movement out of the stomach through the stoma and connected to said tube comprising:
  a plurality of parts held together by one or more connector; and
 an external bolster, sized to resist movement into the stoma and connected to said tube;
 wherein said plurality of parts overlap axially by less than 20%.

According to a forty third and optionally according to the forty second embodiments of the invention, the PEG further comprises: an adjuster for setting a resistance of the external bolster to tilt with respect to an axis of the tube.

In some embodiments of the invention, said connector includes a torque connection.

According to a forty fourth and optionally according to any of the fortieth to the forty third embodiments of the invention, the PEG further comprises: at least one element including an underside which extends from the tube in a radial direction and then towards the external bolster contacting the outer abdominal surface at a distance from an external opening of the stoma.

There is provided in accordance with some embodiments, a method of installing a PEG feeding device comprising:
 selecting an approximately sized tube;
 installing said tube in a stoma connecting a stomach and an outer abdominal surface of a patient where an installed tube is held by an inner bolster disposed within said stomach and an external bolster at an abdominal outer surface; and
 compensating for a discrepancy between said tube length and a length of said stoma.

According to a forty fifth and optionally according to any of the fortieth to the forty fourth embodiments of the invention, the PEG further comprises: an internal bolster, sized to resist movement out of the stomach through the stoma and connected to the tube.

In some embodiments of the invention, said compensating comprises:
 adjusting a minimum separation between said inner bolster and said external bolster.

According to a forty sixth and optionally according to any of the fortieth to the forty fifth embodiments of the invention, the PEG further comprises: an elastic biasing element biasing an angle of the tilting of the external bolster to a preferred angle.

In some embodiments, said adjusting comprises changing a position of attachment of said bolster with respect to said tube.

According to an aspect of a forty seventh and optionally according to any of the first to thirtieth and the fortieth to the forty sixth embodiments, there is provided a PEG device for conducting material through a stoma to or from a lumen comprising: a tube sized to bridge a channel between a lumen and an outer surface of a patient; an internal bolster, sized to resist movement out of the lumen through the stoma and connected to the tube; an external bolster, sized to resist movement into the stoma and connected to the tube; wherein the external bolster includes at least one element including an underside which extends from the tube in a radial direction and then towards the external bolster contacting the outer surface at a distance from an external opening of the stoma.

In some embodiments, said adjusting comprises:
 selecting an axial extent of a compressible element between an inner bolster and a lumen inner wall.

In some embodiments of the invention, said adjusting comprises:
 axially elastically deflecting a portion of said external bolster.

There is provided in accordance with some embodiments, a PEG feeding device for conducting fluid through a stoma to a stomach comprising:
 a tube sized to bridge a channel between a stomach and an outer abdominal surface;
 an external bolster, sized to resist movement into the stoma and connected to said tube; and a variable angle joint joining said external bolster to said tube and allowing said external bolster to tilt with respect said tube.

In some embodiments of the invention, the PEG further comprising:
an adjuster for setting a resistance of said external bolster to tilt with respect to an axis of said tube.

In some embodiments of the invention, the PEG further comprising:
at least one element including an underside which extends from said tube in a radial direction and then towards said external bolster contacting said outer abdominal surface at a distance from an external opening of said stoma.

In some embodiments of the invention, the PEG of claim 49, further comprising:
an internal bolster, sized to resist movement out of the stomach through the stoma and connected to said tube.

In some embodiments of the invention, the PEG further comprising:
an elastic biasing element biasing an angle of said tilting of said external bolster to a preferred angle.

There is provided in accordance with some embodiments, a PEG device for forming a channel through a stoma to a lumen comprising:
a tube sized to bridge a channel between the lumen and an outer abdominal surface;
an internal bolster, sized to resist movement out of the stomach through the stoma and connected to said tube; and
an external bolster, sized to resist movement into the stoma and connected to said tube;
wherein said external bolster includes at least one element including an underside which extends from said tube in a radial direction and then towards said external bolster contacting said outer abdominal surface at a distance from an external opening of said stoma.

There is provided in accordance with some embodiments, a method for draining the content of a stomach through a tube fixed between a stomach lumen and an abdominal opening, comprising:
inserting a replaceable inner tube with an expandable filter into said tube; and
draining food from said stomach lumen through said inner tube and said abdominal opening.

In some embodiments of the invention, the method further comprising:
monitoring the amount of said drained food after said draining.

In some embodiments of the invention, the method of claim 55, further comprising:
grinding the content of the stomach and/or the food within said replaceable inner tube during and/or before said draining.

There is provided in accordance with some embodiments, a device for draining the content of a stomach, comprising:
a tube, sized to bridge a channel between a stomach lumen and an outer abdominal surface;
an inner replaceable tube, sized to be placed within said tube, further comprising an expandable filter at the portion of said inner tube placed within said stomach lumen;
an inner body bolster and/or an outer body bolster configured to fix the position of said tube.

In some embodiments of the invention, said inner tube further comprises a grinder placed within the lumen of said inner tube, wherein said grinder is configured to reduce food particle size within said inner tube and/or within said stomach lumen.

In some embodiments of the invention, said inner tube further comprises a motor connector for connecting an outside motor to said grinder.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the figures generally, like components are indicated with like numerals, however, it should be noted that in some figures similar elements to those indicated in previous figures are provided with a new leading figure number.

In the drawings.

FIG. 5A is a simplified schematic of a patient with an installed ostomy device, and a feeding device, according to some embodiments of the invention;

FIG. 5B is a simplified schematic of a patient with an installed ostomy device, where a connector forms an ostomy device inner tube, according to some embodiments of the invention;

FIG. 6 is a simplified schematic of a feeding device where a connector is directly attached to a food reservoir, according to some embodiments, of the invention;

FIG. 7 is a simplified schematic of a feeding device where a connector, which includes a tube, is directly attached to a food reservoir, according to some embodiments, of the invention;

FIG. 12A is a simplified schematic cross sectional view of an inner tube before insertion into an outer tube which has accumulated residue, according to some embodiments of the invention;

FIG. 12B is a simplified schematic cross sectional view of an inner tube during insertion into an outer tube which has accumulated residue, according to some embodiments of the invention;

FIG. 13A is a simplified schematic cross sectional view of a portion of an ostomy device where an inner tube is disposed within an outer tube which has accumulated residue, according to some embodiments of the invention;

FIG. 13B is a simplified schematic cross sectional view of an inner tube during removal from an outer tube which has accumulated residue, according to some embodiments of the invention;

FIG. 14A is a simplified schematic cross sectional view of insertion of an inner tube including multiple cleaning elements into an outer tube, according to some embodiments of the invention;

FIG. 14B is a simplified schematic cross sectional view of an inner tube including multiple cleaning elements after exiting an outer tube, according to some embodiments of the invention;

FIG. 15A is a simplified schematic cross section of a bolster coupled to an inner tube by an elastic element, according to some embodiments of the invention;

FIG. 15B is a simplified schematic cross section of an inner tube released from an elastic element, according to some embodiments of the invention;

FIG. 27 is a simplified schematic cross section of an ostomy device with an adjustable tube length within the patient body, according to some embodiments of the invention;

FIG. 28A is a simplified schematic section view of a portion of an ostomy device, according to some embodiments of the invention;

FIGS. 28B-28D are simplified schematic cross sectional views of exemplary interlocking connection between external bolster and connector, according to some embodiments of the invention;

FIG. 36 is a simplified section view of a portion of an internal bolster including a tool channel for a dismantling tool, according to some embodiments of the invention;

FIG. 37A is a simplified schematic side view of an inner tube portion where inner tube is non-cylindrical, according to some embodiments of the invention;

FIG. 37B illustrates an inner tube portion including two channels, a feeding channel and a tool channel, according to some embodiments of the invention;

FIG. 38A is a simplified schematic section view of an internal bolster with a screw dismantling mechanism, according to some embodiments of the invention;

FIG. 38B is a simplified schematic side view of a screw dismantling mechanism tool 3868, according to some embodiments of the invention;

FIG. 39 is a simplified schematic of a portion of a bolster and an expanding dismantling tool, according to some embodiments of the invention;

FIG. 46A is a simplified schematic side view of a pushing device, according to some embodiments of the invention;

FIG. 46B is a simplified schematic side view of a pushing device within an outer tube attached to an internal bolster where a portion of the pushing device protrudes through the outer tube, according to some embodiments of the invention;

FIG. 47 is a simplified schematic side view of an ostomy device where an external bolster is being attached to an outer tube, according to some embodiments of the invention;

FIG. 48 is a simplified schematic section view of device installation including insertion of an outer tube into a stoma, according to some embodiments of the invention;

FIG. 49A is a simplified schematic cross sectional view of an inner bolster attached to an outer tube being inserted through an esophagus, according to some embodiments of the invention;

FIG. 49B is a simplified schematic cross sectional view of an inner bolster attached to an outer tube where the outer tube is installed within a stoma, according to some embodiments of the invention;

FIG. 49C is a simplified schematic section view of device installation including insertion of an outer tube into a stoma according to some embodiments of the invention;

FIG. 49D is a simplified schematic cross sectional view of a inner bolster connected to an outer tube being inserted through an esophagus, according to some embodiments of the invention;

FIGS. 56A-56C are perspective views of measurement sheaths and inserter needles in accordance with some embodiments of the current invention;

FIGS. 63A-63D are schematic views of an inner tube portion of an ostomy device, in accordance with some embodiments of the current invention;

FIGS. 64A-64E are schematic views of an external bolster of an ostomy device in accordance with some embodiments of the current invention;

FIGS. 65A-65B are schematic views of a high-profile ostomy device in accordance with some embodiments of the current invention;

FIG. 66C is a schematic illustration of a device for draining the content of a stomach inside the body in accordance with some embodiments of the current invention; and FIGS. 67A-67D are schematic views of an inner tube and a grinder of a device for draining the content of a stomach in accordance with some embodiments of the current invention.

DESCRIPTION OF SPECIFIC EMBODIMENTS OF THE INVENTION

The present invention, in some embodiments thereof, relates to ostomy devices and procedures and, more particularly, but not exclusively, to devices and procedures for percutaneous endoscopic gastronomy.

Overview

An aspect of some embodiments of the invention relates to an port device including an external and/or an internal bolster connected to a tube forming a channel through a stoma into a lumen (e.g. stomach) where one or both bolsters do not contact tissue and/or opening/s of the stoma.

For example, in some embodiments, an external bolster connected to the tube holds the tube by contacting a patient outer abdominal surface at an axial distance (e.g. distance from a long axis of the tube) from an opening of the stoma and/or from an opening of the tube. The opening of the stoma and/or the opening of the tube may optionally project from the abdominal outer surface and/or be on the abdominal outer surface. In some embodiments, the external bolster contacts the patient outer abdominal surface only at a separation from the opening of the stoma on the patient outer abdominal surface at a distance from the stoma of between 2-30 mm, between 5-25 mm, or between 5-15 mm, or smaller, or larger, or intermediate distances. In some embodiments, the external bolster mainly contacts the outer abdominal surface at a distance, where over 80%, or over 90%, or over 95%, or lower, or higher, or intermediate percentages, of a surface area of the external bolster contacting the outer abdominal surface is at a distance of between 2-30 mm, between 5-25 mm, or between 5-15 mm, or smaller, or larger, or intermediate distances.

Contact of the external bolster at a distance from the opening of the stoma prevents irritation and/or inflammation at the stoma opening from pressure applied to and/or movement of the external bolster.

In an exemplary embodiment, the ostomy device is a PEG feeding device, where fluid food and/or liquid are supplied directly to the stomach through the channel.

In some embodiments, an underside of the external bolster (e.g. facing the inner bolster e.g. a portion facing the tube), includes a shape that extends away from a long axis of the tube and towards the inner bolster (for example, an underside the external bolster is concave e.g. dome shaped).

Figure 2A:
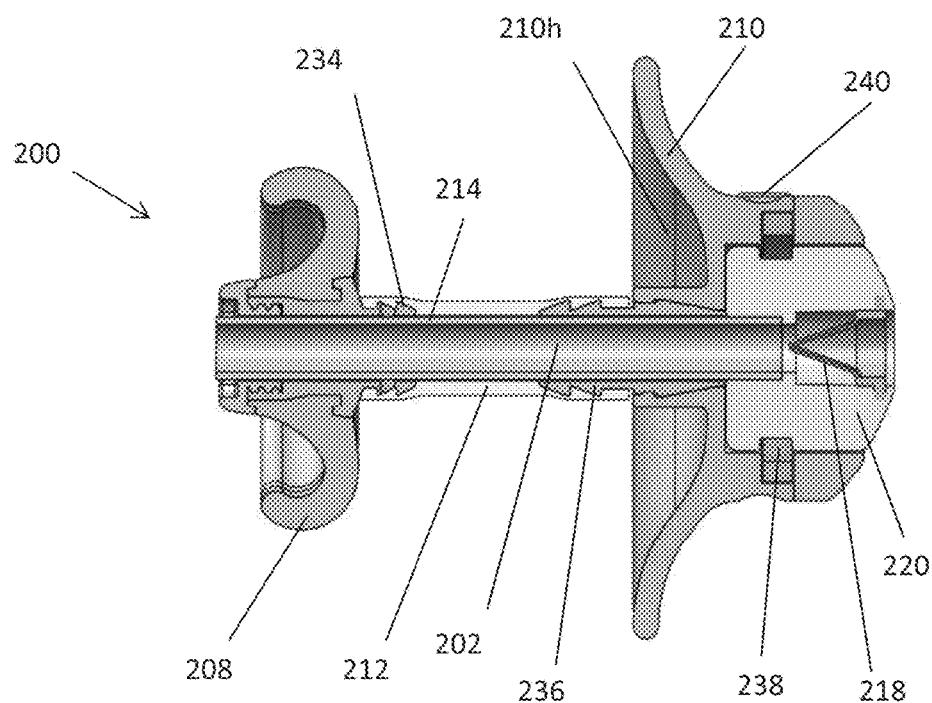
FIG. 2A is a simplified schematic sectional view of ostomy device including an inner tube, according to some embodiments of the invention.

In some embodiments, an underside of the external bolster includes one or more concave portion (e.g. hollow 210h, FIG. 2A). In some embodiments, an underside of the internal bolster includes one or more concave portion (e.g. hollow 3208h, FIG. 32A).

In some embodiments, the external bolster includes portions separated by spaces. In some embodiments, the external bolster contacts the outer abdominal surface at discrete points. In some embodiments, spaces between contacting points of the external bolster allow aeration and/or venting and/or facilitating cleaning of skin under the external bolster.

Optionally, the device includes an (optionally replaceable) inner tube (e.g. as described herein) disposed within the tube, where flow of material between the lumen and outside of the patient is through the inner tube. Optionally, the device includes soft and/or flexible inner bolster, for example, in some embodiments, the inner bolster is removable from the lumen through the stoma. For example, the inner bolster may be removed by pulling on the tube (directly or indirectly).

A broad aspect of some embodiments of the invention relates to an ostomy device with an adjustable axial length where, for example, a smallest separation between inner and external bolsters is adjustable. In some embodiments, the smallest separation between inner and external bolsters is adjustable by 5-30 mm.

In some embodiments, a device is installed within a patient by initially inserting a tube into a stoma where the tube is approximately sized for the stoma, for example, the tube is longer than the stoma. In some embodiments, a smallest separation between bolsters connected one on each end of the tube is adjusted, for example, fitting the device including an approximately sized tube to patient anatomy.

In some embodiments, adjustment is by moving a position of attachment of a bolster with respect to the tube, e.g. a position of an external bolster with respect to a connector connecting the external bolster to the tube.

In some embodiments, position of bolster/s is adjusted when the device is installed within a patient. In some embodiments, position of bolster/s is adjusted periodically for example, in response to a change in patient anatomy e.g. weight change and/or swelling.

In some embodiments, adjustment is through elasticity of one or more of the internal bolster, external bolster and tube, an axial length of the device thereby automatically adjusting to a range of lengths of stoma. In some embodiments, the tube includes a portion which is axially elastic. In some embodiments, one or more bolster includes a deflectable portion. Optionally the deflectable portion may be elastic. In some embodiments, one or more part elastically moves, changing a minimum separation between the bolsters. In some embodiments, a minimum separation between changes, fitting the device to the stoma, for example, during changes in stoma length, e.g. before, during and after post operative swelling of tissue around a stoma and/or patient weight gain and/or patient tissue change in fat percentage.

In some embodiments, a bolster (e.g. inner and/or external bolster) includes one or more portion which elastically bends and/or flexes. In some embodiments, the portion/s bend at pressures which are physiologically acceptable to patient tissue. For example, in some embodiments, a portion of a bolster in contact with patient tissue deflects before a pressure which causes damage and/or pain and/or discomfort to the patient tissue. In some embodiments, deflection of one or more elastic portion of a bolster changes a minimum axial separation between the bolsters. For example, in some embodiments, an elastic portion of a bolster extends towards the other bolster, a minimum separation between the bolsters defined from the elastic portion, deflection of the elastic portion changing the minimum separation between bolsters.

In some embodiments, the external bolster (and/or inner bolster) includes separate protrusions (e.g. petals) which, in some embodiments, elastically bend and/or flex and/or deflect independently (e.g. to different extents), for example, fitting the device to non-planar patient anatomy.

In some embodiments, the internal bolster includes inlets between separate parts (e.g. petals), for example allowing bending and/or flexing of the parts without overlapping of the parts.

In some embodiments, axial elasticity and/or flexibility of the internal bolster, where, for example, portion/s of the internal bolster bend under pressure (e.g. from the lumen walls), for example, bending towards an inner shaft of the internal bolster. In some embodiments, deflection of portion/s of the inner bolster prevents high pressure (e.g. associated with irritation of the lumen walls and/or the inner bolster becoming embedded in the lumen walls).

In an exemplary embodiment, the internal bumper includes portions (e.g. deflectable portions) with stiffness of 40-70 shore A, or 40-80 shore A, or 50-70 shore A, or lower, or higher, or intermediate stiffness.

In an exemplary embodiment, the internal bumper includes portions (e.g. deflectable portions) with stiffness of 40-70 shore A or 40-80 shore A, or 50-70 shore A, or lower, or higher, or intermediate stiffness.

In some embodiments, a force required to fully deflect deflectable portions of the external bumper is less than 10N, or less than 5N, or 1-10N.

In some embodiments, during delivery of the internal bolster through the esophagus to the stomach portion/s of the inner bolster bend and/or fold, optionally elastically, for example, reducing an extent of the inner bolster. In some embodiments, deflectable internal bolster portions have a maximum deflection, where, for example, in some embodiments, the internal bolster includes one or more blocking part which prevents bending beyond a maximum deflection.

In some embodiments, a spacer prevents the internal bolster from irritating the stomach wall, and/or for example, a compressible component (e.g. inflatable balloon, sponge, spring) placed (e.g. during installation of the ostomy device) between the internal bolster and the stomach.

In some embodiments, a spacer positioned between the inner bolster and lumen wall is adjusted from outside the body, for example, by pulling and/or releasing a component attached to the compressible component.

Optionally, in some embodiments, one or component deflects and/or extends non-elastically (e.g. plastically), for example, fitting the device to an expanding stoma.

Optionally, the device with adjustable axial length includes an (optionally replaceable) inner tube (e.g. as described herein) disposed within the tube, where flow of material between the lumen and outside of the patient is through the inner tube.

Optionally, the device with adjustable axial length includes soft and/or flexible inner bolster, for example, in some embodiments, the inner bolster is removable from the lumen through the stoma by pulling on the tube (directly or indirectly).

A broad aspect of some embodiments of the invention relates to an ostomy device including an outer tube and an inner tube, the inner tube forming a channel to a patient lumen. In some embodiments, the inner tube is removable for replacement and/or cleaning. In some embodiments, cleaning extends a life time of the ostomy device within the patient.

In some embodiments, the inner tube extends into the stomach. In some embodiments, the inner tube extends into the stomach and through the stomach to the jejunum, e.g. for feeding directly into the jejunum, the inner tube, being 1-30 cm long or 5-25 cm long, or shorter, or longer, or intermediate lengths or ranges.

In some embodiments, a seal (e.g. between the inner and outer tube) prevents flow within the outer tube around the inner tube.

An aspect of some embodiments of the invention relates to an inner tube which includes one or more protrusion where, for example, during insertion and/or removal of the inner tube from the outer tube, the protrusion/s contact the outer tube, for example, cleaning the outer tube.

Optionally, in some embodiments, the device including an inner tube includes soft and/or flexible inner bolster, for example, in some embodiments, the inner bolster is removable from the lumen through the stoma by pulling on the tube (directly or indirectly).

A broad aspect of some embodiments of the invention relates to an ostomy device including an internal bolster including a plurality of separate coupled parts. In some embodiments, the ostomy device is removed by decoupling the separate parts of the inner bolster to dismantle the inner bolster.

In some embodiments, the inner bolster includes a plurality of optionally flexible parts (herein termed petals) connected by optionally rigid connectors. In some embodiments, flexible petals are held between rigid connectors.

In an exemplary embodiment the petals substantially do not overlap. For example, the petals may substantially not overlap axially (overlap being where petals contact each other in a planes approximately perpendicular to the long axis of the tube). In some embodiments, petals at most overlap axially with adjacent (e.g. radially adjacent) petals.

In some embodiments, residue (e.g. stomach contents) coating the inner bolster (e.g. coating contact areas between petals) prevents and/or slows disassembly of inner bolster petals. In some embodiments, the inner bolster includes one or more notch and/or inlet separating portions of the inner bolster e.g. between petals. For example, reducing an area of contact between petals potentially reduces friction of movement of petals away from each other.

In some embodiments, the internal bolster includes a plurality of petals which are held by one or more connectors (e.g. in some embodiments, petals are held between two or more connectors) where disconnecting the connectors decouples the petals.

In some embodiments, the device includes a channel between an inner bolster dismantling mechanism and another portion of the device (e.g. the outer bolster). In some embodiments, the inner and/or outer tube forms the channel to the inner bolster. For example, in some embodiments, a user dismantles the inner bolster by accessing the internal bolster through the dismantling mechanism channel, from outside the patient (e.g. an endoscopic procedure is not required to dismantle the inner bolster).

In some embodiments, the inner bolster is dismantled by breaking at least a portion of a connector, for example, by applying pressure to the portion of the connector for example, applying pressure e.g. with a shaft. In some embodiments, the inner bolster is dismantled by moving and/or deflecting at least a portion of a connector, for example, moving an interlocking element, for example, by applying pressure e.g. with a shaft.

In some embodiments, pressure is applied by a non-designated tool, for example a hypodermic needle shaft or syringe.

In some embodiments, petals are coupled by a rotation attachment mechanism (e.g. screw mechanism, e.g. a mechanism with an open rotational configuration and a closed rotational configuration). In some embodiments, dismantling of the inner bolster includes rotating an inner bolster connector (e.g. unscrewing) to release petals of the inner bolster.

Optionally, the device with an inner bolster including a plurality of connected portions includes an (optionally replaceable) inner tube (e.g. as described herein) disposed within the tube, where flow of material between the lumen and outside of the patient is through the inner tube.

An aspect of some embodiments of the invention relates to an ostomy device where a flexible tube is connected to one or both bolsters by rigid connector/s. In some embodiments, a flexible tube is connected to a bolster including flexible part/s by connection (e.g. snap lock) of two rigid connector elements, one connected to the outer tube and the second to the flexible bolster.

In some embodiments, the tube has hardness of at least 40 shore A, or 50-80 shore A, or lower, or higher, or intermediate hardness. In some embodiments, the tube has a maximum radius of curvature of 1-25 mm, or 5-15 mm, or approximately 10 mm.

In some embodiments, a rigid connector is partially disposed within the flexible tube, for example, elasticity of the tube and/or a fitted friction fit of the connector holding the connector and tube together. In some embodiments, one or more connector is attached to the tube by injection molding the tube and connector as one part (optionally, where the connector includes different material to the tube). In some embodiments, one or more connector is attached to the tube by adhesion (e.g. gluing, heat treatment). In some embodiments, the tube is not folded around a connector.

In some embodiments, connection between the connector/s and the outer tube is non-smooth. For example, a diameter of the connector within the tube is less than a diameter of the tube, for example there is a step between the outer tube and the connector of 0.05 mm-1 mm, or 0.05 mm-0.5 mm, or lower, or higher, or intermediate values or ranges. In some embodiments, the inner tube prevents issues that would otherwise be associated with a non-smooth topography between the outer tube and the connector within the outer tube (e.g. build up of residue in the step).

Optionally, the device with adjustable axial length includes an (optionally replaceable) inner tube (e.g. as described herein) disposed within the flexible tube, where flow of material between the lumen and outside of the patient is through the inner tube.

Optionally, in some embodiments, the inner tube is flexible. In some embodiments, the inner tube has a maximum radius of curvature of 1-50 mm, or 5-25 mm, or approximately 20 mm.

In some embodiments, connection is to the flexible tube, which is non-smooth (e.g. stepped), while the flow of material to the lumen is through a smooth walled channel (e.g. the inner tube).

In some embodiments, the flexible inner tube (e.g. attached to rigid connector/s) includes a mesh of rigid material (e.g. within a sealing sheath) where free space within the mesh maintains tube flexibility.

An aspect of some embodiments of the invention relates to an ostomy device where a flexible tube is connected to one or both bolsters by a variable angle joint. For example, the variable joint may compensate for differences between the axis of the tube to the surface of the tissue and/or for changes and/or for movement of the surface. For example the angle of the joint may vary over a range of between 0 to 5 degrees and/or between 5 to 15 degrees and/or between 15 to 40 degrees and/or between 40 to 60 degrees. Optionally the bolster may float freely over the joint. Alternatively or additional the bolster may be biased to a particular angle (for example with the axis of bolster parallel and/or concentric to the axis of the tube and/or may be biased to one side for example to increase pressure on that side and/or decrease pressure on an opposite side).

In some embodiments, the tube may have a single unambiguous axis. For example the tube may be straight and/or have substantially the form of a right circular cylinder and/or have a-circular cross-section. In some embodiments, the tube may be curved and/or non-cylindrical and/or flexible and/or have a non-circular cross-section and/or may not have a single unambiguous axis. For the sake of the this disclosure, where the tube does not have a clearly defined unambiguous single longitudinal axis, the longitudinal axis of the tube will refer to a line joining the center of gravity of the cross section of the tube where it intersects the outer surface of the tissue (e.g. the outer surface of the abdomen of a patient) to the center of gravity of the cross section of the tube where it intersects the inner surface of the tissue (e.g. the inner surface of the stomach of the patient). An outer axis of the tube will refer to an axes perpendicular to the cross section of the tube and passing through the center of gravity of the cross section along a plane where the tube meets the outer surface of the tissue. An inner axis of the tube will refer to an axes perpendicular to the cross section of the tube and passing through the center of gravity of the cross section along a plane where the tube meets the outer surface of the tissue.

In some embodiments, the ostomy device is additionally or alternatively used to collect material (e.g. waste) from a lumen. For example, in some embodiments, the ostomy device is used to collect and/or release material from the stomach, optionally in addition to providing food to the stomach. In some embodiments, the ostomy device is used to reduce pressure within the stomach (e.g. by allowing material e.g. gas and/or food to escape through the device).

An aspect of some embodiments of the invention relates to measuring the depth from a base site to a location inside a living organism. For example the device may be used to measure a distance between two ends of a stoma and/or a port and/or a passageway into living tissue and/or a lumen of living organism. Optionally a marker (optionally including graduations) is inserted into the organism to the measurement location. For example, the marker may indicate a distance to a guide element. Optionally the guide element is placed at a base site. The marker may be positioned by viewing and/or sensing in the lumen. For example, placement of the marker may be without stressing the lumen tissue. The distance from the location in the organism to the base site is optionally measured by reading a graduation of the marker at the location inside the organism. For example, the method may be used to measure the length of a stoma and/or a port from an opening outside the lumen to an opening on the inner wall of the lumen.

An aspect of some embodiments of the invention relates to elastic distancers are sized and shaped to provide even pressure between a bolster and tissue of a subject over significant axial and/or rotational displacements. Optionally, an elastic element may have a form that distributes stresses evenly along the element. For example, the distance may have the shape of a petal. The distancer is optionally curved. For example the distance may be concave towards a tissue interface and/or concave away from the tissue interface.

Embodiments of this device may be included in various access ports to lumens or tissue. For example, a device may include a jejunal tube, for example in the form of a long inner tube passing through a stoma and/or a outer PEG access tube. The current invention may serve as an access port to another lumen, for example a thoracic cavity and/or a kidney and/or bladder.

An aspect of some embodiments relates to an internal bolster with at least a partially rigid core. In some embodiments, the internal bolster comprises a central shaft, optionally a rigid central shaft. In some embodiments, the central shaft hardness is at least 40 shore A, for example 50 shore A, 60 shore A, 70 shore A or 90 shore A, or intermediate, smaller or greater hardness. Alternatively, the central shaft is completely rigid or having a hardness level of 90 shore A and larger. In some embodiments, the internal bolster comprises at least two petals, connected to the central shaft. In some embodiments, at least some of the petals have a gradual increase in width or in cross-sectional geometry between the outer end of the petals in the circumference of the internal bolster and the inner end of the petals facing the central shaft. In some embodiments, the cross sectional geometry of inner end of the petals is at least 5% larger than the outer end of the petals, for example 15% larger, 20% larger or 50% larger, or intermediate, smaller or greater percentages. In some embodiments, the increase in width towards the inner end of the petals leads, for example to a gradual increase in rigidity. In some embodiments, the inner end of the petals is at least 10% more rigid compared to the outer end of the petals, for example 15% more rigid, 20% more rigid, 50% more rigid or 100% more rigid, or intermediate, smaller or greater percentages. Alternatively, the petals comprise a rigid section in the connection between the petals and the central rigid shaft, which is at least 10% more rigid than the rest of the petal, for example 10%, 20%, 30%, 50%, 100% or intermediate or smaller or greater percentages of increased rigidity.

In some embodiments, having an internal bolster with a central rigid shaft and/or at least some petals with an inner rigid section allows for example, to resist bending forces applied on the internal bolster, for example when the internal bolster passes through the esophagus. In some embodiments, the less rigid outer end of the petals allow the petals to bend and twist, while the more rigid inner end of the petals maintain the petals structure and the connection of the petals to the internal bolster during such travel. In some embodiments, the central rigid shaft is a flared shaft, with a wider diameter in the shaft ending placed within the stomach.

In some exemplary embodiments of the invention, additional rigidity is provided by geometrical changes and/or change sin processing of the material (e.g., polymer). Optionally or alternatively, rigidity and/or hardness are varied by mixing the material (e.g., polymer) with an additive (e.g., fibers) or by using a different material (e.g., a different polymer).

An aspect of some embodiments relates to a flared outer tube of an ostomy device. In some embodiments, the flared section of the outer tube is at least partially positioned within the stomach. In some embodiments, the flared section positioned at least partially within the body allows, for example to minimize the possibility of the tube to be pulled outside from the body by having a tube ending inside the stomach lumen that is wider than the stoma. In some embodiments, the diameter of the tube ending within the stomach is at least 4% larger than stoma diameter, for example 5%, 20%, 35% larger or intermediate or greater percentages.

A potential advantage of a flared shaft is avoiding sudden changes in tube diameter caused by the attachment of the inner bolster, which sudden changes might irritate tissue, for example, during tube retraction.

An aspect of some embodiments relates to connecting an ostomy device and a body with a stronger connection force compared to the connection of an external tube to the ostomy device. In some embodiments, the connection between an inner tube portion and an outer tube portion of an ostomy device is weaker than the connection between an external feeding tube and the inner tube portion. A potential advantage of having a weaker connection between the inner tube portion and an outer tube portion is, for example, ensuring that the ostomy device remains within the stomach while allowing detachment of a tube connected to the ostomy device, for example an external feeding tube. In some embodiments, the connection between the ostomy device and the body is at least 30% stronger, for example 75% stronger, 100% stronger, 2000% stronger, or intermediate or greater percentages, than the connection between the ostomy device and an external tube connected to the ostomy device. In some embodiments, the connection between the ostomy device and the body resists axial forces, for example axially forces pulling the ostomy device outside from the stomach. In some exemplary embodiments of the invention, the connection between the device and the body is exemplified by the inner bolster, e.g., its width not deforming under disconnect forces to allow the inner bolster to be pulled out of the stomach. In some exemplary embodiments of the invention, the connection is exemplified by the connection between the external bolster and the tube, such that retracting the feeding tube attached to the external bolster cannot disconnect the external bolster with a resulting possible ingress of the tube into the body.

An aspect of some embodiments relates to an ostomy device attached to the stomach and reaching into the small intestine. In some embodiments, an elongated inner tube is connected on one end to the inner portion of the ostomy device, and the other end of the elongated inner tube is placed within the small intestine, for example within the jejunum or in the duodenum. Alternatively, the inner tube portion comprises an elongated inner tube, for example to allow positioning of the inner tube end at the jejunum or in the duodenum. In some embodiments, the inner tube end is positioned, optionally using imaging techniques, in the jejunum or in the duodenum to allow, for example directly feeding into the small intestine. In some embodiments, the length of the elongated inner tube (e.g., the part designated to be inside of the inner bolster) is at least 5 cm, for example, 10, 20, 30 cm or shorter, intermediate or greater lengths. Optionally, when the inner tube is removed, the outer tube (e.g., the ostomy device) does not extend significantly (e.g., extends less than, for example, 2 cm or 1 cm) inwards of the stomach wall.

An aspect of some embodiments relates to an ostomy device with an elongated inner tube portion positioned above the stomach content level, for example for stomach decompression. In some embodiments, the inner tube end is positioned within the stomach above the stomach content level, for example to allow gas to exit through the inner tube portion. Optionally, the tube is pre-bent or a stylet is provided to bend the inner tube. Optionally, the inner tube is rotationally locked to the ostomy device so that rotation of such stylet (or insertion of a bent tube) can have a known reach direction in the stomach (e.g., above or below the ostomy device, as desired).

An aspect of some embodiments relates to draining the content of a stomach through a replaceable inner tube placed within a fixed ostomy device. In some embodiments, the inner tube comprises an expandable filter at the tube ending placed within the stomach. In some embodiments, the filter comprises openings or gaps that prevent food particles larger than, for example, 90% of the inner tube diameter to enter into the tube from the stomach lumen and potentially clog the tube and/or other parts of a food removal system.

In some embodiments, the ostomy device further comprises a grinder placed at least partly within the ostomy device. In some embodiments, the grinder is placed at least partially within an inner tube of the ostomy device. In some embodiments the grinder grinds the food that is found within the ostomy device. Optionally, the grinder grinds the food found within the inner tube. Alternatively or additionally, the grinder extends at least partially out from the tube into the stomach lumen, for example to grind food found within the stomach lumen.

In some embodiments, a motor is connected to the external part of the ostomy device. Optionally, the motor is connected to the grinder, for example to rotate the grinder. In some embodiments, rotating the grinder within the inner tube propels food out from the stomach.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Ostomy Device

Figure 1A:
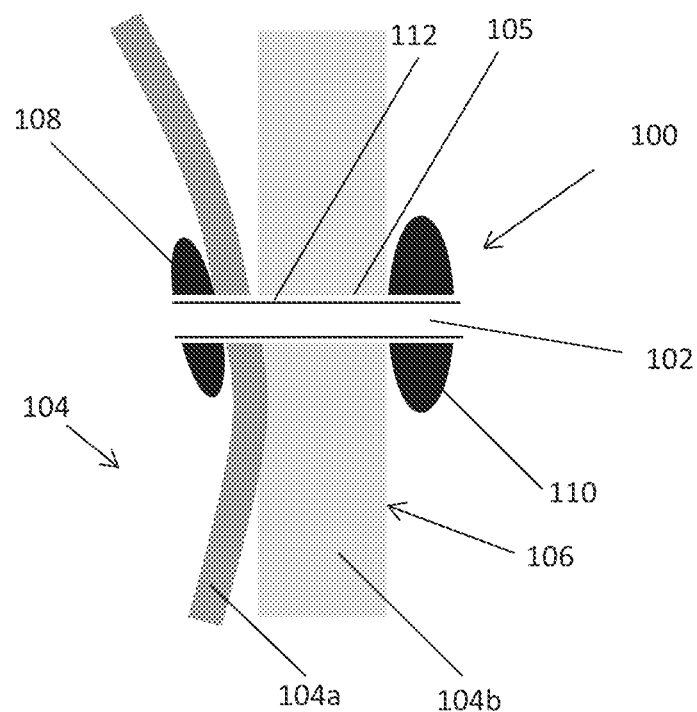
FIG. 1A is a simplified schematic cross section of an ostomy device which provides a channel between an internal patient lumen and an outer abdominal surface of the patient, according to some embodiments of the invention.

FIG. 1A is a simplified schematic cross section of an ostomy device 100 which provides a channel 102 between an internal patient lumen 104 and an outer abdominal surface of the patient 106, according to some embodiments of the invention.

In an exemplary embodiment, ostomy device 100 is a device for insertion during PEG, and lumen 104 is a patient stomach. In some embodiments, channel 102 passes through stomach wall 104a and abdominal wall 104b.

In some embodiments, tube 112 is at least partially disposed within a stoma 105 between lumen 104 and patient outer abdominal surface 106.

In some embodiments, ostomy device 100 includes an internal bolster 108 and an external bolster 110 which are each attached to tube 112. In some embodiments, bolsters 108 and 110 are attached at opposite ends of tube 112.

In some embodiments, inner bolster 108 is larger, in at least one direction perpendicular to an opening of the stoma within lumen 104, such that inner bolster 108 prevents tube 112 from falling out of stoma 105. In some embodiments, inner bolster 108 is larger, in at least one direction perpendicular to an opening of the stoma within outer abdominal surface 106, for example, preventing tube 112 from moving into the lumen.

Figure 1B:
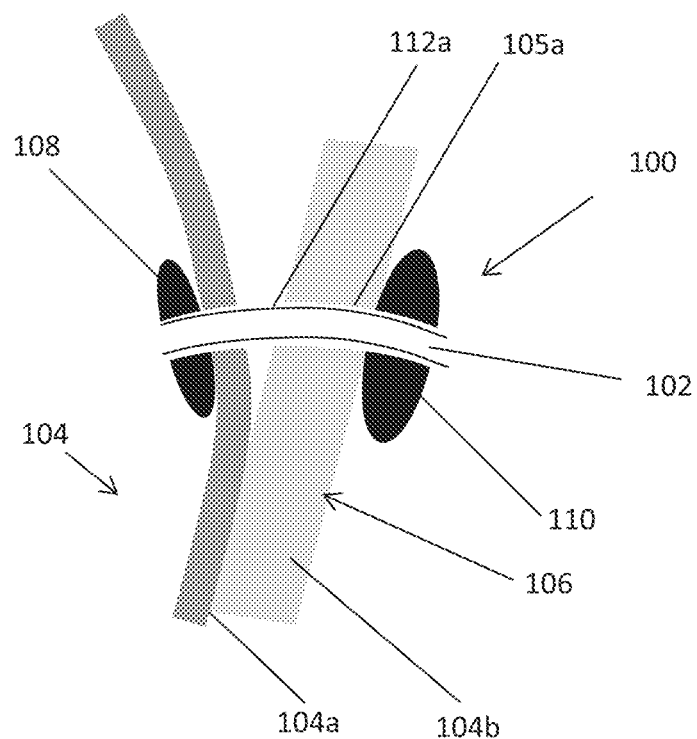
FIG. 1B is a simplified schematic cross section of an ostomy device with a flexible tube, according to some embodiments of the invention.

In some embodiments, stoma 105a does not follow a straight path between the lumen 104 and outer abdominal surface 106 (e.g. as illustrated in FIG. 1B). In some embodiments, the stoma is non-perpendicular to the lumen wall and/or outer abdominal surface. In some embodiments, a flexible tube (and/or bolster flexibility e.g. a described below) prevents pressure of the device on patient anatomy due to such non-planar patient anatomy. In some embodiments, one or more portions of the inner and/or outer bolster adjust to non-planar patient anatomy (e.g. as described below). In some embodiments, connection between the tube and the inner and/or outer bolster adjusts to non-planar patient anatomy.

FIG. 1B is a simplified schematic cross section of an ostomy device with a flexible tube 112a, according to some embodiments of the invention. In some embodiments, the patient moves without device 100 causing discomfort and/or injury, for example, due to tube 112 flexibility.

Inner Tube

In some embodiments, an ostomy device includes an inner tube providing a channel through which material passes e.g. from outside the patient into a patient lumen. FIG. 2A is a simplified schematic sectional view of ostomy device 200 including an inner tube 214, according to some embodiments of the invention. In some embodiments, ostomy device 200 is deployed in a patient where an internal bolster 208 is within a patient lumen (not illustrated) and an external bolster 210 is outside the patient and where an outer tube 212 and an inner tube 214 pass between the lumen and the outside of the patient e.g. as illustrated by tube 112 in FIG. 1A.

In some embodiments, inner tube 214 is disposed within outer tube 212 where inner tube 214 provides a channel 202 from outside a patient to a lumen (e.g. stomach).

In some embodiments, inner tube 214 and/or outer tube 212 are flexible, in some embodiments, bending of the outer tube causing the inner tube to bend, for example preventing stress between the two components and/or surrounding tissue. For example, preventing damaging stress (e.g. sufficient to cause necrosis) between outer tube 212 and In some embodiments, inner tube 214 is removable, for example, allowing cleaning of the inner and/or outer tube and/or replacement of inner tube 214.

In an exemplary embodiment, inner tube is sufficiently rigid for insertion of the inner tube 214 into the outer tube 212.

In an exemplary embodiment, inner tube 214 and/or outer tube 212 are sufficiently rigid (e.g. axially rigid) such that movement of the patient and/or movement of the outer bolster and/or pressure of patient tissue on the tubes do not cause buckling and/or collapse of outer tube 212 and/or inner tube 214. In some embodiments, inner tube 212 is sufficiently rigid to prevent closure of the channel, for example, due to pressure from patient tissue and/or collapse of the outer tube.

Figure 2B:
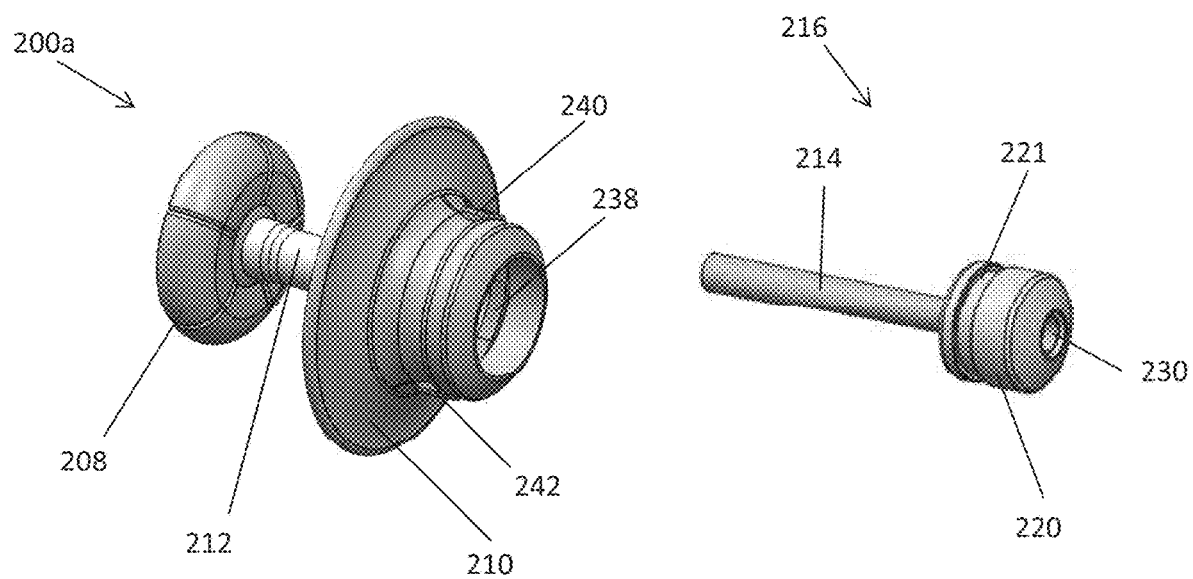
FIG. 2B is a simplified schematic side view of a ostomy device body and an inner tube portion, according to some embodiments of the invention.

In an exemplary embodiment, inner tube 112 is part of an inner tube portion which, in some embodiments, is removed and replaced or cleaned e.g. to provide a clean channel. FIG. 2B is a simplified schematic side view of an ostomy device body 200a and an inner tube portion 216, according to some embodiments of the invention. In some embodiments, ostomy device body 200a includes an internal bolster 208, an outer tube 212 and an external bolster 210.

Exemplary Method of Feeding

Figure 3:
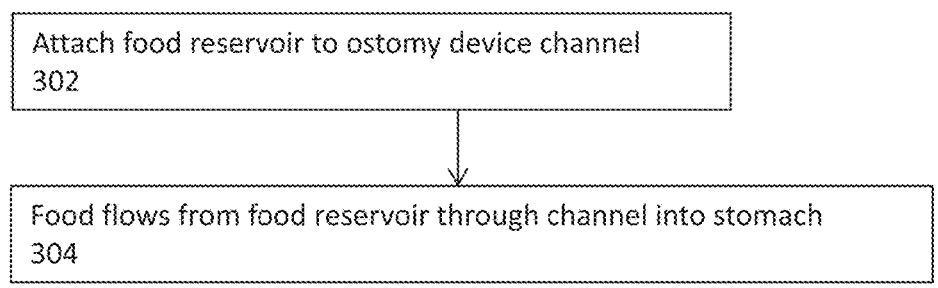
FIG. 3 is a flow diagram of a method of feeding, according to some embodiments of the invention.

FIG. 3 is a flow diagram of a method of feeding, according to some embodiments of the invention.

At 302, a food reservoir, for example, bag of fluid nutritional supplement, is attached to an ostomy device tube (e.g. inner tube 214). Exemplary contents of a food reservoir include liquid (e.g. water) and/or medication and/or any other substance desired for direct insertion into the stomach.

Figure 4A:
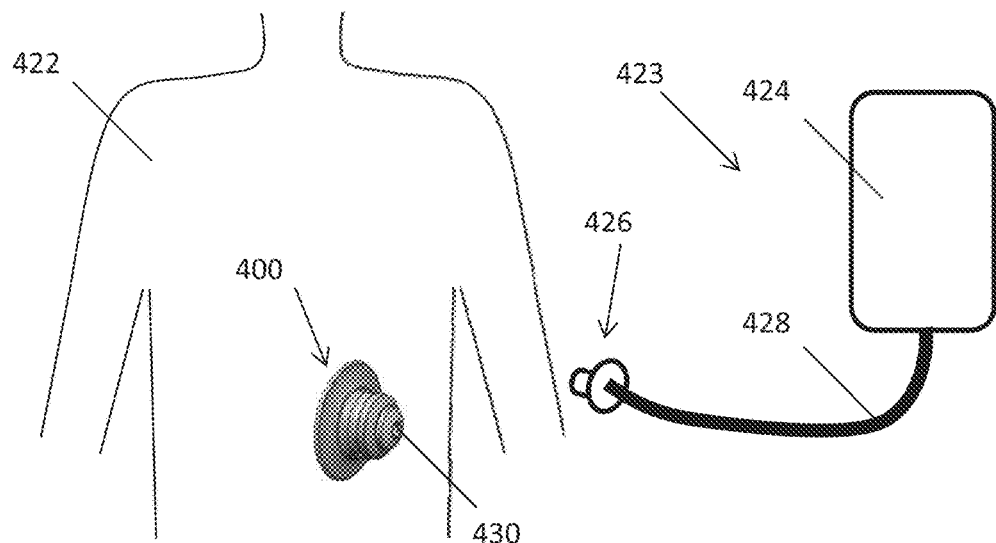
FIG. 4A is a simplified schematic of a patient with an installed ostomy device, and a feeding device, according to some embodiments of the invention.

FIG. 4A is a simplified schematic of a patient 422 with an installed ostomy device 400, and a feeding device 423, according to some embodiments of the invention. In some embodiments, feeding device 423 includes a food reservoir 424 and a connector 426.

Figure 4B:
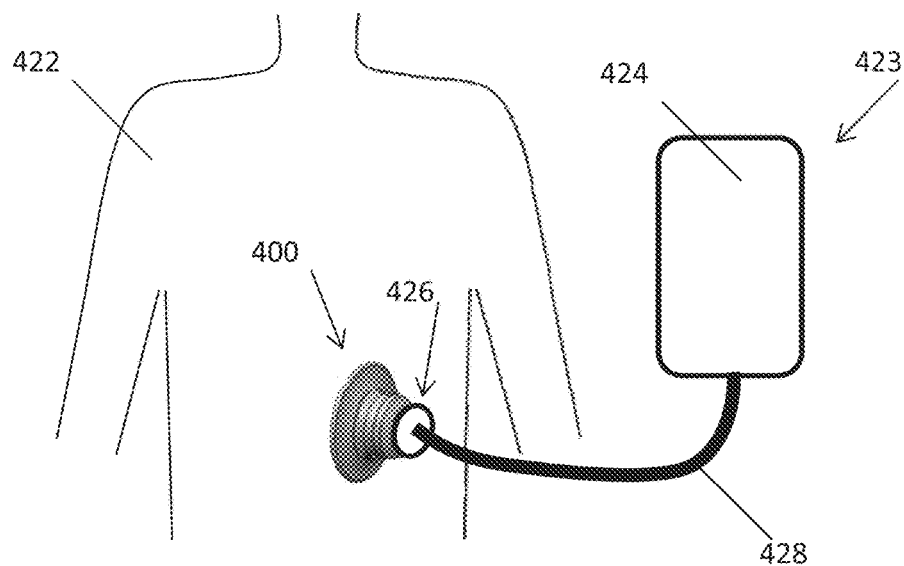
FIG. 4B is a simplified schematic of a patient with an installed ostomy device, where a feeding device is connected to ostomy device, according to some embodiments of the invention.

FIG. 4B is a simplified schematic of a patient 422 with an installed ostomy device 400, where a feeding device 423 is connected to ostomy device 400, according to some embodiments of the invention.

In some embodiments, food reservoir 424 is attached to an inlet 430 of an ostomy device tube (e.g. inner tube 214 illustrated in FIGS. 2A-2B) by connector 426. In some embodiments, connector 426 includes a pipe 428 through which food flows from food reservoir 424 into the patient 422. In some embodiments, connector 426 and/or fluid reservoir 424 and/or pipe 428 are commercially available components, used with PEG feeding devices.

In some embodiments, a feeding device includes a connector which is sized and shaped to fit into an ostomy device outer tube (e.g. outer tube 212), optionally forming a seal (e.g. as described herein). In some embodiments, the feeding device connector, when inserted into the ostomy device outer tube (e.g. outer tube 212) forms an inner tube of the ostomy device. FIG. 5A is a simplified schematic of a patient 522 with an installed ostomy device 500, and a feeding device 523, according to some embodiments of the invention. FIG. 5B is a simplified schematic of a patient 522 with an installed ostomy device 500, where a connector 526 forms an ostomy device inner tube, according to some embodiments of the invention. In some embodiments, connector 526 (which optionally includes a pipe 528) connects a food reservoir 524 to a patient stomach.

In some embodiments, a connector (for example connect 526 is configured to release when a dangerous force is applied to an external device (such as tube 528). For example when tube 528 is pulled with a force strong enough to pull ostomy device 400 out of a stoma, connector 526 releases tube 528. Optionally, tube 528 will be pulled away, but device 400 will remain in position.

In some embodiments, the method of feeding includes removing an inner tube portion (e.g. inner tube portion 216 illustrated in FIGS. 2A-2B) and then attaching a food reservoir to ostomy device 430.

In some embodiments, the connector is directly attached to the food reservoir (e.g. the feeding device does not include a tube). FIG. 6 is a simplified schematic of a feeding device 623 where a connector 626 is directly attached to a food reservoir 624, according to some embodiments, of the invention. FIG. 7 is a simplified schematic of a feeding device 723 where a connector 724, which includes a tube 714, is directly attached to a food reservoir 724, according to some embodiments, of the invention.

Returning back to FIG. 3, at 304, food (e.g. fluid food) flows from the food reservoir through a channel (e.g. channel 202) into the patient's stomach. In some embodiments, fluid flows into the stomach under gravity, for example the food reservoir is raised above height of the patient's stomach. In some embodiments, pressure is applied e.g. to the food reservoir, to dispense fluid into the stomach e.g. the fluid reservoir is a syringe, e.g. a patient or caregiver manually squeezes on the food reservoir.

In some embodiments, a feeding device (e.g. 423, 523, 626, 623) includes a feeding pump (e.g. a commercially available feeding pump) which regulates, for example, rate and/or quantity and/or pressure of fluid introduced into the patient through the ostomy device.

In some embodiments, once feeding is completed, the feeding device is removed, for example, from a body of the device, which remains in situ (e.g. partially within the patient, e.g. the inner tube is removed while the outer tube remains in position at least partially within the stoma).

In some embodiments, the inner tube is removed and cleaned or replaced periodically (e.g. every feed, once a day, once a week, once a month, or shorter, or longer, or intermediate time periods).

Inner Tube Portion

Exemplary Seal Between Inner Tube and Outer Tube

Returning back to FIGS. 2A-2B, in some embodiments, sealing between inner tube 214 and another part of the device prevents flow and/or material accumulating within tube 212 (e.g. outwards from the stomach) around inner tube 214. In some embodiments, sealing is of an opening into the lumen of the outer tube. In some embodiments, sealing is between inner tube 214 and outer tube 212. Alternatively, in some embodiments, sealing is between other parts preventing flow within the outer tube around the inner tube, for example, in some embodiments, sealing (e.g. a sealing element) is between the internal bolster (e.g. 208) and the inner tube (e.g. 214).

In some embodiments, e.g. as illustrated in FIGS. 2A-2B, inner tube 214 closely fits outer tube 212, preventing flow around inner tube 214.

In some embodiments, device 200 includes a sealing portion between inner tube 214 and outer tube 212.

Figure 8:
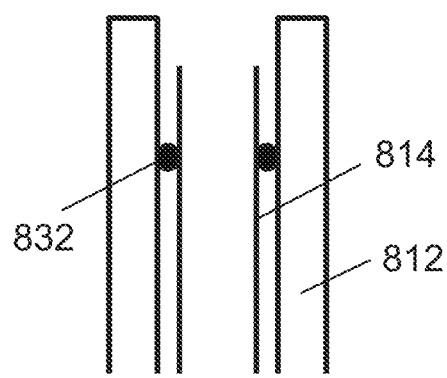
FIG. 8 is a simplified schematic cross sectional view of a tip of a portion of an ostomy device including a sealing element between an inner tube and an outer tube, according to some embodiments of the invention.

FIG. 8 is a simplified schematic cross sectional view of a tip of a portion of an ostomy device including a sealing element 832 between an inner tube 814 and an outer tube 812, according to some embodiments of the invention. In some embodiments, sealing element 832 is a ring of flexible material (e.g. rubber, silicone rubber) around inner tube 814. In some embodiments, sealing element 832 is mounted on (e.g. attached to) inner tube 814. Alternatively, in some embodiments, sealing element 832 is mounted on (e.g. attached to) outer tube 812.

In some embodiments, sealing is axial, for example, a seal between inner tube (e.g. 214) and outer tube (e.g. 214) is between a portion of the inner tube and a tip of the outer tube.

Figures 9A, 9B:
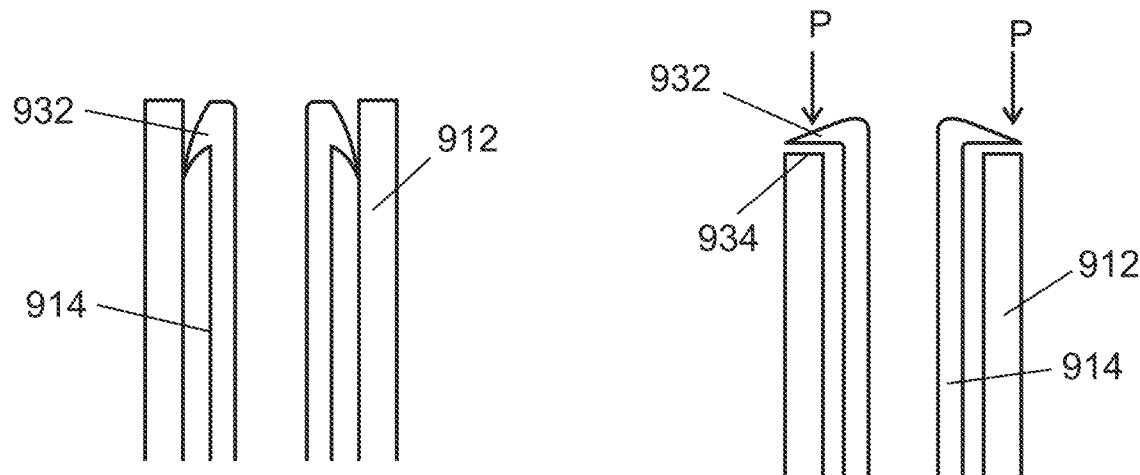
FIG. 9A is a simplified schematic cross sectional view of a portion of an ostomy device during insertion of an inner tube which includes an expanding sealing element, according to some embodiments of the invention.
FIG. 9B is a simplified schematic cross sectional view of a portion of an ostomy device and an expanded sealing element, according to some embodiments of the invention.

In some embodiments, axial sealing is achieved by the inner tube including an expanding sealing element (e.g. elastic and/or compressible and/or inflatable). FIG. 9A is a simplified schematic cross sectional view of a portion of an ostomy device during insertion of an inner tube 914 which includes an expanding sealing element 932, according to some embodiments of the invention. FIG. 9B is a simplified schematic cross sectional view of a portion of an ostomy device and an expanded sealing element 932, according to some embodiments of the invention. In some embodiments, once inner tube 914 is inserted such that expanding sealing element 932 emerges from the ostomy device (e.g. as described herein) outer tube 912, expanding sealing element 932 unfolds or expands to close, e.g. at the stomach end of outer tube 912, a channel between outer and inner tubes 912, 914. In some embodiments, sealing element 932 and a rim 934 of outer tube 912 are sized and shaped such that pressure P of stomach contents on sealing element 932 holds and/or pushes sealing element to rim 934 of outer tube 912, improving sealing.

Figures 10, 11:
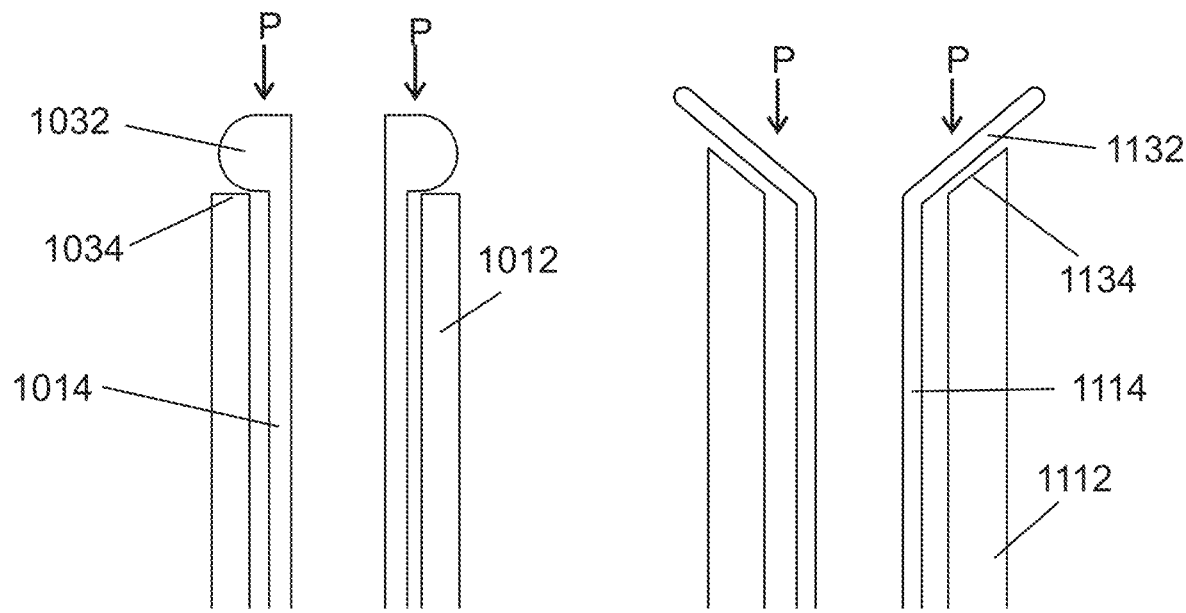
FIG. 10 is a simplified schematic of a portion of an ostomy device including a sealing element, according to some embodiments of the invention.
FIG. 11 is a simplified schematic of a portion of an ostomy device including a sealing element and an angled outer tube edge in contact with the sealing element, according to some embodiments of the invention.

FIG. 10 is a simplified schematic of a portion of an ostomy device including a sealing element 1032, according to some embodiments of the invention.

In some embodiments, a portion of the outer tube which in contact with the sealing element is sized and shaped to provide an increased surface area over which sealing occurs. FIG. 11 is a simplified schematic of a portion of an ostomy device including a sealing element 1132 and an angled outer tube edge 1134 in contact with the sealing element, according to some embodiments of the invention. The angled end of the outer tube, in contrast to a straight cut outer tube end, provides an increased contact area between the outer tube and the sealing element, and potentially a stronger seal associated with this larger surface area. In some embodiments, the angled end of the outer tube enables tube pull-out of the inner tube, for example, by facilitating retraction of the expanding portion of the inner tube.

In some embodiments, sealing element 1132 extends beyond outer tube 1112, the additional surface area under pressure from the stomach contents potentially increasing the force between sealing element 1132 and outer tube edge 1134.

In some embodiments, sealing is between walls of the outer and inner tube, e.g. as illustrated in FIG. 8 and FIG. 13A. Alternatively, or additionally, in some embodiments, sealing is between an edge or rim of the outer tube and the inner tube, e.g. as illustrated in FIG. 9B, FIG. 10 and FIG. 11. In some embodiments, sealing is between a surface of the outer tube and the inner tube, for example, in some embodiments, a sealing element wraps around and/or folds over the outer tube.

In some embodiments, a sealing element provides tactile feedback to a user that the inner tube portion is in position. For example, in some embodiments, the inner tube inserts freely until the sealing element engages, resistance of movement of the inner tube is increased.

Exemplary Inner Tube which Cleans Outer Tube

In some embodiments, the inner tube portion (e.g. 216) includes one or more portion for cleaning the outer tube, for example, on insertion and/or removal of the inner tube. In some embodiments, an inner tube sealing element also acts as a cleaning portion.

In some embodiments, a sealing element also cleans the outer tube, for example, on insertion and/or removal of the outer tube. For example, in some embodiment sealing element 832 (FIG. 8) is a cleaning and/or sealing element.

FIG. 12A is a simplified schematic cross sectional view of an inner tube 1214 before insertion into an outer tube which has accumulated residue 1236 (e.g. food residue), according to some embodiments of the invention. FIG. 12B is a simplified schematic cross sectional view of an inner tube 1214 during insertion into an outer tube which has accumulated residue 1236, according to some embodiments of the invention. FIG. 12B illustrates that residue 1236 has been cleaned from outer tube 1212, by cleaning portion 1232, and, in some embodiments, is removed from the ostomy device by pushing into the patient's stomach (e.g. if inner tube 1214 is inserted to a tip of outer tube 1212). In some embodiments, cleaning portion 1232 pushes against outer tube walls, potentially elasticity improving cleaning the outer tube (e.g. cleaning portion is elastic and is elastically compressed within outer tube). Flexibility and/or elasticity of cleaning element/s is illustrated by bending of cleaning elements 1432 in FIG. 14A.

FIG. 13A is a simplified schematic cross sectional view of a portion of an ostomy device where an inner tube 1314 is disposed within an outer tube 1312 which has accumulated residue 1336, according to some embodiments of the invention. FIG. 13B is a simplified schematic cross sectional view of an inner tube 1314 during removal from an outer tube 1312 which has accumulated residue 1336, according to some embodiments of the invention. FIG. 13B illustrates that residue 1336 has been cleaned from outer tube 1312. In some embodiments, residue 1336 is removed from the ostomy device during removal of inner tube 1314.

In some embodiments, an inner tube includes more than one cleaning element (and/or sealing element). FIG. 14A is a simplified schematic cross sectional view of insertion of an inner tube 1414 including multiple cleaning elements 1432 (which, in some embodiments are alternatively or additionally sealing elements) into an outer tube 1432, according to some embodiments of the invention. FIG. 14B is a simplified schematic cross sectional view of an inner tube 1414 including multiple cleaning elements 1432 after exiting an outer tube 1432, according to some embodiments of the invention.

Additionally or alternatively, in some embodiments, a cleaning device for example, including a cleaning element (e.g. as described above) is used to clean the outer tube. For example, the inner tube is removed; a cleaning tool is inserted and removed (optionally more than one time).

Exemplary Valve

Returning back to FIGS. 2A-2B, in some embodiments, ostomy device 200 includes one or more valve.

In an exemplary embodiment, a valve 218 is disposed in channel 202. In some embodiments, valve 218 is a one way valve, for example, allowing flow of food from a food reservoir to the stomach, but preventing back-flow from the stomach outwards. Alternatively, in some embodiments, valve 218 is a one way valve, allowing flow from the lumen out of the ostomy device, but preventing flow into the lumen. In some embodiments, valve 218 is a two directional valve, for example, which allows flow into the lumen of fluid and prevents flow in the opposite direction, below a certain pressure, once reached valve 218 allows flow out of the lumen (e.g. providing venting of the lumen potentially preventing pressure build up in the lumen).

In some embodiments, channel is connected to a component including two branches, each including a valve. For example, in some embodiments, a first valve, disposed in a first branch is a one way valve only allowing movement of material into the valve. In some embodiments, a second valve, disposed in a second branch is a one way valve only allowing movement of material out of the valve e.g. once a threshold pressure is exceeded.

In some embodiments, the ostomy device (e.g. as described herein) is used to depressurize the stomach, continuously and/or periodically, e.g. by allowing flow of material out of the stomach e.g. gas and/or other stomach contents.

In some embodiments, valve 218 remains closed until a feeding device (e.g. 423, 523) is attached to ostomy device 200, the attachment of which, in some embodiments, opens valve 218. Alternatively or additionally, in some embodiments, ostomy device 200 includes a closing element for example, a plug which is inserted into and/or over outlet 230 between feeds. For example, plug 3772 illustrated in FIG. 37A.

In an exemplary embodiment, valve 218 is located within head 220.

Exemplary Coupling of Inner Tube to Body of Ostomy Device

In some embodiments, inner tube 214 is attached at one or more point to one or more portion of a body of the ostomy device 200, for example, preventing movement of the inner tube.

For example, as described previously, in some embodiments, inner tube 214 is coupled (e.g. to outer tube 212 and/or to internal bolster 208) by a sealing element, e.g. the inner tube is coupled to the outer tube by a sealing element (e.g. as illustrated in FIGS. 8, 9A-9B, 10 and 11).

In some embodiments, an inner tube portion 216 includes inner tube 214 and a head 220 which attaches to external bolster 210. In some embodiments head 220 is rigid. In some embodiments, head 220 is larger in a direction perpendicular to a long axis of the inner tube, providing a larger surface area for attachment to external bolster 210 and/or for attachment to a feeding device. In some embodiments inner tube portion 216 including inner tube 214 and head 220 is a single piece (e.g. molded as a single piece and/or assembled by connecting tube 214 and head 230). For example, some embodiments, inner tube 214 and head 220 are formed of the same material (e.g. silicone and/or polyurethane), where inner tube 214 (e.g. due to thickness of walls of the inner tube) is flexible and head 220 is a substantially rigid part (e.g. due to thickness of material in the part), for example forming a stable connector to other portions e.g. external bolster 220 and/or a feeding device.

In some embodiments, connection of the inner tube is by connection of the inner tube both at a lumen end of the inner tube (e.g. by a sealing element) and by connection of the inner tube (or inner tube portion) to the external bolster.

In an exemplary embodiment, a sealing ring is disposed in a ridge between the outer tube and a connector connecting the outer tube to a bolster (e.g. the inner bolster). In some embodiments, a connector connecting the outer tube to a bolster (e.g. the inner bolster) itself forms a sealing element against the inner tube.

In some embodiments, inner tube 214 is coupled to external bolster 210. In some embodiments, an elastic element couples an inner tube portion (e.g. 216) to an external bolster (e.g. 210). FIG. 15A is a simplified schematic cross section of a bolster 1510 coupled to an inner tube by an elastic element 1538, according to some embodiments of the invention. FIG. 15B is a simplified schematic cross section of an inner tube released from an elastic element 1538, according to some embodiments of the invention.

In some embodiments, elastic element 1538 is relaxed when an elastic element cross section smallest dimension, D, is larger than the diameter (D1) of inner tube portion 216, such that, when inner tube portion 216 is disposed inside elastic element 1538 (e.g. as illustrated in FIG. 15A) the elastic element holds the inner tube portion (with elastic element cross section smallest dimension D1>D). To remove inner tube portion 216, in some embodiments, buttons 1540, 1542 are pushed inwards by pressure, P (e.g. applied by a user) which deforms elastic element 1538 into a shape (e.g. a more circular shape) with larger cross section smallest dimension, D2. Elastic element 1538 no longer holds inner tube portion 1516 and, in some embodiments, inner tube portion 1516 is free to be removed.

In some embodiments, elastic element 1538 holds the inner tube itself (e.g. 214 as illustrated in FIGS. 2A-2B). Alternatively, in some embodiments, elastic element 1538 holds an element connected to the inner tube (e.g. head 220 as illustrated in FIGS. 2A-2B).

In some embodiments, elastic element 1538 holds inner tube portion 1516 in an inlet of inner tube portion 1516. Returning back to FIG. 2B, in an exemplary embodiment, an elastic element 238, when inner tube portion 216 is inserted into the body of ostomy device 200, is located within a groove 221 in the inner tube portion.

Figure 16:
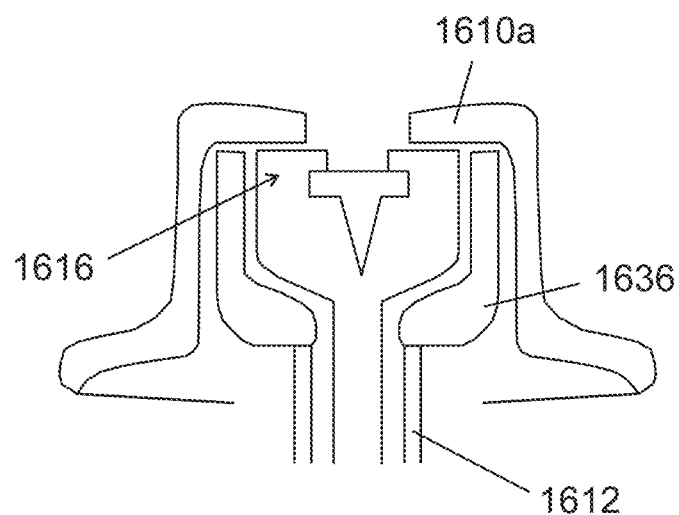
FIG. 16 is a simplified section view of an external bolster fitting over an inner tube portion, according to some embodiments of the invention.

In some embodiments, an inner tube portion is held in position by an external bolster including two portions, a first external bolster portion fitting over the inner tube portion (e.g. overlaps axially inner tube portion head 220). FIG. 16 is a simplified section view of an external bolster including a portion 1610a which fits over an inner tube portion 1616, according to some embodiments of the invention. In some embodiments, external bolster 1610 holds inner tube portion 1616 against the outer tube 1612. In some embodiments, external bolster 1610 is a flexible component which elastically holds inner tube portion 1616 onto an external bolster second portion 1636 attached to an outer tube 1612. In some embodiments, when inner tube portion 1616 is removed and/or replaced, external bolster 1610 is detached and/or a portion of the external bolster which holds inner tube portion 1616 is moved.

In some embodiments, first external bolster portion 1610a is an axially flexible portion, (e.g. as described herein) and second external bolster portion 1636 is sized to prevent movement into the stoma.

In some embodiments, an inner tube portion attaches to an external bolster by a protruding portion of the inner tube portion plugging into a hollow (also herein termed recess) in the external bolster (e.g. a plug-socket mechanism). In some embodiments, more than one protrusion plugs, each protrusion into a matching hollow or recess. Alternatively, in some embodiments, the inner tube portion includes one or more recess and the external bolster includes matching plug/s.

In some embodiments, one or more part of an inner tube plug is elastic, holding the inner tube plug in position within a bolster socket, for example, inner tube plug includes a by an interference mechanism (e.g. push-lock mechanism).

Figure 17:
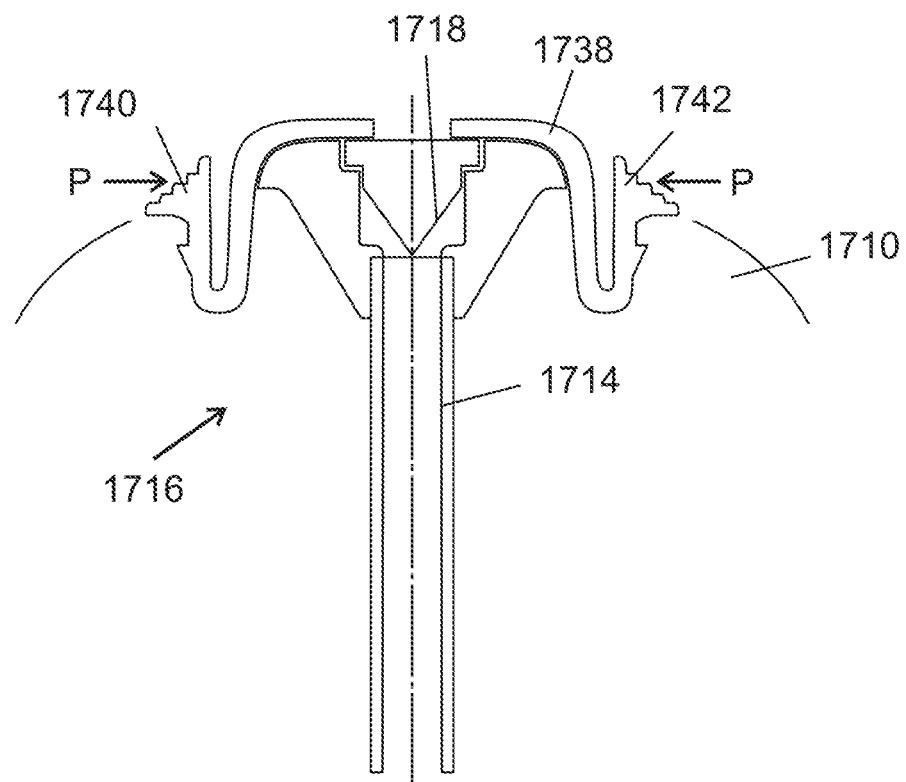
FIG. 17 is a simplified schematic cross sectional view of a connection between an inner tube portion and an external bolster, according to some embodiments of the invention.
Figure 33:
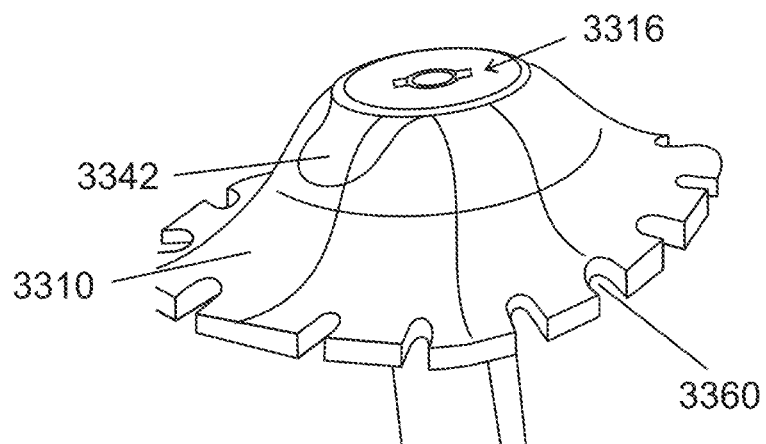
FIG. 33 is a simplified schematic isometric view of an external bolster including a plurality of notches 3360, according to some embodiments of the invention.

In some embodiments, an inner tube portion is held in position by an interference mechanism (e.g. push-lock mechanism). FIG. 17 is a simplified schematic cross sectional view of a connection between an inner tube portion 1716 and an external bolster 1710, according to some embodiments of the invention. In some embodiments, as inner tube portion 1716 is pushed into an outer tube (not illustrated) protrusions of the inner tube portion enter into hollows in the external bolster, elastic portions of the inner tube portion 1740, 1742 and/or interlocking shape of the hollows and protrusions holding inner tube portion and external bolster together (e.g. by an interference mechanism (e.g. push-lock mechanism)). FIG. 33 illustrates a side view of the inner tube portion illustrated in FIG. 17, 1716 inserted into an external bolster 3310. In some embodiments, a user pushes, P on inner tube portion 1740, 1742, separating at least some inner tube portion and external bolster interlocking portion/s to free the inner tube portion.

Figure 18A:
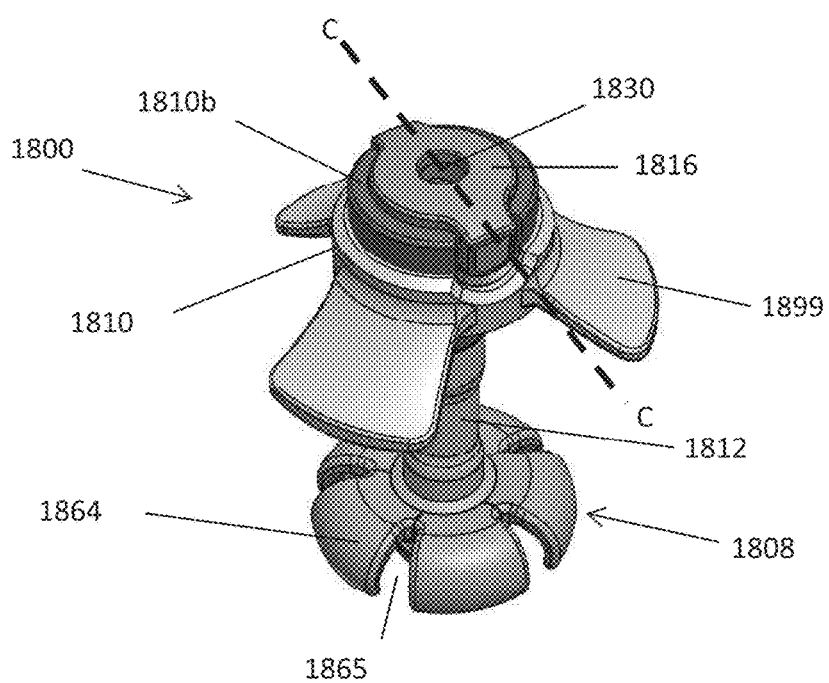
FIG. 18A is a simplified schematic isometric view of an ostomy device including a plug-socket connection between an inner tube portion and an rigid connector, according to some embodiments of the invention.

In some embodiments, inner tube portion is connected indirectly to the external bolster by connection to a rigid connector. FIG. 18A is a simplified isometric view of an ostomy device 1800 including a plug-socket connection between an inner tube portion 1816 and an rigid connector 1810b, according to some embodiments of the invention.

Figure 18B:
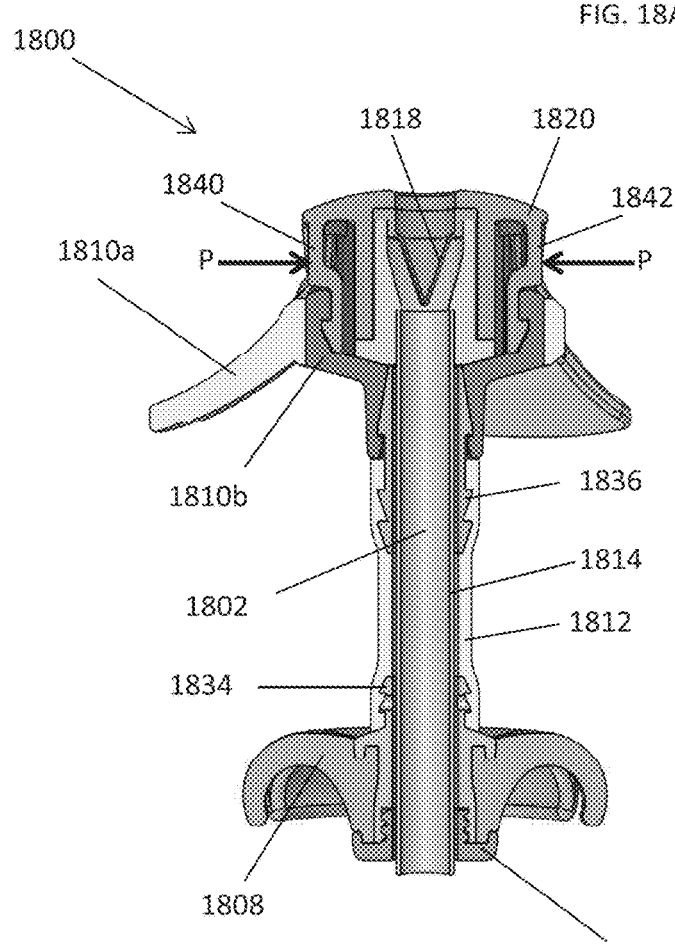
FIG. 18B is a simplified schematic section view of an ostomy device including a plug-socket connection between an inner tube portion and a rigid connector, according to some embodiments of the invention.

FIG. 18B is a simplified schematic section view of an ostomy device 1800 including a plug-socket connection between an inner tube portion 1816 and an rigid connector

1810*b*, according to some embodiments of the invention. FIG. 18B illustrates the section taken along line C-C in FIG. 18A.

Figure 18C:
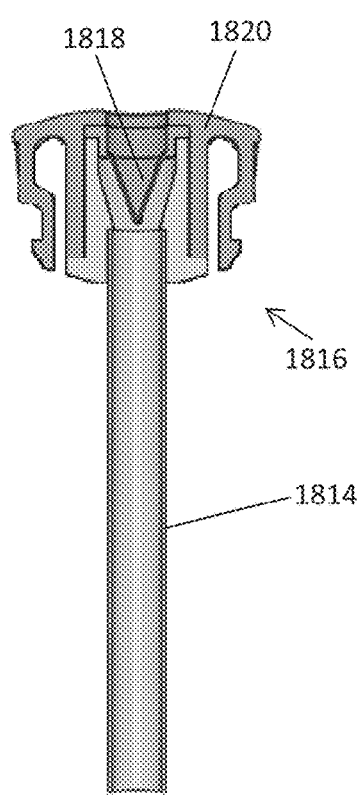
FIG. 18C is a simplified schematic section view of an ostomy device inner tube portion including a plug connector, according to some embodiments of the invention.

FIG. 18C is a simplified schematic section view of an ostomy device inner tube portion 1816 including a plug connector, according to some embodiments of the invention.

In some embodiments, rigid connector 1810*b* forms a base for connection of flexible devices, for example, external bolster 1810 and/or outer tube 1812 and/or inner tube 1814 (connected via inner tube head 1820). In some embodiments, inner tube portion 1816 is held in position by a by an interference mechanism (e.g. push-lock mechanism) where elements of head 1820 interlock with elements of connector 1810*b*. In some embodiments, a user pushes, P on inner tube portion buttons 1840, 1842, separating at least some inner tube portion and external bolster interlocking portion/s to remove the inner tube portion from the device.

In some embodiments, the connection between the inner tube portion and the external bolster is shaped such that, upon release of the inner tube portion (e.g. by pressing on buttons 1840, 1842) the inner tube portion moves outwards (e.g. partially) from the inner tube portion.

In some embodiment, removal of the inner tube portion includes releasing a connection between the inner tube portion and the external bolster (e.g. pressing on one or more button (e.g. pressing concurrently on two buttons)). In some embodiments, release of the inner tube portion is followed by pulling on the inner tube portion to remove it from the body of the ostomy device. In some embodiments, release and removal of the inner tube portion is performed concurrently e.g. release of the inner tube portion from connection with the external bolster includes pulling on the inner tube portion.

In some embodiments, a connector for to an ostomy device is designed to release when a high tension is applied. For example if a inner tube portion is pulled with a force hard enough to pull an inner bolster out of a stoma, connector 1810*b* is configured to release so that inner tube is pulled out of the outer tube, but the outer tube and bolsters remain in place in the stoma. For example, the maximum force before the tube is release may range between 5 to 10 N and/or between 10 to 20 N and/or between to 50 N and/or between 50 to 100N.

In some embodiments, a connector is resistant to twisting forces. For example since inner tube portion 1816 is not connected to ostomy device 1800 by a threaded connector, twisting tube portion 1816 will not cause it to be disconnected.

Exemplary Anti-Rotation

In some embodiments, one or more part of an ostomy device (e.g. 200, 1800, as described herein) includes anti-rotation feature/s to prevent rotation of parts of the device with respect to each other.

In some embodiments, anti rotation feature/s ensure that torque applied to a part of the device transfers axially along the device. For example, in some embodiments, rotating external portion/s of the device (e.g. external bolster) causes internal portions of the device (e.g. inner bolster and/or outer tube) to rotate.

In some embodiments, an inner bolster is rotated periodically (e.g. by rotating the outer bolster), for example, as part of a care protocol, e.g. to prevent encapsulation of the inner bolster into the stomach wall.

In some embodiments, anti-rotation element/s facilitate attachment of feeding device connector/s via rotation, for example, in some embodiments, attachment of a feeding device to an inner tube by rotation (e.g. screw attachment) is assisted by lack of rotation of the inner tube within the device.

In some embodiments, one or more anti-rotation element prevents rotation of the inner tube within the device.

In some embodiments, one or more anti-rotation element prevents rotation of one or more bolster with respect to the outer tube.

In some embodiments, rotation of inner tube portion 216 with respect to the ostomy device body and/or external bolster 210 is prevented by anti-rotation elements on inner tube portion 216 and/or external bolster 210. In some embodiments, lack of rotation of the inner tube portion prevents twisting and/or tangling (e.g. associated with constricted flow and/or loosening of attachment of the feeding device) of portions of a feeding device attached to the ostomy device (e.g. twisting and/or tangling of feeding device tube 428, 528 closing and/or collapsing the tube).

In some embodiments, one or more part of an ostomy device (e.g. 200, 1800, as described herein) includes anti-rotation features to prevent rotation of the inner tube within a body of the ostomy device (body of the device including internal bolster, outer tube and external bolster).

Returning back to FIG. 15A and FIG. 15B protrusions 1544, 1546 of or connected to elastic element 1538 fit within indentations 1548, 1550 respectively hold elastic element 1538 in axial and/or rotational position, e.g. preventing rotation of external bolster 1510 and inner tube portion 1520 with respect to each other. Additionally or alternatively, in some embodiments, protrusions 1544, 1546 and indentations 1548, 1550 prevent movement and/or slipping of elastic element with respect to external bolster 1510, e.g. during insertion and/or removal of inner tube portion 1516.

In some embodiments, at least a portion of buttons 1530, 1542, fit through holes in external bolster 1510. In some embodiments, buttons 1530, 1542, additionally or alternatively prevent rotation external bolster 1510 and inner tube portion 1520 with respect to each other.

Figure 20A:
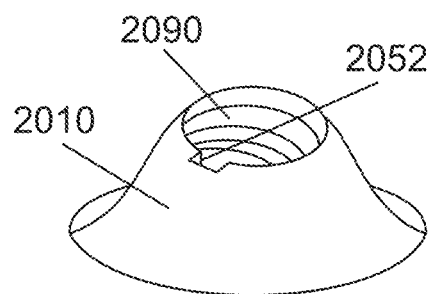
FIG. 20A is a simplified schematic of an external bolster including a hollow, according to some embodiments of the invention.
Figure 20B:
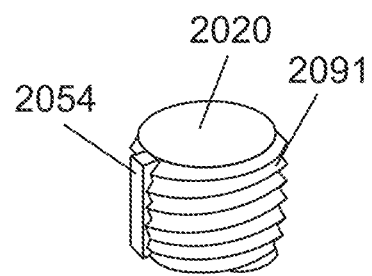
FIG. 20B is a simplified schematic of an inner tube portion head including a protrusion, according to some embodiments of the invention.

In some embodiments, anti-rotation elements include interlocking elements. FIG. 20A is a simplified schematic of an external bolster 2010 including a hollow 2052, according to some embodiments of the invention. FIG. 20B is a simplified schematic of an inner tube portion head 2020 including a protrusion 2054, according to some embodiments of the invention. When inner tube portion head 2020 is within external bolster, protrusion 2054 fits within hollow 2052 preventing rotation of inter tube portion head 2020 with respect to external bolster 2010.

Figure 21:
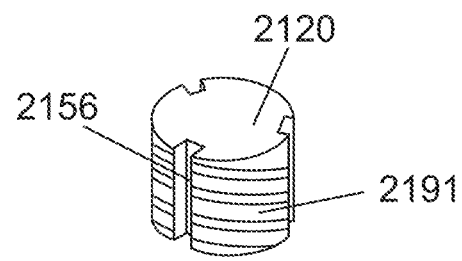
FIG. 21 is a simplified schematic side view of an inner tube portion head including more than one hollow, according to some embodiments of the invention.

In some embodiments, connected portions include more than one interlocking element. In some embodiments an external bolster includes protrusions and the inner tube portion includes hollows. FIG. 21 is a simplified schematic side view of an inner tube portion head 2120 including more than one hollow 2156, according to some embodiments of the invention. In some embodiments, each of a pair of connected pieces includes both hollows and protrusions.

Figure 19:
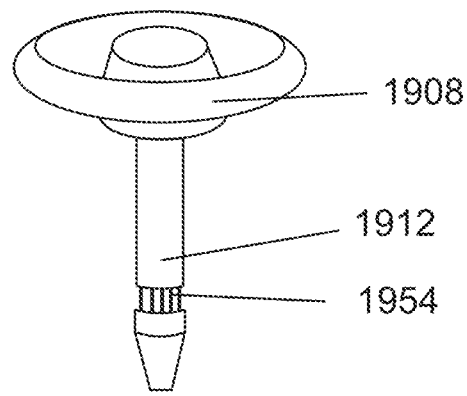
FIG. 19 is a simplified schematic of an outer tube including anti-rotation elements, according to some embodiments of the invention.

In some embodiments, connection between an outer tube (e.g. 212) and a bolster include anti-rotation element/s, for example texture and/or interlocking elements. FIG. 19 is a simplified schematic of an outer tube 1912 including anti-rotation elements 1954, according to some embodiments of the invention. In some embodiments, anti-rotation elements 1952 are serrations on an outer surface of outer tube 1912 and/or on an outer surface of a connector attached to the outer tube. Alternatively or additionally, in some embodiments, a bolster and/or or connector attached to a bolster includes anti rotation elements, e.g. serrations shaped to interlock with serrations 1954.

Other anti-rotation mechanisms on connecting portions, for example connection between bolster/s and the outer tube and connection of the inner tube to bolster/s and/or the outer tube are envisioned and encompassed by the present invention. For example, matching hollows/protrusions and/or other anti-rotation shapes such as non cylindrical cross section, e.g. triangular, square, octagonal, oval.

Exemplary Connection of Flexible Parts

In some embodiments, a device outer tube (e.g. 112) is flexible and/or portion/s of an internal bolster and external bolster are flexible (e.g. as described herein).

In some embodiments, bolsters (e.g. 108, 110) are connected to tube 112, where connection between the bolsters and the tube is sufficiently strong such that movement of the patient and/or connection and disconnection of a feeding device (e.g. 423, 523, 623, 723) do not cause loosening and/or disassembly of bolsters 108, 110 from tube 112.

In some embodiments, secure connection of flexible components is using rigid connectors.

In some embodiments, flexible portion/s of each bolster (e.g. 208, 210) are connected to a flexible outer tube (e.g. 212) by one or more rigid connecting element (e.g. 234, 236).

In some embodiments, more than one (optionally rigid) connecting element is used to connect two parts (e.g. flexible parts) where a first connecting element connects to a first flexible part (e.g. a bolster), a second connecting element connects to a second flexible part (e.g. an outer tube) and the connecting elements then connect together (e.g. with a snap lock mechanism, e.g. with a screw mechanism).

In some embodiments, a connection between a bolster (e.g. 208, 210) and the outer tube (e.g. 212) includes a first rigid connecting element attached to the outer tube which attaches to a second rigid connecting element attached to the bolster. For example, referring to FIGS. 2A-2B, connecting element 236 attached to the inner tube connects.

In some embodiments, one or more connector attaches to a bolster with a snap lock connection for example, as illustrated by connection between connector 234 and external bolster 210.

In an exemplary embodiment, connector 234 is permanently connected to internal bolster 208, for example by injection molding and/or adhesion (e.g. by gluing). Alternatively, in some embodiments, connector 234 and internal bolster 208 are one part. In some embodiments, internal bolster 208 and outer tube 212 are one part.

In another exemplary embodiment, connector 236 is permanently connected to external bolster 210, for example by injection molding and/or adhesion (e.g. by gluing). Alternatively, in some embodiments, connector 236 and external bolster 210 are one part. Alternatively, in some embodiments, internal bolster 210 and outer tube 212 are one part.

In some embodiments, a same material is used to form both rigid and flexible parts. For example, in some embodiments, a single material component including a flexible bolster and a rigid connector (e.g. molded as one piece) where the bolster is sized such that it is flexible and the connector is sized such that it is rigid. For example, in some embodiments, flexible inner bolster 208 and rigid connecter 234 are one molded part.

Figure 22:
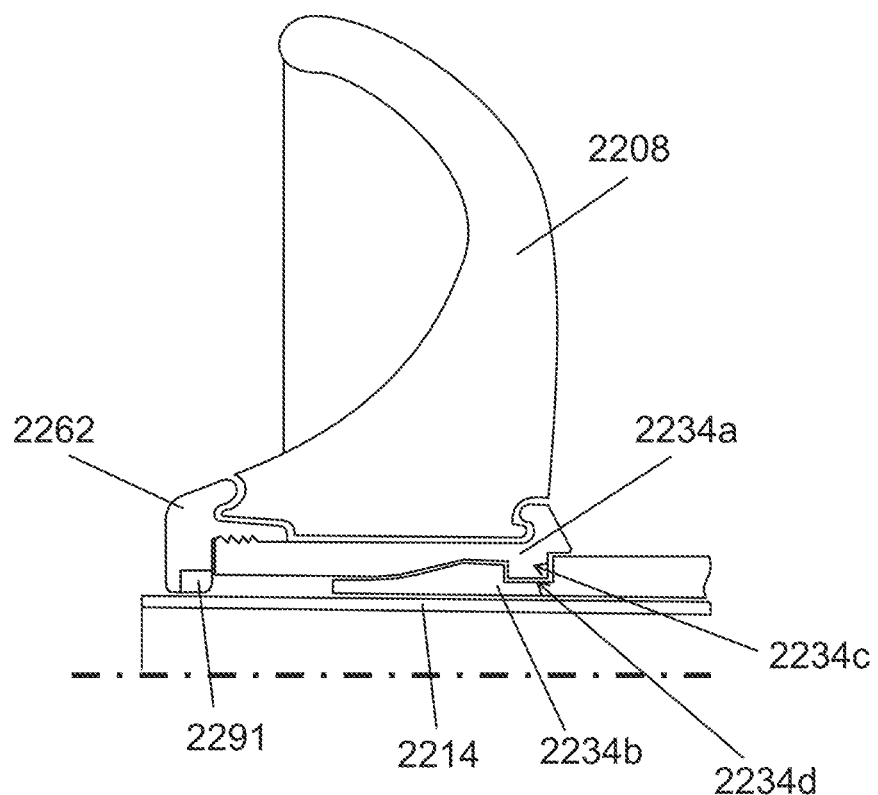
FIG. 22 is a simplified schematic cross sectional view of a portion of an inner bolster connected to an outer tube (not illustrated) by interlocking connecting elements, according to some embodiments of the invention.

FIG. 22 is a simplified schematic cross sectional view of a portion of an internal bolster 2208 connected to an outer tube (not illustrated) by interlocking connecting elements 2234a, 2234b, according to some embodiments of the invention. An exemplary axis of symmetry of the device is illustrated as a dash-dot line. In some embodiments a first connecting element 2234a connects an (optionally flexible) internal bolster portion 2208 to a second connecting element 2234b, where second connecting element 2234b is connected to the outer tube. In some embodiments, connecting elements 2234a, 2234b, are rigid. In some embodiments, connecting elements 2234a, 2234b, connect by a snap lock mechanism where one of connecting elements 2234a, 2234b, includes one or more protruding portion which interlocks with one or more hollow in the other portion. For example, in some embodiments, first connecting element 2234a includes a protruding portion. As connecting element 2234b is inserted into connecting element 2234a, connecting element 2234a elastically deflects the elastic return force pushing protruding portion 2234c into hollow 2234d.

Figure 23:
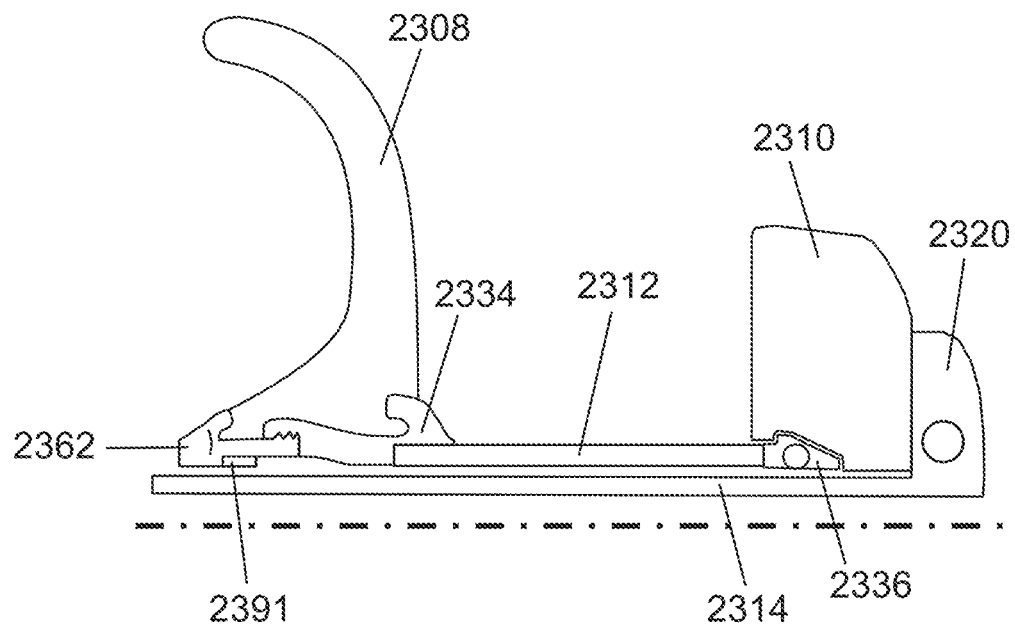
FIG. 23 is a simplified schematic cross sectional view of an ostomy device, according to some embodiments of the invention.

FIG. 23 is a simplified schematic cross sectional view of an ostomy device, according to some embodiments of the invention. An exemplary axis of symmetry of the device is illustrated as a dash-dot line. In some embodiments, an internal bolster 2308 is permanently attached to outer tube 2312 by gluing and/or injection molding of internal bolster 2308 and outer tube 2312 with an optionally rigid connector 2334. In some embodiments, connection between an external bolster 2310 and outer tube 2312 is by a snap lock connection between the two parts, e.g. between a rigid connector and a flexible part (e.g. connector 2336 is rigid and external bolster 2310 is flexible) and/or between two rigid parts (e.g. connector 2336 is rigid and external bolster 2310 is rigid).

In some embodiments, one or more alternative or additional methods and/or types of connector of attachment between bolsters and the inner tube is used, for example, screw attachment, other types of rotation locking, collet, adhesion (e.g. gluing).

Exemplary Connection of Flexible Tube to Rigid Connector/s

Referring back to FIGS. 2A-2B, in some embodiments, connecting elements 234 and 236 connect to the outer tube by contacting the inside of the outer tube 212. For example, in some embodiments tube 212 is stretched around a connector (e.g. 234, 236), a reactive force (e.g. elastic reactive force) from the tube holding the connector in place.

In some embodiments, tube 212 and/or one or more connector 234, 236 are shaped such that a force required to insert the connector into the tube is less than that required to remove the connector. For example, in some embodiments connector/s 234 and/or 236 attach to outer tube 212 by tapered friction fit components, for example, the connectors have one or more angled (e.g. serrated) edge or component.

In some embodiments, connection between outer tube 212 and connector/s and/or other parts of the device is by gluing and/or clamping the outer tube between two rigid parts.

Figure 24:
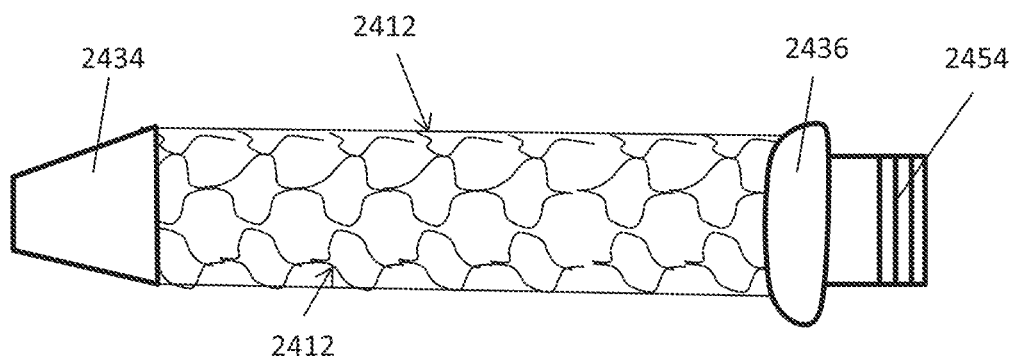
FIG. 24 is a simplified schematic of a tube including a mesh and connectors, according to some embodiments of the invention.

In some embodiments, connection between a flexible outer tube, for example connected to one or more rigid connector (e.g. tube 212 and connectors 234 and/or 236) includes an internal structure (e.g. providing support to the connectors). FIG. 24 is a simplified schematic of a tube 2412 including a mesh 2412a and connectors 2434, 2436, according to some embodiments of the invention.

Figure 25:
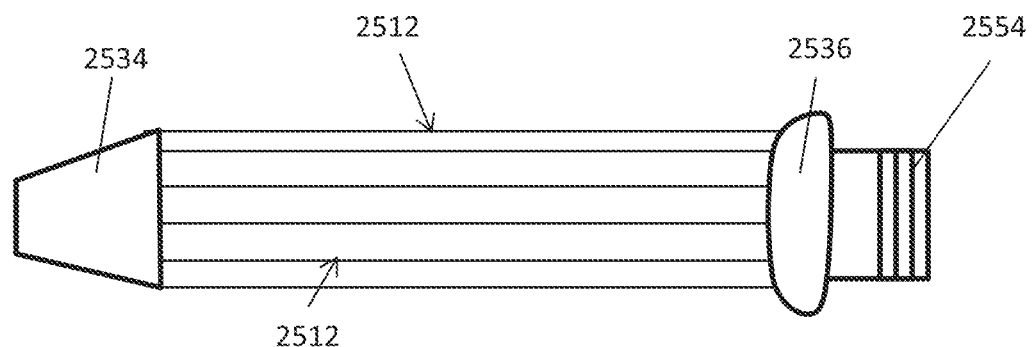
FIG. 25 is a simplified schematic of a wire-reinforced tube and connectors, according to some embodiments of the invention.

In some embodiments, an ostomy device tube is reinforced by elongated elements (e.g. wires). FIG. 25 is a simplified schematic of a wire-reinforced tube 2512 and connectors 2534, 2536, according to some embodiments of the invention.

In some embodiments, a tube includes an internal structure (e.g. mesh 2412, elongated elements 2512) within a sheath and/or coating (e.g. silicone), for example, the internal structure providing structural strength (e.g. crush resistance and/or axial tensile strength) and the sheath providing sealing. In some embodiments, a tube includes an internal structure with a high percentage of open space on the outer surface of the tube (e.g. more than 30%, more than 50%, more than 80% open space, or lower, or higher or intermediate percentages of open space). For example, in some embodiments, a tube internal structure provides a stable base (e.g. internal structure is of metal) for while high percentage of open space maintains tube flexibility.

Figure 26:
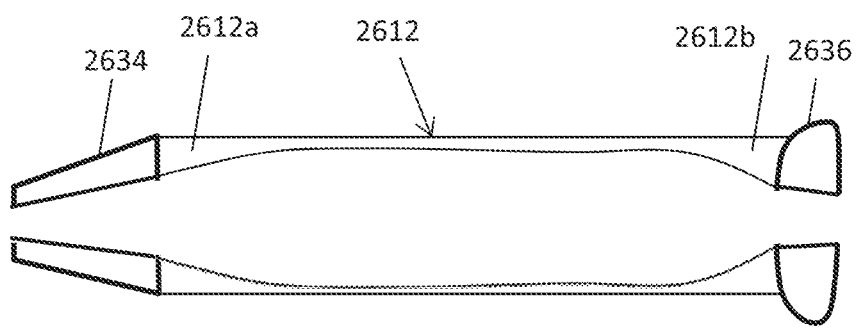
FIG. 26 is a simplified schematic cross sectional view of tube including thickened tube wall portions, and connectors, according to some embodiments of the invention.

In some embodiments, an ostomy device tube is reinforced by thickened walls adjacent to and/or overlapping connectors. FIG. 26 is a simplified schematic cross sectional view of tube 2612 including thickened tube wall portions 2612a, 2612b, and connectors 2634, 2636, according to some embodiments of the invention.

Exemplary Support from Bolsters

As described previously, bolsters, in some embodiments, reduce and/or prevent moving and/or sliding of the outer tube within the stoma. In some embodiments, one or both bolsters are shaped such that a portion of patient tissue that the bolster contacts is at a distance from the opening of the stoma. A potential advantage may include reduction in irritation and/or inflammation to the delicate tissue around the stoma.

In some embodiments, one or more bolster has a shape where a contour of the bolster facing to the patient tissue surface (e.g. the bolster underside contour) extends away from a central axis of the device (central axis passing through the patient stoma) and towards the patient tissue surface such that contact areas of the bolster with the patient tissue surface (abdomen surface for external bolster, stomach lining for internal bolster) are at a distance from the opening of the stoma.

For example, in some embodiments, contact point/s between the external bolster and the patient outer abdominal surface is at a distance from an opening of the stoma on the patient outer abdominal surface between 2-30 mm, between 5-25 mm, or between 5-15 mm, or smaller, or larger, or intermediate distances.

For example, in some embodiments, contact point/s between the internal bolster and the lumen inner wall is at a distance from an opening of the stoma inside the lumen of between 1-15 mm, and/or between 2-10 mm, and/or smaller, and/or larger, and/or intermediate distances.

In some embodiments, the external and/or internal bolster are dome shaped, with the peak of the dome connected to the outer tube, where contact between the bolster and the tissue surface is a ring, for example as illustrated in FIG. 2A and FIG. 49B.

In some embodiments, contact between the external bolster and the patient outer abdominal surface provides support to the ostomy device. In some embodiments, the external bolster, at least when it is elastically relaxed, includes a shape with a planar end edge, potentially providing a continuous contour of contact with patient outer abdominal surface (e.g. skin surface). For example, returning back to FIGS. 2A-2B where contact between external bolster 210 and patient skin is a ring shape corresponding to a rim of the external bolster). In some embodiments, the external bolster includes a dome shape.

Alternatively, in some embodiments, e.g. as described herein, the external and/or internal bolster include separate sections. For example, in some embodiments, contact between the bolster and the tissue surface is at more than one discrete points, for example, providing aeration to an area of skin under the external bolster, for example allowing different portions of the stomach lining to support the device at different times (e.g. the inner bolster, in some embodiments, is rotated periodically, portions of the stomach lining contacting the inner bolster changing with the rotation).

In some embodiments, an external bolster includes a plurality of petals, for example, as illustrated in FIG. 18A which illustrates a device with three petals 1899. In some embodiments, the external fixation device has two petals, or more than three petals, e.g. four petals, up to 10 petals, up to 20 petals.

Alternatively or additionally, in some embodiments, external bolster includes notches and/or ducts and/or or holes e.g. to provide aeration. FIG. 33 is a simplified schematic side view of an external bolster including a plurality of notches 3360, according to some embodiments of the invention.

Exemplary Adjustable Length of Ostomy Device

In some embodiments, an ostomy device (e.g. as described herein) is deployable into a range of thicknesses of stoma, where bolsters hold the device in position. In some embodiments, a height of one or both bolsters is set, for example, upon installation of the device.

Exemplary Adjustable Position of External Bolster

In some embodiments, an axial length of an ostomy device (e.g. 100, 200, 1800 as described herein) is adjustable, for example, when installing the device within a patient and/or when the device is installed within a patient.

In some embodiments, a position of attachment of one or more bolster (e.g. the external bolster) with respect to the outer tube is adjustable meaning that a single device is adjustable to different lengths of stoma. FIG. 27 is a simplified schematic cross section of an ostomy device 2700 with an adjustable tube length within the patient body, according to some embodiments of the invention. A position of an external bolster is adjustable from position illustrated by 2710 on tube 2712 when patient outer abdominal surface is at 2706 to a position illustrated by 2710a.

FIG. 28A is a simplified schematic section view of a portion of an ostomy device, according to some embodiments of the invention. FIG. 28A illustrates an embodiment where an outer tube 2812 is connected to an external bolster 2810 by a connector 2836. In some embodiments, external bolster 2810 is a flexible component coupled to connector 2836 by elastic tension of external bolster 2810. In some embodiments, the position of external bolster 2810 in an ostomy device axial direction is adjustable e.g. by manually moving the bolster.

In some embodiments, a position of an external bolster (e.g. 2810) with respect to a connector (e.g. 2836) and/or an outer tube (e.g. 2812) is adjustable by a screw mechanism. For example, external bolster 2810 and a connector 2836 include matching thread.

In some embodiments, connection between external bolster 2810 and connector 2836 where a position of external bolster 2810 on connector 2836 is optionally axially adjustable, is strengthened by interlocking elements (e.g. by increasing resistance to axial movement of the external bolster). FIGS. 28B-28D are simplified schematic cross sectional views of exemplary interlocking connection between external bolster and connector, according to some embodiments of the invention. FIGS. 20A-20B also illustrate interlocking connection between an external bolster 2010 and a portion connected to the external bolster 2020; interlocking threads 2090, 2091.

In some embodiments, the external bolster is connected to one or more additional part and/or is not attached to a tube connector. For example, in some embodiments the external bolster is connected to an inner tube portion head (e.g. as described herein).

In some embodiments, position of the external bolster on the tube is adjustable by up to 50 mm, or up to 30 mm, or 10-40 mm, or lower, or higher, or intermediate ranges or distances.

Exemplary Adjustable Position of Inner Bolster

In some embodiments, a position of one or more portion of an inner bolster is adjusted, for example, adjusting a minimum dimension between the inner and outer bolsters. In some embodiments, adjustment is during installation, and/or once the ostomy device is installed (e.g. periodically). In some embodiments, the inner bolster is adjusted from outside the patient.

Figure 32A:
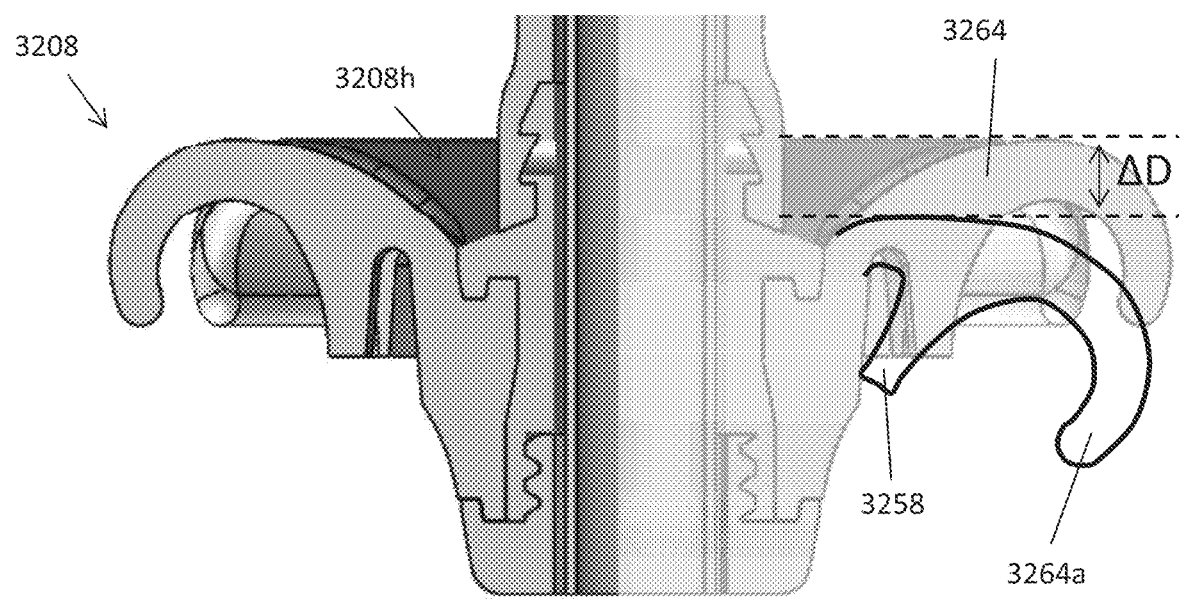
FIG. 32A is a simplified schematic section view of a portion of an elastic internal bolster, according to some embodiments of the invention.

For example, referring to FIG. 32A, in some embodiments, an element attached to one or more petal 3208*a* (and e.g. running through the inner bolster is used to adjust a deflection of the petal (e.g.) from a relaxed position illustrated by 3208*a*. In some embodiments, the element is connected to bumper 3258 and, for example, pulling on the element deflects the petal, releasing the element reduces deflection of the petal.

Exemplary Axial Length of Device Related to Pressure on Bolsters

In some embodiments, an axial length of the tube within patient tissue and/or a minimum separation between an inner and an external bolster changes in reaction to a pressure applied to the internal and/or external bolsters by the patient tissue therebetween, for example, pressure related to swelling and/or reduction in swelling of patient tissue.

Figure 29A:
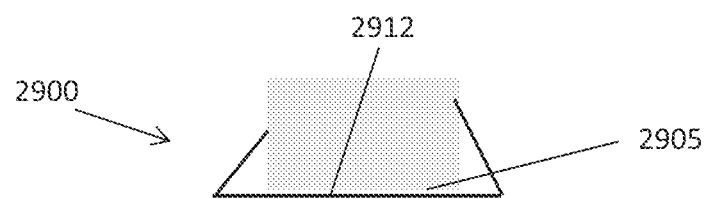
FIG. 29A is a simplified schematic cross section of an ostomy device with adjustable axial length, according to some embodiments of the invention.

FIG. 29A is a simplified schematic cross section of an ostomy device 2900 with adjustable axial length, according to some embodiments of the invention. Ostomy device 2900 is installed within a stoma 2905, with internal and external bolsters, 2908 and 2910 respectively holding a tube 2912 in position within stoma 2905. A length of tube 2912 within the stoma is L1.

Figure 29B:
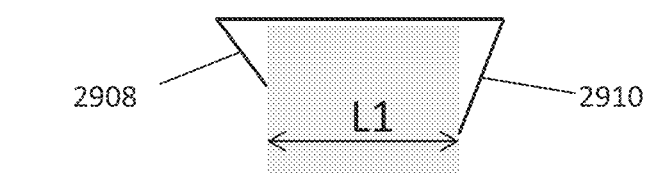
FIG. 29B is a simplified schematic cross section of an ostomy device with adjustable axial length within swollen tissue, according to some embodiments of the invention.

In some embodiments (e.g. post operatively) patient tissue swells around stoma 2912. FIG. 29B is a simplified schematic cross section of an ostomy device 2900 with adjustable axial length within swollen tissue, according to some embodiments of the invention. In some embodiments FIG. 29B illustrates the device of FIGS. 29A-29B where patient tissue has swollen, increasing a length of stoma 2905 to L2 (L2>L1). In some embodiments, under pressure from patient tissue internal bolster 2908 and/or external bolster 2910 (FIG. 29B illustrates both) bend (optionally elastically) and/or pivot to increase a length of tube 2902 within stoma 2905 (e.g. by reducing a height of the bolster/s above the lumen wall/patient outer abdominal surface). Alternatively or additionally, in some embodiments, tube 2902 is axially elastic, elastically increasing a tube length e.g. upon tissue swelling and/or decreasing a tube length e.g. upon subsidence of tissue swelling.

Figure 30:
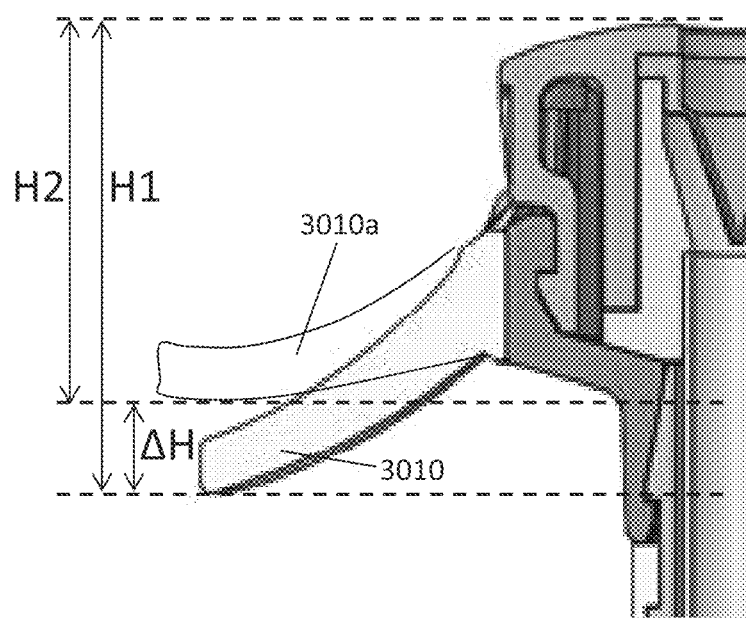
FIG. 30 is a simplified schematic section view of a portion of an ostomy device where a protrusion of the device above a patient outer abdominal surface is adjustable, according to some embodiments of the invention.

FIG. 30 is a simplified schematic section view of a portion of an ostomy device where a protrusion of the device above a patient outer abdominal surface is adjustable, according to some embodiments of the invention. In some embodiments, adjustment is by bending and/or deflection of the bolster. FIG. 30 illustrates elastic bending of an external bolster 3010 to change a tube length within the patient. This adjustment corresponds to a change in height of the device above the patient outer abdominal surface. External bolster 3010 bends to a second position 3010*a* decreasing a height of the device above a patient outer abdominal surface from H1 to H2, corresponding to a change in height of ΔH=H2-H1. In some embodiments, change in height (ΔH) is 1-15 mm, or 2-10 mm, or 3-7 mm, or up to 5 mm, or up to 10 mm, or lower, or higher, or intermediate ranges or lengths.

In some embodiments, a bolster includes protrusions which are unattached, for at least a portion of the protrusion, and, in some embodiments, each protrusion deflects and/or bends (optionally elastically) to a different extent.

In some embodiments, the external bolster includes elastically deflectable petals which contact the patient outer abdominal surface at discrete points (e.g. petals 1899).

In some embodiments, each petal 1899 elastically deflects a different extent, for example, the bolster to provide support in the case of non planar patient anatomy.

Figure 31A:
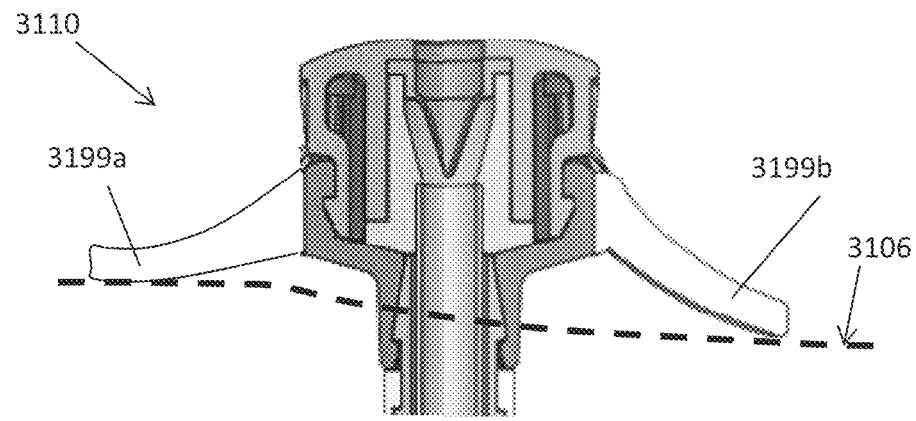
FIG. 31A is a simplified schematic section view of an external bolster bending to fit an abdominal outer surface, according to some embodiments of the invention.

In some embodiments, different portions of an external bolster bending to different extents allow the device to fit an abdominal outer surface. FIG. 31A is a simplified schematic section view of an external bolster 3110 bending to fit an abdominal outer surface 3106, according to some embodiments of the invention. First petal 3199*a* bends to a larger extent than second petal 3106, fitting external bolster 3110 to a non-planar topography of abdominal outer surface 3106. Similarly, in some embodiments, different portions of an inner bolster deflect to different extents, fitting the inner bolster to non-planar topography of a lumen inner wall.

Figure 31B:
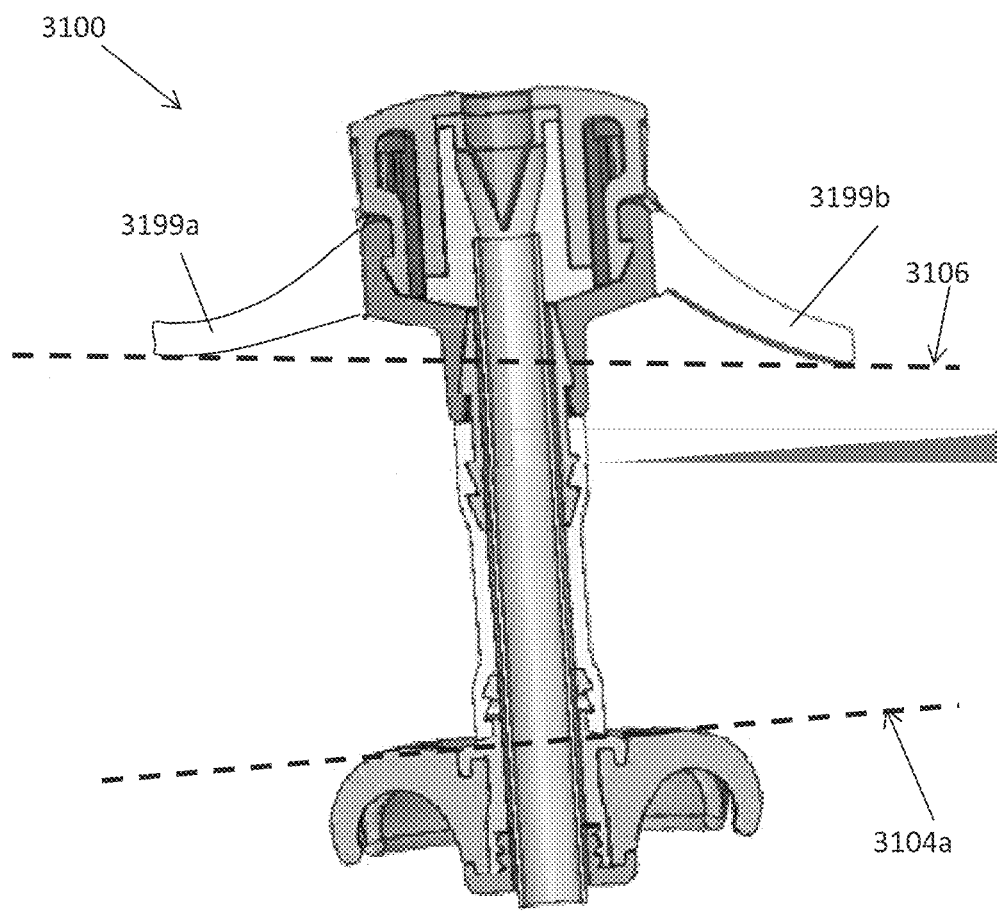
FIG. 31B is a simplified schematic section view of a device where an external bolster is bending to fit the device to a patient anatomy, according to some embodiments of the invention.

FIG. 31B is a simplified schematic section view of a device where an external bolster 3120 is bending to fit the device to a patient anatomy, according to some embodiments of the invention. In some embodiments, a lumen inner wall 3104*a* and an abdominal outer surface 3106 are non-parallel and, in some embodiments, external bolster petals 3199*a*, 3199*b* bend to different extents to fit the device to the patient anatomy. In some embodiments, bending of bolster portions is in addition to bending of a flexible outer tube.

Additionally or alternatively, in some embodiments, different portions of an inner bolster deflect to different extents, fitting the inner bolster to non-parallel patient anatomy.

FIG. 32A is a simplified schematic section view of a portion of an elastic internal bolster 3208, according to some embodiments of the invention.

FIG. 32A illustrates elastic bending of an internal bolster 3210 to change a tube length within the patient. This adjustment corresponds to a change in height of the device above the patient outer abdominal surface. Petal 3264 bends to a second position 3264*a* decreasing a depth of the device within the lumen (e.g. stomach). In some embodiments, change in depth (ΔD) is 1-15 mm, or 2-10 mm, or 3-7 mm, or up to 5 mm, or up to 10 mm, or lower, or higher, or intermediate ranges or lengths. In some embodiments, internal bolster is designed to have a maximum change in depth, the device locking and becoming rigid. In some embodiments, internal bolster includes (e.g. for each petal of internal bolster) a bumper 3258 which is shaped to prevent bending (e.g. by contacting another portion of the device) of the bolster beyond a maximum change in depth, as illustrated by internal bolster 3208*a*.

In some embodiments, such elasticity of the internal bolster prevents embedding of the internal bolster within the stomach wall.

In some embodiments, one or more compressible component for example, a sponge, a balloon, a spring (e.g. ring-shaped) disposed between the inner bolster and the lumen inner wall.

In some embodiments, a dimension (e.g. axial extent of the component between the inner bolster and the lumen wall) of the compressible component is adjustable during installation (e.g. a size of the component is selected before insertion at installation). In an exemplary embodiment, an axial dimension of the compressible component is adjustable after installation, for example, from outside the patient, e.g. without needing an endoscopic procedure.

Figure 32B:
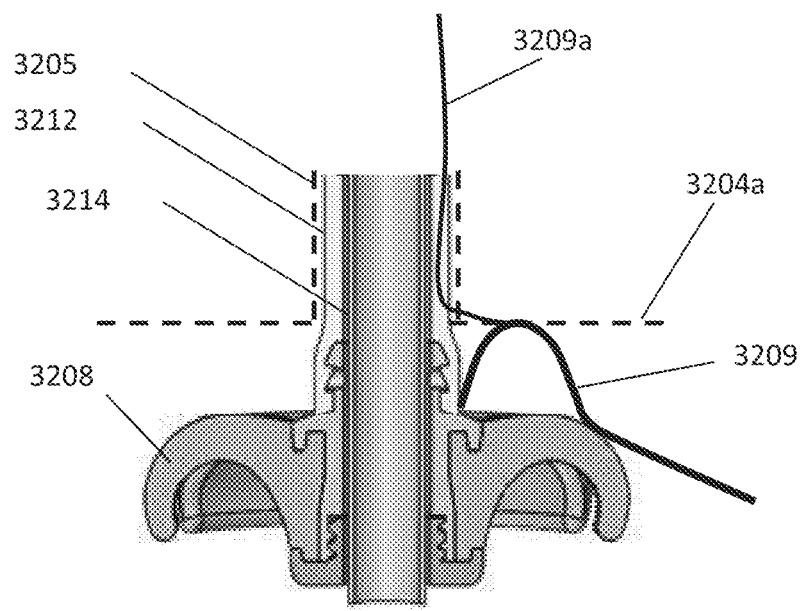
FIG. 32B is a simplified schematic cross sectional view of an inner bolster, a lumen inner wall and a compressible component therebetween, according to some embodiments of the invention.

FIG. 32B is a simplified schematic cross sectional view of an inner bolster 3208, a lumen inner wall 3204a and a compressible component 3209 therebetween, according to some embodiments of the invention. In some embodiments, an elongated element 3209a is connected to compressible component 3209 and passes through an outer tube 3212 (alternatively, or additionally, in some embodiments, compressible component 3209 passes through an inner tube 3212 and/or a stoma 3205 and/or another abdominal incision). In some embodiments, an axial extent of compressible component 3209 is adjusted by pulling or releasing elongated element 3209a optionally, compressible component is pulled and/or released and then fixed in position, e.g. by a ratchet mechanism. In some embodiments, compressible component 3209 is elastic (e.g. it is a spring) optionally including plastic.

In an exemplary embodiment, an external bolster (e.g. as described herein) provides more axial elasticity than an internal bolster (e.g. as described herein), for example, with a maximum AH at least double a maximum AD. In some embodiments, external bolster holds ostomy device (e.g. as described herein) in position by applying gentle pressure to the patient skin.

In some embodiments, adjustable position of the external bolster and/or elasticity of the external bolster mean that the device is well fitting, e.g. at all times, and/or meaning that the device has a low profile, e.g. a small height above the patient outer abdominal surface, for example, 0.2 mm-18 cm, 0.5 mm-5 cm, 0.5 mm-3 cm, or lower, or higher, or intermediate ranges or values.

Exemplary Removal
Exemplary Method of Removal

Figure 34:
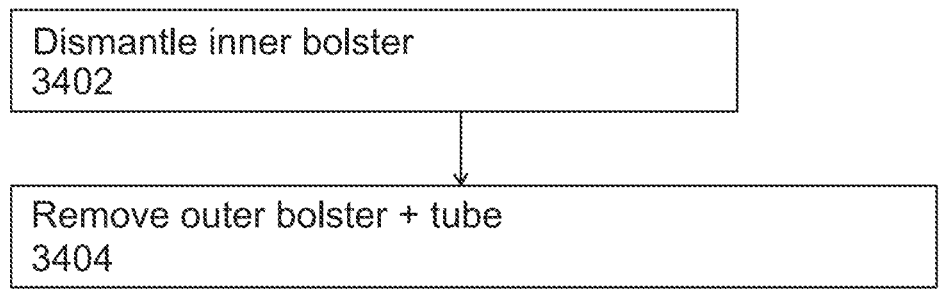
FIG. 34 is a flow chart of a method of ostomy device removal, according to some embodiments of the invention.

FIG. 34 is a flow chart of a method of ostomy device removal, according to some embodiments of the invention.

At 3402, an inner bolster (e.g. as described herein) is dismantled into more than one piece. In some embodiments, connector/s coupling portions of the internal bolster are loosened and/or removed, for example, releasing the portions. In some embodiments, the portions of the inner bolster then move away from the inner tube, for example, due to movement of the stomach and/or stomach contents. In some embodiments, a user moves the outer tube, for example, rotates and/or shakes the outer tube (e.g. by moving the external bolster) to separate the de-coupled inner bolster portions and/or move them from the inner tube. In some embodiments, removing the outer tube moves the inner bolster portions away from the outer tube.

In an exemplary embodiment, a user dismantles the internal bolster externally, for example, without approaching the device from within the lumen, (e.g. without performing an endoscopic procedure). In some embodiments, the dismantled portions of the internal bolster are free within the lumen (e.g. stomach), for example, then passing through the digestive system. Alternatively, in some embodiments, the disassembled portions are then removed from the lumen (e.g. by pulling through the stoma).

At 3404, in some embodiments, once the internal bolster is dismantled, the outer tube and external bolster are removed e.g. by a user pulling on the external bolster.

Exemplary Dismantling of Internal Bolster

In an exemplary embodiment the petals substantially do not overlap, for example, substantially do not overlap axially (overlap being where petals contact each other in a planes approximately perpendicular to the long axis of the tube). In some embodiments, petals at most overlap axially with adjacent (e.g. radially adjacent) petals.

In some embodiments, residue (e.g. stomach contents) coating the inner bolster (e.g. coating contact areas between petals) prevents and/or slows disassembly of inner bolster petals. In some embodiments, the inner bolster includes one or more notch and/or inlet separating portions of the inner bolster e.g. between petals. For example, reducing an area of contact between petals potentially reduces friction of movement of petals away from each other.

In some embodiments, the internal bolster includes a plurality of petals which are held by one or more connectors (e.g. in some embodiments, petals are held between two or more connectors) where disconnecting the connectors decouples the petals.

Figures 35A, 35B:
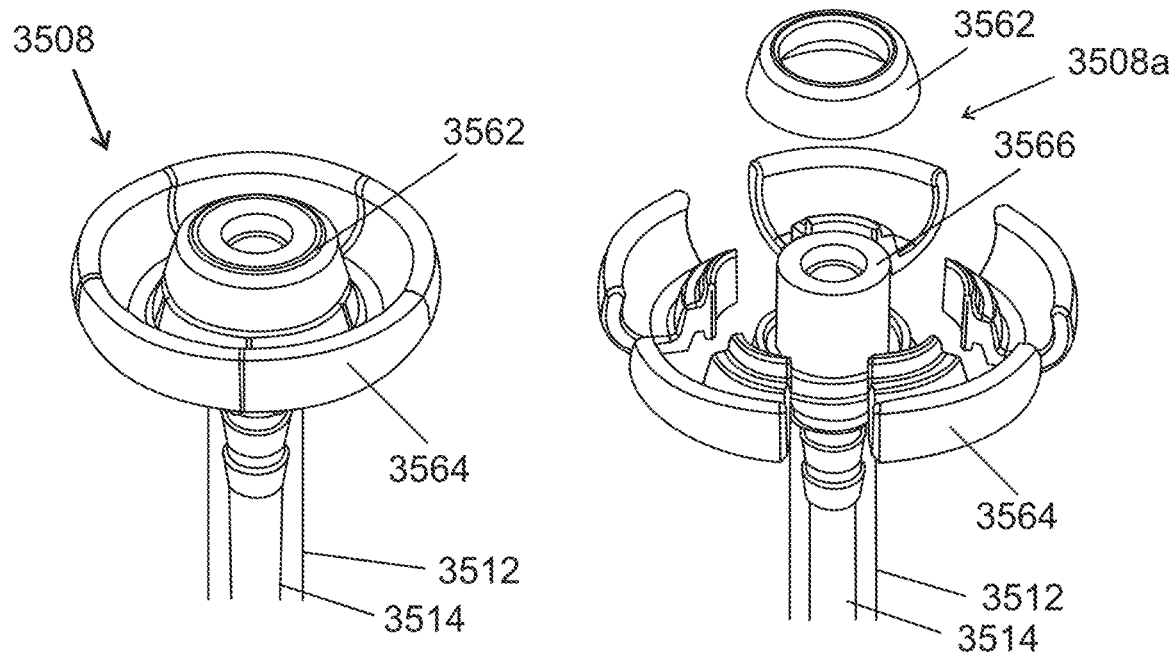
FIG. 35A is a simplified schematic side view of an internal bolster including a plurality of petals, according to some embodiments of the invention.
FIG. 35B is a simplified schematic side view of a dismantled internal bolster including a plurality of petals, according to some embodiments of the invention.

FIG. 35A is a simplified schematic side view of an internal bolster 3508 including a plurality of petals 3564, according to some embodiments of the invention. FIG. 35B is a simplified schematic side view of a dismantled internal bolster 3508 including a plurality of petals 3564, according to some embodiments of the invention.

In some embodiments, petals 3564 do not overlap. In some embodiments, each petal overlaps with one or both radially adjacent petals. In some embodiments, axial overlap between petals 3564 is small, for example, less than 20%, or less than 10%, or less than 5%, or less than 3%, or lower, or higher, or intermediate percentages, of a petal surface area is in contact with another petal, before dismantling.

Referring back to FIG. 18A, in an exemplary embodiment petals 1864 are separate, where the inner bolster includes notches 1865 separating petals 1864.

In some embodiments, internal bolster 3508 dismantles into a plurality of parts (e.g. including petals 3564) upon release of a connecting cap 3562 which holds portions of the internal bolster together. In some embodiments, one or more part holding portion/s of the internal bolster together is rigid.

In an exemplary embodiment, internal bolster portions are held between two rigid parts. Referring back to FIG. 18B, a cap 1862 and connector 1834 hold between them internal bolster 1808.

In some embodiments, cap 3562 holds internal bolster petals 3564 onto an internal bolster shaft 3566 and, in some embodiments, upon removal and/or of cap 3562, petals 3564 are released. In some embodiments, internal bolster shaft 3566 is also a connector to outer tube 3512. Alternatively, in some embodiments, internal bolster shaft 3566 (an optionally rigid part) attaches to a connector connecting internal bolster 3508 to outer tube 3512. In some embodiments, the internal bolster shaft 3566 hardness is at least 40 shore A, for example 50 shore A, 60 shore A, 70 shore A or 90 shore A. In some embodiments having a rigid internal bolster shaft 3566 allows for example, to resist bending and/or twisting of the internal bolster 3508 moves through the esophagus into the stomach lumen.

Exemplary Dismantling Using a Tool

In some embodiments, dismantling of the internal bolster is by use of a tool. In some embodiments, a tool engages a connector connecting portions of the inner bolster, for example, disconnecting and/or loosening the connector, for example, by withdrawing and/or applying pressure and/or torque to the connector.

In some embodiments, cap 3562 is detached from petals 3564 and/or from an internal bolster shaft 3566 by a tool inserted through outer tube 3512 or inner tube 3514.

In some embodiments, a tool accesses a hollow within a connector and applies a force (e.g. a torque) to the connector via the hollow (e.g. hollow 2291 FIG. 22, 2391 FIG. 23).

In some embodiments, an outer tube and/or an inner tube portion include a separate channel for insertion of a dismantling tool. FIG. 36 is a simplified section view of a portion of an internal bolster including a tool channel 3674 for a dismantling tool 3668, according to some embodiments of the invention. In some embodiments, channel 3674 is within inner tube 3612. Alternatively, in some embodiments, inner tube portion (e.g. 216, e.g. as described herein) includes two channels, a first channel for food and a second channel for insertion and/or guiding of a dismantling tool.

Exemplary Dismantling by Breaking an Attachment Element

In some embodiments, dismantling is by breaking of a cap attachment 3670. In some embodiments, cap attachment 3670 is broken by pressure applied by a tool 3668. In some embodiments, once cap attachment 3670 is broken, the tool is inserted further towards the lumen, for example, detaching cap 3662 from attachment 3670. In some embodiments, cap hingendly opens e.g. around an interlocked portion 3676, for example, before disengaging from other parts of the internal bolster (e.g. petals 3664).

In some embodiments, tool 3668 is a part sized and shaped for insertion into channel 3674. In some embodiments, tool 3668 is a readily available medical tool, for example, a needle (e.g. syringe needle). In some embodiments, cap attachment 3670 is broken by application of hydraulic pressure (e.g. applied by a syringe). For example tool channel 3674 may run along and/or parallel to a feeding tube 3614.

In some embodiments, an inner tube portion is shaped to accommodate tool channel 3674. FIG. 37A is a simplified schematic side view of an inner tube portion 3716 where inner tube 3714 is non-cylindrical, according to some embodiments of the invention. In this embodiment, tool channel 3774 is defined in a space between the outer tube (not illustrated) and inner tube 3714.

In some embodiments, an inner tube portion inlet includes a tool guide. FIG. 37B is a simplified schematic of an inner tube inlet including a tool guide 3678, according to some embodiments of the invention. In some embodiments, a plurality of tool guides is disposed along a length of the outer tube. Alternatively, in some embodiments, FIG. 37B illustrates an inner tube portion including two channels, a feeding channel 3702 and a tool channel 3774.

Exemplary Turn Mechanism Dismantling

In some embodiments, an internal bolster is dismantled by turning and/or rotating a part with respect to another part, for example, by rotating (e.g. unscrewing) an internal bolster cap (e.g. 3562), for example, from a connector (e.g. 3566).

FIG. 38A is a simplified schematic section view of an internal bolster with a screw dismantling mechanism, according to some embodiments of the invention.

FIG. 38B is a simplified schematic side view of a screw dismantling mechanism tool 3868, according to some embodiments of the invention.

In some embodiments, thread 3880 on a chamber within internal bolster, for example, within an internal bolster cap (e.g. cap 3862) matches thread 3882 on tool 3868. In some embodiments, to dismantle internal bolster 3808, tool 3868 is inserted through a tube (e.g. an inner and/or outer tube), and rotated to dismantle internal bolster 3808.

In an exemplary embodiment, a tool for dismantling an internal bolster includes applies a torque onto a top portion 3993 of the internal bolster. FIG. 39 is a simplified schematic of a portion of a bolster and an expanding dismantling tool 3968, according to some embodiments of the invention. A dash-dot line illustrates an exemplary axis of symmetry of the device. In some embodiments, during insertion of dismantling tool 3968 arms 3967 of the tool are elastically compressed, once the arms exit outer tube the arms expand and a user applies torque to the top of the internal bolster by pulling and rotating the tool. In some embodiments, arms fit into a screw drive 3991 (e.g. two arms fit into a slot screw drive, four arms fit into a Phillips head screw drive).

In some embodiments, a tool including one or more expanding portion is used to apply force (e.g. not only torque) to the top of the internal bolster.

Figure 40A:
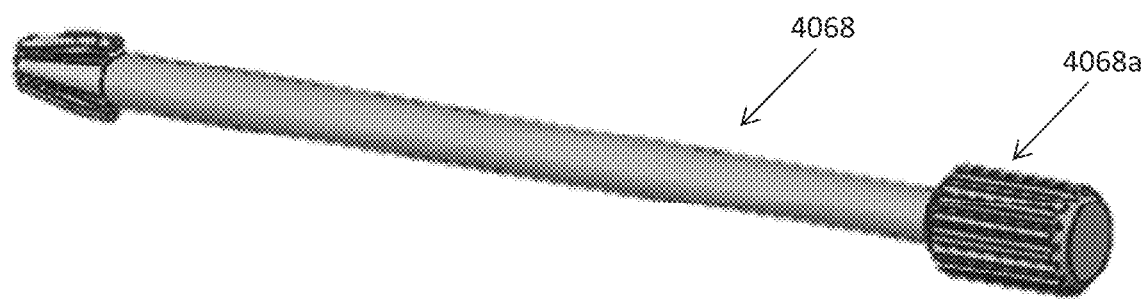
FIG. 40A is a simplified schematic side view of a disassembly tool, according to some embodiments of the invention.
Figure 40B:
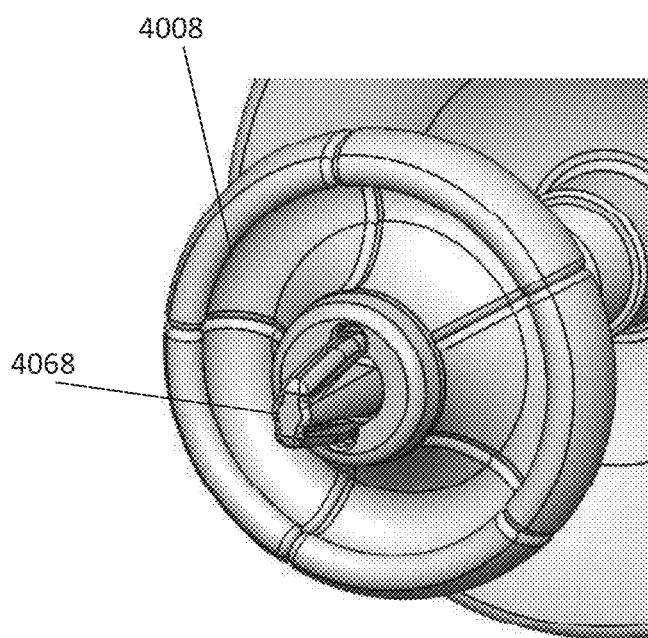
FIG. 40B is a simplified schematic side view of a disassembly tool inserted into an inner bolster, according to some embodiments of the invention.

FIG. 40A is a simplified schematic side view of a disassembly tool 4068, according to some embodiments of the invention. FIG. 40B is a simplified schematic side view of a disassembly tool inserted into an internal bolster, according to some embodiments of the invention. In some embodiments, a torque multiplier is attached to disassembly tool to increase the torque which is applied. In some embodiments, disassembly tool 4068 includes a connector for attachment 4068a to a torque multiplier.

Figure 41A:
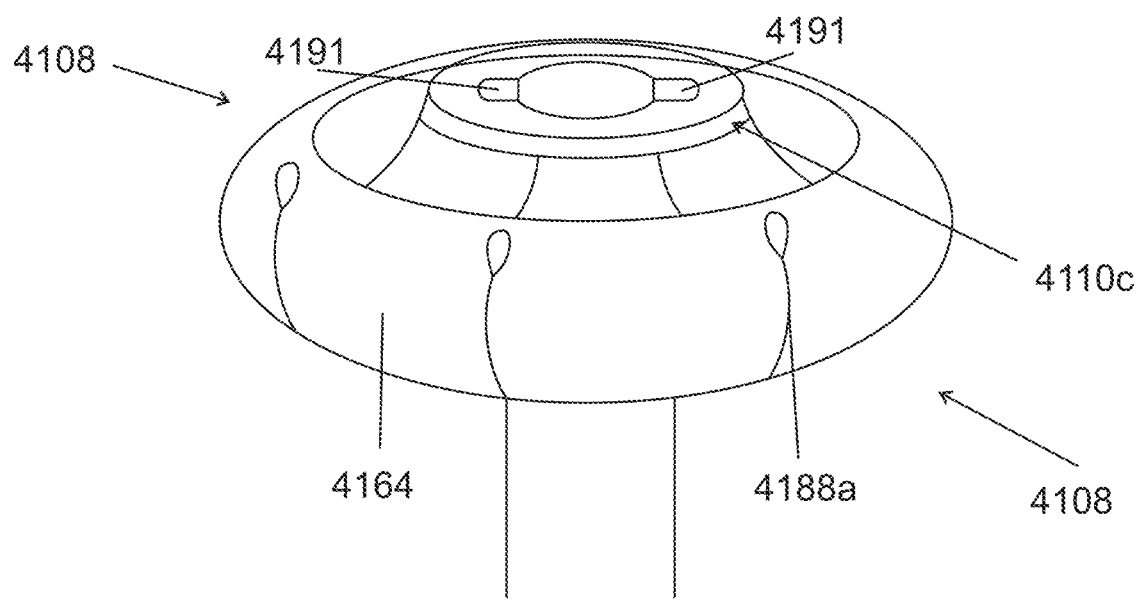
FIG. 41A is a simplified schematic side view of an inner bolster where each petal of the inner bolster is attached to an elongated element, according to some embodiments of the invention.

In some embodiments, disassembled portions of the internal bolster are removed from the stomach by pulling on element/s attached to the internal bolster portions. FIG. 41A is a simplified schematic side view of an internal bolster where each petal 4164 of the internal bolster is attached, according to some embodiments of the invention. In some embodiments, internal bolster 4408 is a single piece including separations 4188a between petals 4164 where, in some embodiments, separations extend but do not reach a central area 4410c of the inner bumper. In some embodiments, separations 4188a are cut into inner bumper 4408 after the inner bumper is formed as a single piece.

Figure 41B:
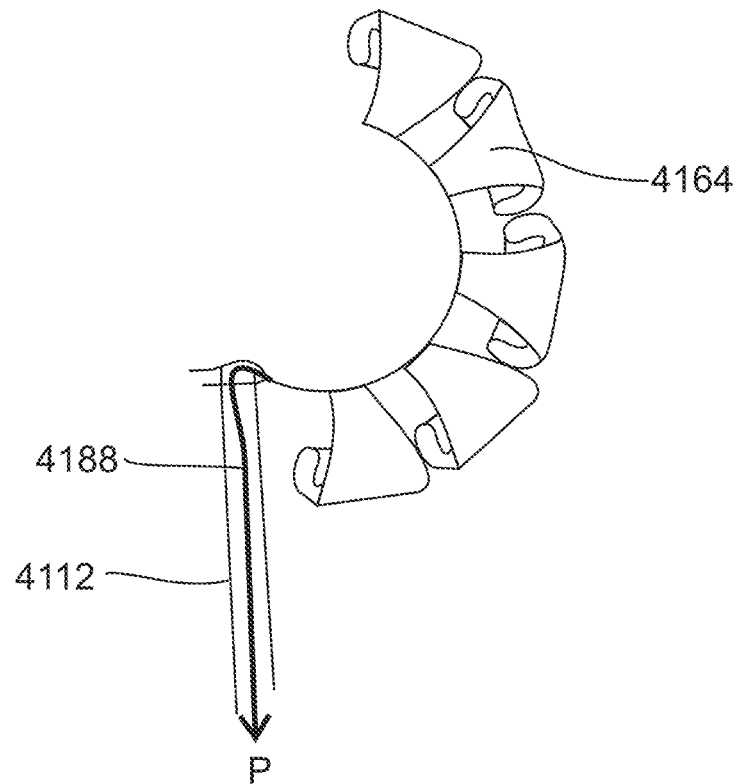
FIG. 41B illustrates removal of disassembled inner bolster portions through an outer tube by pulling, force P on an elongated element 4188, according to some embodiments of the invention.

FIG. 41B illustrates removal of disassembled internal bolster portions through an outer tube 4112 by pulling, force P on an elongated element (not illustrated) according to some embodiments of the invention.

Alternatively in some embodiments, internal bolster petals 4164 are attached one to another by connectors, for example, each petal is attached to adjacent petals by connectors (e.g. hinges and/or flexible portions which allow the petals to disassemble from each other) and, for example, a single petal is attached to an elongated element used to withdraw a chain of connected petals. In some embodiments, petal connectors are of the same material as the petals. Alternatively, in some embodiments, petal connectors are of different material to the petals.

Also illustrated in FIG. 41A are hollows 4191 (e.g. screw drive) of a rotation disassembly mechanism.

In some embodiments, the internal bolster is dismantled by pulling on one or more elongated element 4188.

Alternatively, in some embodiments, the internal bolster is sufficiently flexible to be removed by pulling on the tube from outside the stomach. Alternatively, in some embodiments, the device is dismantled during an endoscopic procedure where, for example, the internal bolster is detached from the tube and, is optionally then removed through the esophagus or the internal bolster attached to the tube is removed through the esophagus.

Installation

Exemplary Method of Installation

Figure 42:
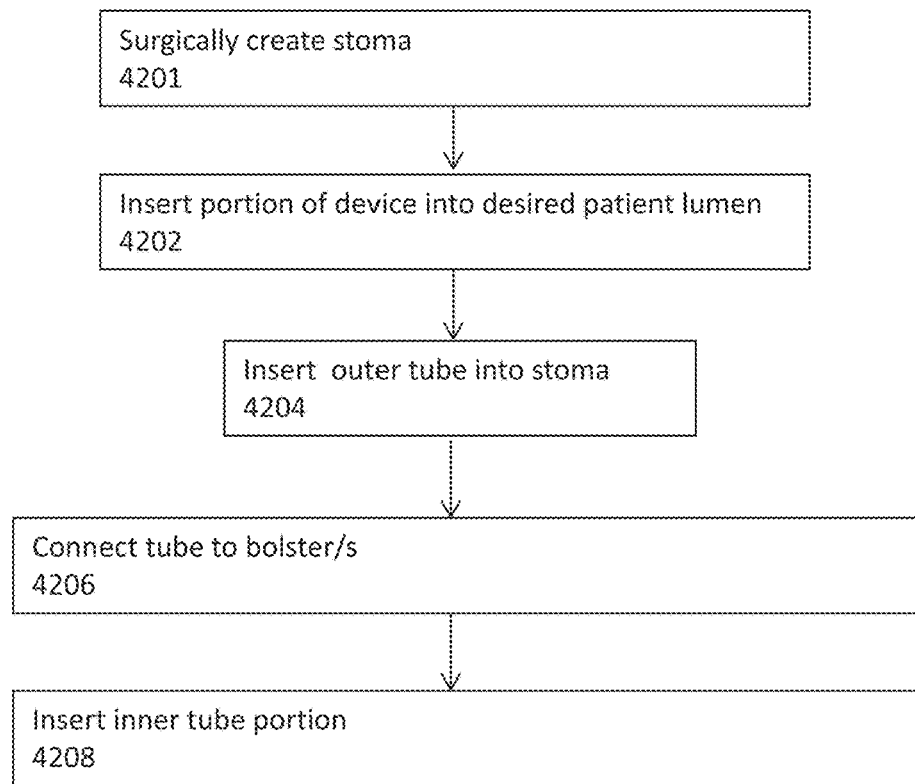
FIG. 42 is a flow chart of a method of ostomy device installation, according to some embodiments of the invention.

FIG. 42 is a flow chart of a method of ostomy device installation, according to some embodiments of the invention.

At 4201, a stoma between a lumen (e.g. stomach) and an outer abdominal surface of the patient is created, for example, using an endoscopic procedure and/or laparoscopy. Alternatively, in some embodiments, a stoma is pre-existing.

In some embodiments, a stoma by making an initial channel with a needle (or other narrow instrument) and creating a stoma by pulling a dilator through the initial channel. In an exemplary embodiment a dilator is connected to one or more portion of the ostomy device and, for example, as the dilator is pulled through patient tissue, portions of the device are installed (e.g. outer tube is installed into the stoma).

In some embodiments, a dilator is pulled and/or pushed through patient tissue and the tube is then inserted into the stoma.

At 4202, one or more portion of the ostomy device is inserted into the lumen (e.g. 104), for example, into the stomach by way of the esophagus. In some embodiments, one or more portion of the ostomy device and/or a dilator and/or pushing device are inserted into the lumen prior to creation of a stoma. In some embodiments, the pushing device is a guiding element which is sized and shaped to allow, for example to guide at least part of the ostomy device from the stomach lumen to the outer surface of the body through the stoma. Optionally, the pushing device is configured to push aside tissue as it passes through the stoma. In some embodiments, an internal bolster (e.g. 108) and optionally an outer tube (e.g. 112) are inserted into the lumen (e.g. 104).

In some embodiments, an internal bolster has hinged and/or flexible and/or elastic portions (e.g. petals as described herein) which move towards each other to contact a cross section of the bolster, for example, allowing the bolster to be inserted into the lumen through the esophagus.

FIG. 49A is a simplified schematic cross sectional view of an inner bolster 4908 attached to an outer tube 4912 being inserted through an esophagus 4986, according to some embodiments of the invention. In some embodiments, petals 4964 bend and/or rotate towards each other, optionally elastically, contracting a cross section of inner bolster 4908.

FIG. 49B is a simplified schematic cross sectional view of an inner bolster 4908 attached to an outer tube 4912 where the outer tube is installed within a stoma 4905, according to some embodiments of the invention.

Alternatively or additionally, in some embodiments, the internal bolster is inserted into the stomach (e.g. through the esophagus) in several portions and the portions are then assembled within the stomach.

In some embodiments, the outer tube is also inserted into the stomach (e.g. through the esophagus), the outer tube is then attached to the internal bolster. Alternatively, in some embodiments, the internal bolster attached to the outer tube is inserted into the stomach through the esophagus.

At 4204, in some embodiments, the outer tube is inserted into the stoma (e.g. as described above). In some embodiments, the outer tube (previously inserted into the lumen) is pushed and/or pulled through the surgically created stoma from the stomach.

In some embodiments, the tube is pulled through the stoma by pulling on one or more elongated element, (e.g. including wire and/or cord and/or cable and/or thread) coupled to the outer tube. In some embodiments, once the outer tube is in position, the elongated element is removed from the outer tube.

Figure 43:
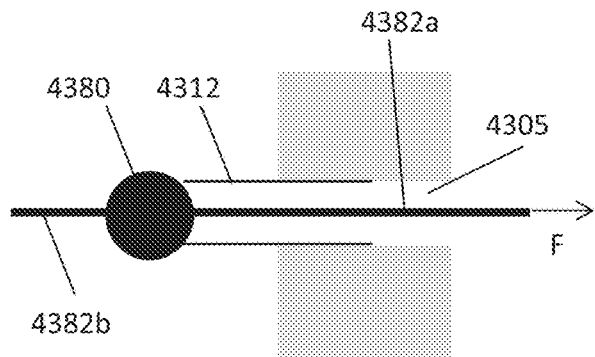
FIG. 43 is a simplified schematic cross sectional view of an outer tube being pulled into a stoma by a pushing device 4380, according to some embodiments of the invention.

In some embodiments, a pushing device which is too large to be pulled through the outer tube is used to pull the outer tube (and optionally an internal bolster attached to the outer tube) through the stoma. In some embodiments, the pushing device is a guiding element which is sized and shaped to allow, for example to guide at least part of the ostomy device from the stomach lumen to the outer surface of the body through the stoma. In some embodiments, once the outer tube is in position, the pushing device is removed from the lumen (e.g. by pulling on an elongated component connected to the pushing device and extending out of the esophagus). FIG. 43 is a simplified schematic cross sectional view of an outer tube 4312 being pulled into a stoma 4305 by a pushing device 4380, according to some embodiments of the invention. In some embodiments a pulling force, F is applied to elongated element 4382a by a user to pull outer tube 4312 into position. In some embodiments a second elongated element 4382b is attached to pushing device 4380 and is used to extract pushing device 4380 from the patient (e.g. through the esophagus).

In some embodiments pushing elongated element 4305 (where elongated element optionally includes a dilator with a tapered portion) attaches to pushing device 4380 by a screw mechanism or a different connection mechanism e.g. snap lock, e.g. gluing.

Figures 44A, 44B:
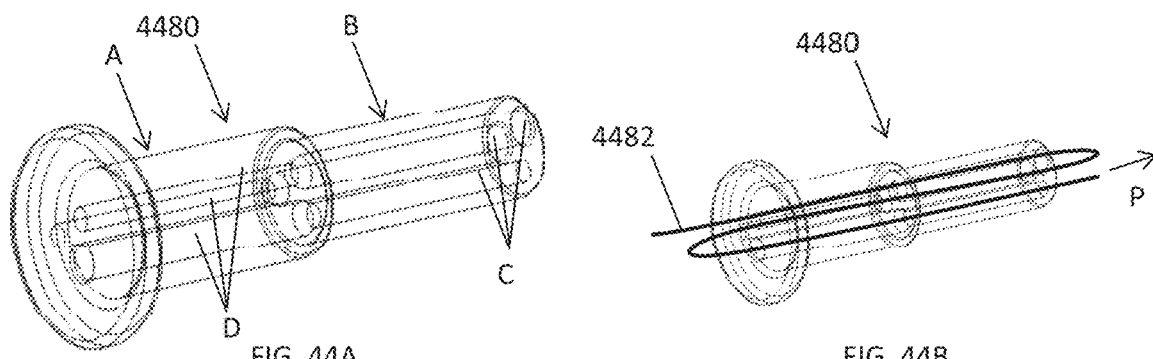
FIG. 44A is a simplified schematic side view of a pushing device, according to some embodiments of the invention.
FIG. 44B is a simplified schematic side view of a pushing device threaded with an elongated element, according to some embodiments of the invention.

In some embodiments, a single elongated element is used to pull the pushing device for insertion of the outer tube and is used to remove the pushing device from the lumen. FIG. 44A is a simplified schematic side view of a pushing device 4480, according to some embodiments of the invention. FIG. 44B is a simplified schematic side view of a pushing device 4480 threaded with an elongated element 4482, according to some embodiments of the invention. In some embodiments, change in direction of elongated element 4482 within pushing device 4480 is sufficient to hold the pushing device in position on the elongated element allowing the device to be moved by pulling on either end of elongated element 4282.

In some embodiments, channels within pushing device 4480 change in radius along a length of the pushing device. In some embodiments, pushing device 4480 includes two components, A and B, where A plugs into B, channels C illustrated in fitting into plugs of D (or plugs C fitting into channels D). In some embodiments B fits into the tube and A plugs into portion B.

In some embodiments, the outer tube includes a sharp end and/or a sharp attachment is fitted to the outer tube and/or a tapered portion (also herein termed dilator), and the stoma is created by the insertion of the inner tube.

Figure 45A:
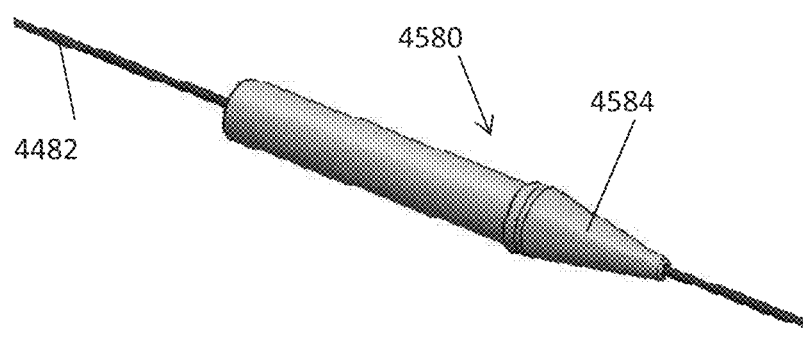
FIG. 45A is a simplified schematic side view of a pushing device including a tapered end, according to some embodiments of the invention.
Figure 45B:
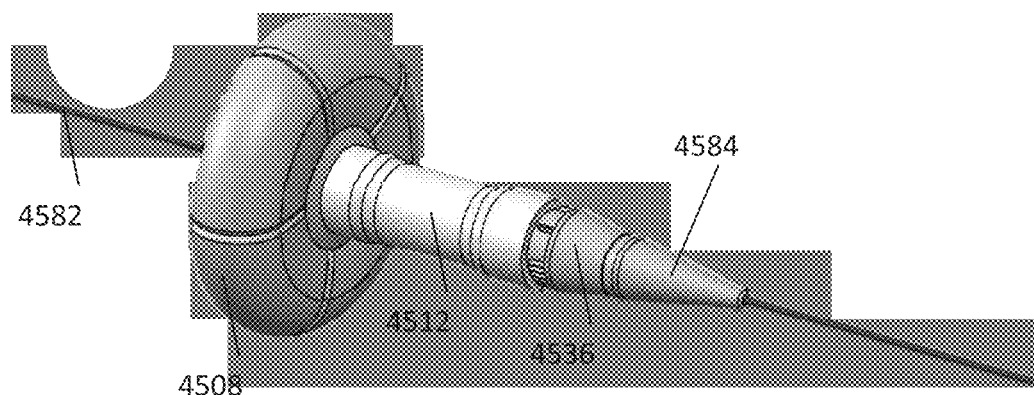
FIG. 45B is a simplified schematic side view of a pushing device within an outer tube attached to an inner bolster where a portion of the pushing device protrudes through the outer tube, according to some embodiments of the invention.

In some embodiments, a portion of a pushing device is sized to protrude from the outer tube. FIG. 45A is a simplified schematic side view of a pushing device 4580 including a tapered end 4584, according to some embodiments of the invention. FIG. 45B is a simplified schematic side view of a pushing device within an outer tube 4512 attached to an internal bolster 4508 where a portion of the pushing device protrudes through the outer tube, according to some embodiments of the invention. In some embodiments, tapered end 4584 which protrudes from outer tube 4512 gradually opens and/or dilates stoma as the outer tube is inserted, for example reducing trauma of installation of the device on the stoma.

FIG. 46A is a simplified schematic side view of a pushing device 4680, according to some embodiments of the invention. FIG. 46B is a simplified schematic side view of a pushing device within an outer tube 4612 attached to an internal bolster 4608 where a portion of the pushing device protrudes through the outer tube, according to some embodiments of the invention.

In some embodiments, pushing device 4680 attaches to portions of the device using a screw attachment or other type of attachment optionally other than sizing (e.g. snap-lock connection, adhesion etc.). In some embodiments, pushing device 4680 includes thread 4681, for example, for screw-mechanism attachment for attachment to a portion of the device (e.g. inner bolster 4608). Alternatively, in some embodiments, additional or alternative connection between the pushing device and the device are employed, e.g. snap lock, gluing.

In some embodiments, an incision is made from the stomach to the outer abdominal surface of a patient with a threaded needle. A loop 4683 (e.g. of thread, wire, cord) is attached to a suture and pulled through the incision, a tapered end 4484 (also herein termed "dilator") of the pushing device acting as a dilator, dilating tissue e.g. to create a stoma.

At, 4206, in some embodiments, an outer tube within the stoma is connected to a bolster. In some embodiments, once the outer tube is in position the external bolster is attached to the outer tube.

FIG. 47 is a simplified schematic side view of an ostomy device 4700 where an external bolster 4710 is being attached to an outer tube 4712, according to some embodiments of the invention. In some embodiments, pulling force F1 applied to an external element and a pushing force F2 acting on external bolster 4710 act to connect outer tube 4712 (optionally connected to an internal bolster 4708) to external bolster 4710 e.g. with a by an interference mechanism (e.g. push-lock mechanism). Alternatively, in some embodiments other forces are applied to connect components e.g. torque to connect components with screw connectors.

In some embodiments, the internal bolster is attached to the outer tube after the tube is inserted into the stoma. The external bolster is then connected to the outer tube.

In some embodiments, the outer tube is not inserted into the stoma from the lumen, the outer tube (optionally pre-attached to an external bolster) is inserted from outside the patient into the stoma, and, in some embodiments, the internal bolster is then connected to the tube. FIG. 48 is a simplified schematic section view of device installation including insertion of an outer tube 4812 into a stoma 4805, according to some embodiments of the invention. In some embodiments, outer tube 4812 and an internal bolster 4808 are connected by concurrent insertion of the outer tube 4812 into stoma 4805 by applying a force F2 and pulling by a force F1 applied to an elongated element 4882.

Alternatively, in some embodiments, outer tube 4812 is inserted into a stoma, from outside the patient, followed by connection of bolsters to the outer tube.

In some embodiments, an internal bolster connected to an outer tube is inserted into the stomach through the esophagus in a first direction (bolster first) with respect to the esophagus walls and then rotated inside the stomach for insertion in the opposite direction (outer tube first) to first direction (with respect to the stoma walls).

In some embodiments, the internal bolster is permanently attached (e.g. glue and/or injection molding) to the tube and/or internal bolster and outer tube are one part.

FIG. 49C is a simplified schematic cross sectional view of an internal bolster 4908 connected to an outer tube 4912 being inserted through an esophagus 4986, according to some embodiments of the invention.

In some embodiments, one or more portion of internal bolster 4908 bends and/or pivots (e.g. one or more petal is hingendly attached) contracts under pressure exerted by walls of the esophagus 4986. In an exemplary embodiment, petals 4964 elastically deflect towards outer tube 4912.

In some embodiments, once an internal bolster connected to an outer tube (e.g. 4912 and 4908) reach the lumen (e.g. stomach) the internal bolster connected to the outer tube is positioned and inserted into a stoma, tube first. FIG. 49D is a simplified schematic cross sectional view of an outer tube 4912 within a stoma connected to an internal bolster 4908, according to some embodiments of the invention. FIG. 49B illustrates an inner bolster 4908 where the bolster contacts patient tissue (stomach wall) at a distance from an opening of stoma 4905 into the stomach.

Returning now to FIG. 42, at 4208, once the body of the device is installed, an inner tube portion is inserted.

Exemplary Materials

In some embodiments, an internal bolster and/or external bolster and/or outer tube (e.g. as described here) include and/or, and the internal bolster and/or outer tube optionally includes material in one or more portion. In some embodiments, an inner tube portion includes silicone and/or polyurethane, optionally with radiopaque material in one or more potion. In some embodiments, rigid portion/s of the device for example, connectors (e.g. as described herein) include plastic/s, for example acrylonitrile butadiene styrene (ABS), polyamide (PA), polycarbonate (PC), polyethylene (PE).

Exemplary Detailed Method of Use

Figure 50A:
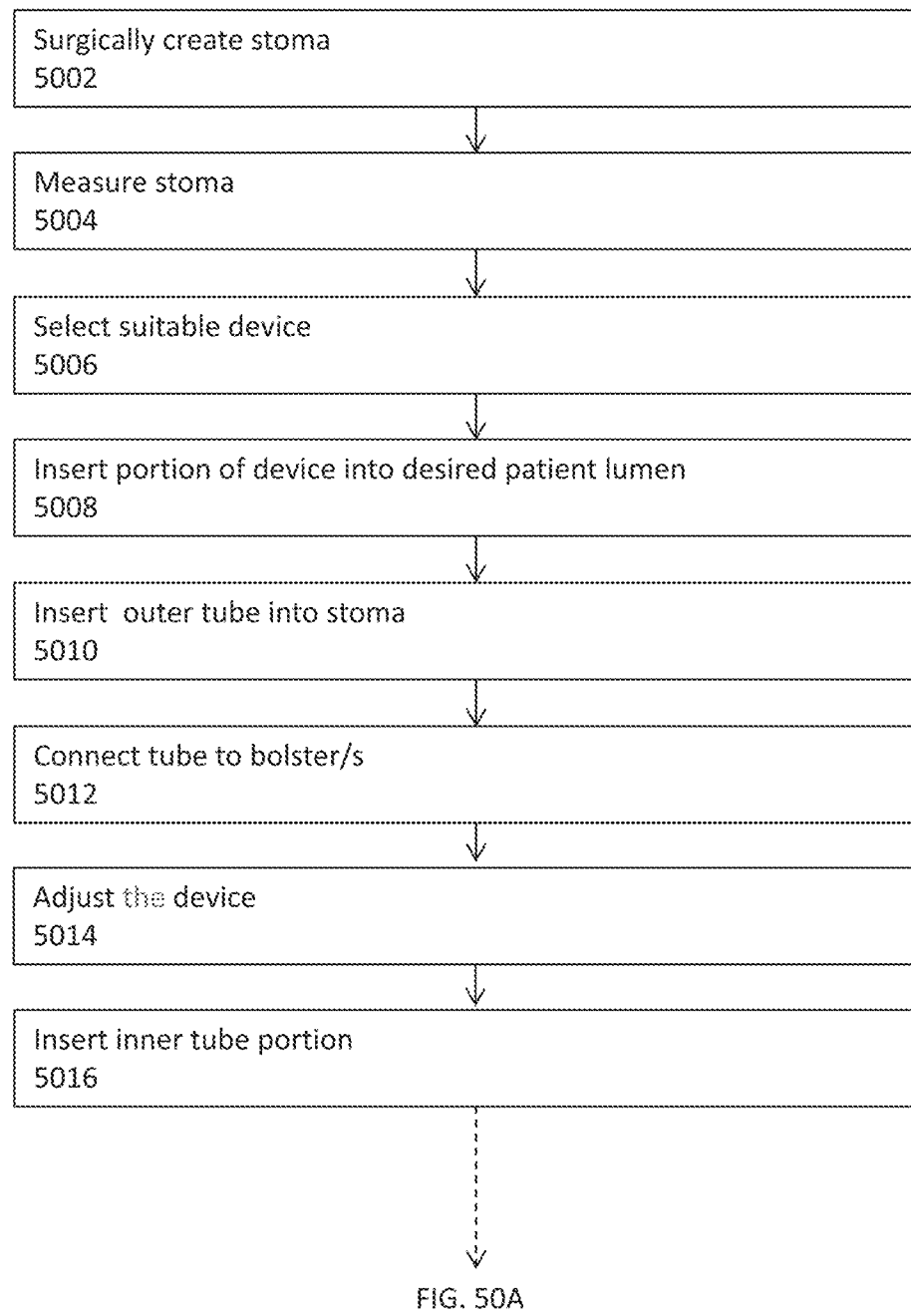
FIGS. 50A-50B are flow charts of a method of use of an ostomy device, according to some embodiments of the invention.
Figure 50B:
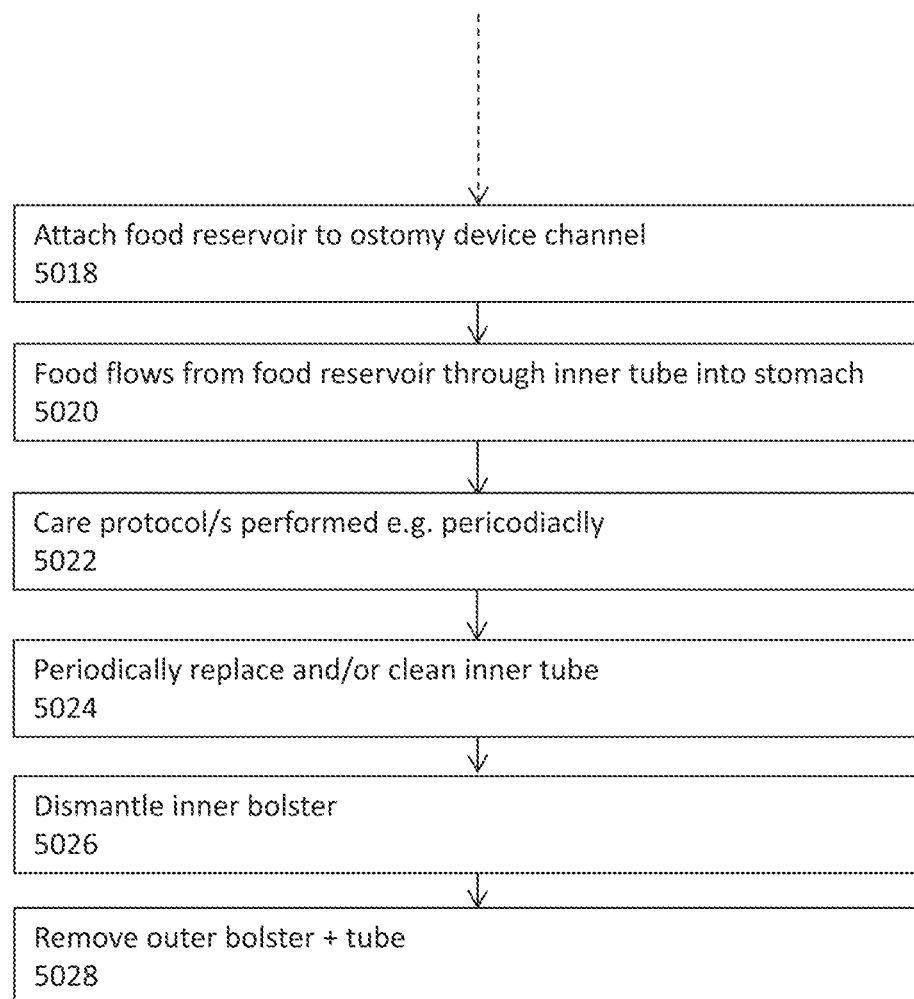

FIGS. 50A-50B are flow charts of a method of use of an ostomy device, according to some embodiments of the invention.

At 5002, in some embodiments, a stoma is surgically created between a desired lumen (e.g. stomach) and a patient outer abdominal surface. In some embodiments, the stoma site measured (e.g. a stoma position is selected based on measurement), for example, imaging, e.g. ultrasound and/or endoscopy and/or CT and/or MRI and/or X-ray imaging.

At 5004, in some embodiments, the surgically created stoma is measured, optionally during creation of the stoma, for example, a length of the stoma is measured. In some embodiments, during surgical creation of the stoma, an element (e.g. needle) is inserted between the stomach and the outer abdominal surface of the patient. In some embodiments, markings on the needle (e.g. numbers, different colors) are used to measure the stoma (e.g. a stoma length). In some embodiment, measurement is taken from within the lumen (e.g. using endoscopic visualization) and/or from outside the patient. In some embodiments, the needle is anchored inside the stomach and measurement of a stoma length (e.g. using markings on the needle) is only taken at the abdominal outer surface of the patient. In some embodiments, a sheath with markings is inserted into the stoma, and measurement is made using the markings on the sheath. In an exemplary embodiment, a needle within a sheath (the sheath including markings) is inserted into tissue. In some embodiments, measurement of the stoma is alternatively or additionally made during imaging.

At 5006, in some embodiments, a device is selected, optionally based on measurement of the stoma. In some embodiments, a length of an outer tube is selected based on measurements, for example, of the stoma length and/or of patient anatomy around the stoma (e.g. stoma site). In some embodiments, a length of the outer tube is selected to approximately for a length of the stoma, for example, a length of the tube being 10% or 20% or 30% or 40% longer or shorter than the stoma. In some embodiments, a length of the tube is selected to be longer than the stoma, for example 30% or 20% or 30% or 40% longer, for example, to allow for swelling of tissue surrounding the stoma. In some embodiments a size and/or shape and/or type of inner and external bolster are selected based on measurement and/or on treatment type and/or other patient parameters. In some embodiments, the device is selected based on an age and/or weight of a patient and/or prescribed feeding protocol (e.g. time, amount) and/or prescribed feed type.

At 5008, in some embodiments, one or more portion of the device (e.g. as described herein) is inserted into a desired patient lumen (e.g. the stomach).

At 5010, in some embodiments, the outer tube is inserted into the stoma. Optionally, in some embodiments insertion of the outer tube into patient tissue creates and/or or dilates the stoma.

At 5012, in some embodiments, one or both bolsters are attached to tube, where at least one bolster is attached to the tube after the tube is inserted into the stoma.

At 5014, in some embodiments axial dimensions of the device are adjusted, for example, compensating for missmatch between a length of the outer tube and length of the stoma. For example, in some embodiments, position of an inner bolster and/or outer bolster are changed with respect to the outer tube, thereby changing a minimum dimension between the bolsters. In some embodiments, compensating is by up to 2 mm, or up to 5 mm, or up to 10 mm, or lower, or higher, or intermediate values or ranges.

At 5016, the device is optionally adjusted and/or self adjusts, for example to fit the patient. Optionally, the device may be passively adjusted (e.g. self adjusting) and/or actively adjusted. For example the distance between an inner and an outer bolster (e.g. the axial extent of the device) may be lengthened and/or shortened. Alternatively or additionally, an angle between a bolster and an axis of a tube may be adjusted. Alternatively or additionally, a radial extent of a petal and/or a radial distance between a stoma and a contact zone of a petal and tissue may be adjusted.

In some embodiments, the axial dimension of the device may be adjusted. For example, as described in FIGS. 27, 28A-28D, 29A-29B, 30, 31A-31B and 32A-32B.

In some embodiments, one or more bolsters may be adjusted be mounted on a variable angle joint. For example, the bolster may passively adjust itself to balance pressure around the stoma. Alternatively or additionally, the bolster may be actively adjusted. For example, a variable angle joint may have a control mechanism. Optionally a user may set the angle of the bolster according the needs (for example due to the anatomy of the patient and/or the placement of the stoma). After the angle of the bolster has been set, the bolster may be tightened to retain it at the chosen angle.

In some embodiments the width and/or the stiffness of a bolster and/or an associated petal and/or a force of a bolster on the patient and/or around the stoma may be adjusted. For example, petals may be elastic and self adjust to the shape of the surface of the tissue around the stoma. Alternatively or additionally, there may be a mechanism to tighten or loosen a bolster and/or a petal thereof. For example a threaded element and/or a wedge may be used to change the angle at which a petal extends from a bolster.

In some embodiments a bolster may be adjusted in use to temporarily reduce pressure at a certain location (for example where there is swelling and/or sensitivity and/or infection and/or a sore). Alternatively or additionally, a device may be adjusted prior placement and/or during placement according to the particular characteristics of a patient that are known and/or have been measured.

In some embodiments, an inner tube is inserted into the outer tube, forming a channel between outside the patient and the lumen. In some embodiments, the inner tube extends through the stomach into the jejunum. In some embodiments, the inner tube during and/or after insertion, is connected to the external bolster. In some embodiments an opening of the tube (for example the outer opening) may be attached to, covered by and/or within the bolster (for example the external bolster). Alternatively or additionally a tube may extend through a bolster. For example the inner tube may extend outward through the external bolster. For example the inner tube may extend outward from the patient less than 1 cm and/or between 1 cm to 1 m and/or between 1 m to 5 m or further.

In some embodiments, insertion and/or positioning of parts of the device into the lumen and/or stoma is assisted by imaging e.g. endoscopic imaging, ultrasound imaging. In some embodiments, one or more portion of the device includes radiopaque material and/or radiopaque marker/s and imaging includes, e.g. X-ray and/or CT and/or MRI.

At 5018, in some embodiments, the patient is fed, at discrete feeds or continuously by attaching a food reservoir to the ostomy device, such that, at 5020, food flows from the reservoir into the patient through the inner tube. In some embodiments, a food pump controls dispensing of food from the food reservoir into the patient.

At 5022, in some embodiments, various care protocols are performed by a caregiver and/or the patient e.g. periodically, for example, in some embodiments, the device is rotated (e.g. by rotating the outer bolster) periodically, for example to prevent encapsulation of the inner bolster into the lumen (e.g. stomach inner wall), for example, to change portions of tissue under pressure from the inner and/or outer bolster. For example, in some embodiments, an outer portion of the device is periodically cleaned.

In some embodiments, fit of the device to the patient anatomy is periodically checked and/or adjusted.

For example, in some embodiments, freedom of movement of the device in situ is manually checked, in order to ascertain what level of pressure the inner bolster is applying to the lumen inner wall. In some embodiments, points of contact of the outer bolster and/or tissue around and/or under the outer bolster and/or a level of elastic deflection of outer bolster is visually checked to ascertain pressure levels of the bolster/s on patient tissue (e.g. outer abdominal surface and/or stomach lining).

For example, in some embodiments, upon patient weight change and/or a change in level of tissue swelling and/or signs of physiologically unacceptable pressure between patient tissue and the device, a minimum axial separation between bolsters is adjusted (e.g. as described herein), for example, by a caregiver.

In some embodiments, the inner tube is flushed and/or massaged to prevent blockage.

At 5024, in some embodiments, the inner tube is removed and the cleaned and/or replaced while the bolsters and outer tube remain in position within the patient.

At 5026, for example, when an ostomy device is no longer required and/or when the ostomy device requires replacement, the inner bolster is dismantled by disassembling the inner bolster into a plurality of portions. In some embodiments, the dismantled portions of the internal bolster are free within the lumen (e.g. stomach), for example, then passing through the digestive system. Alternatively, in some embodiments, the disassembled portions are then removed from the lumen (e.g. by pulling through the stoma).

Alternatively, in some embodiments, the internal bolster is sufficiently flexible to be removed by pulling on the tube from outside the stomach. Alternatively, in some embodiments, the device is dismantled during an endoscopic procedure where, for example, the inner bolster is detached from the tube and, is optionally then removed through the esophagus or the inner bolster attached to the tube is removed through the esophagus.

At 5028, in some embodiments, the outer tube and outer bolster are then removed. In some embodiments, the stoma then naturally closes. Alternatively, in some embodiments, the stoma is then surgically closed. Alternatively, in some embodiments, a new ostomy device is installed.

In some embodiments, the ostomy device (e.g. as described herein) is used for purposes other than PEG feeding. For example, jejunum feeding, collection of waste from the colon, connection of two internal lumens.

Figure 51:
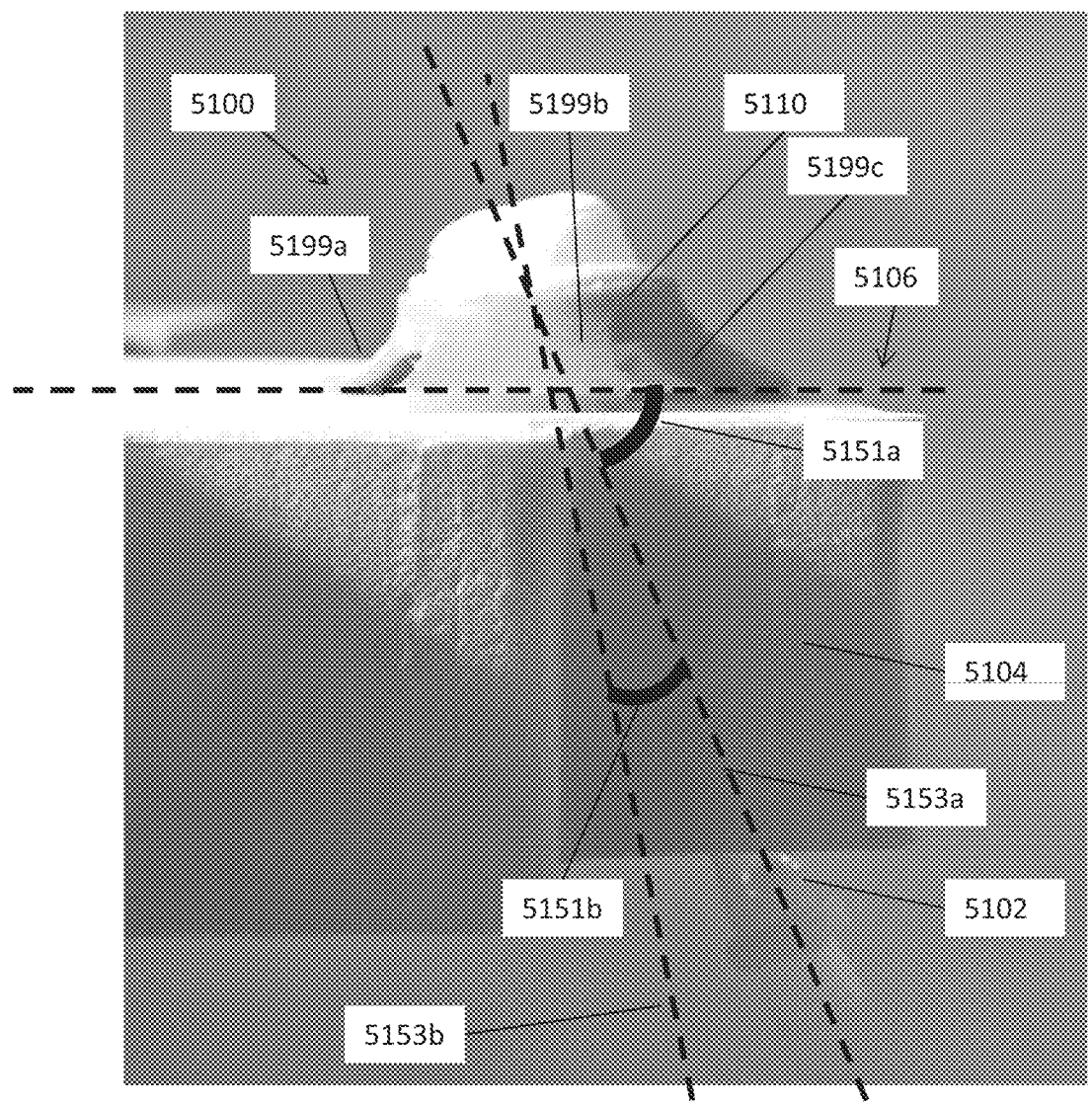
FIG. 51 is a photograph illustrating a device with a pivoting external bolster inserted at an angle through simulated tissue in accordance with some embodiments of the current invention.

FIG. 51 is a photograph of a device inserted at an angle through simulated tissue in accordance with some embodiments of the current invention. Optionally the device includes an external bolster attached by variable angle joint to a tube. In some embodiments, a PEG device may include a variable angle joint, for example a ball joint. Optionally, the ball joint may join an outer bolster base 5110 and/or petals 5199*a*, 5199*b* and 5199*c* to a tube 5102. Optionally petals 5199*a*, 5199*b* and/or 5199*c* contact a surface 5106 of tissue 5104. For example, petals 5199*a*, 5199*b* and/or 5199*c* may prevent bolster 5100 and/or tube 5102 from being pulled into the stoma. Alternatively or additionally, one or more extensions may contact a surface 5106 of tissue 5104. For example, the extension may prevent bolster 5100 and/or tube 5102 from being pulled into the stoma. For example an extension may have a dome shape.

In some embodiments, a variable angle joint may improve the fit of a bolster 5100 to an outer surface 5106 of a patient. For example, sometimes an opening, a stoma and/or a tube 5102 may pass through tissue 5104 at an acute angle 5151*a* to surface 5106. The ball joint may allow adjustment of an angle 5151*b* between an axis 5153*b* of bolster 5100 and an axis 5153*a* of tube 5102. Optionally rotation of the variable angle joint may at least partially compensate for the difference between angle 5151*b* and a line normal to surface 5106. For example compensation make axis 5153*b* of bolster 5100 closer than axis 5153*a* of tube 5102 to a normal to surface 5106.

Figure 52:
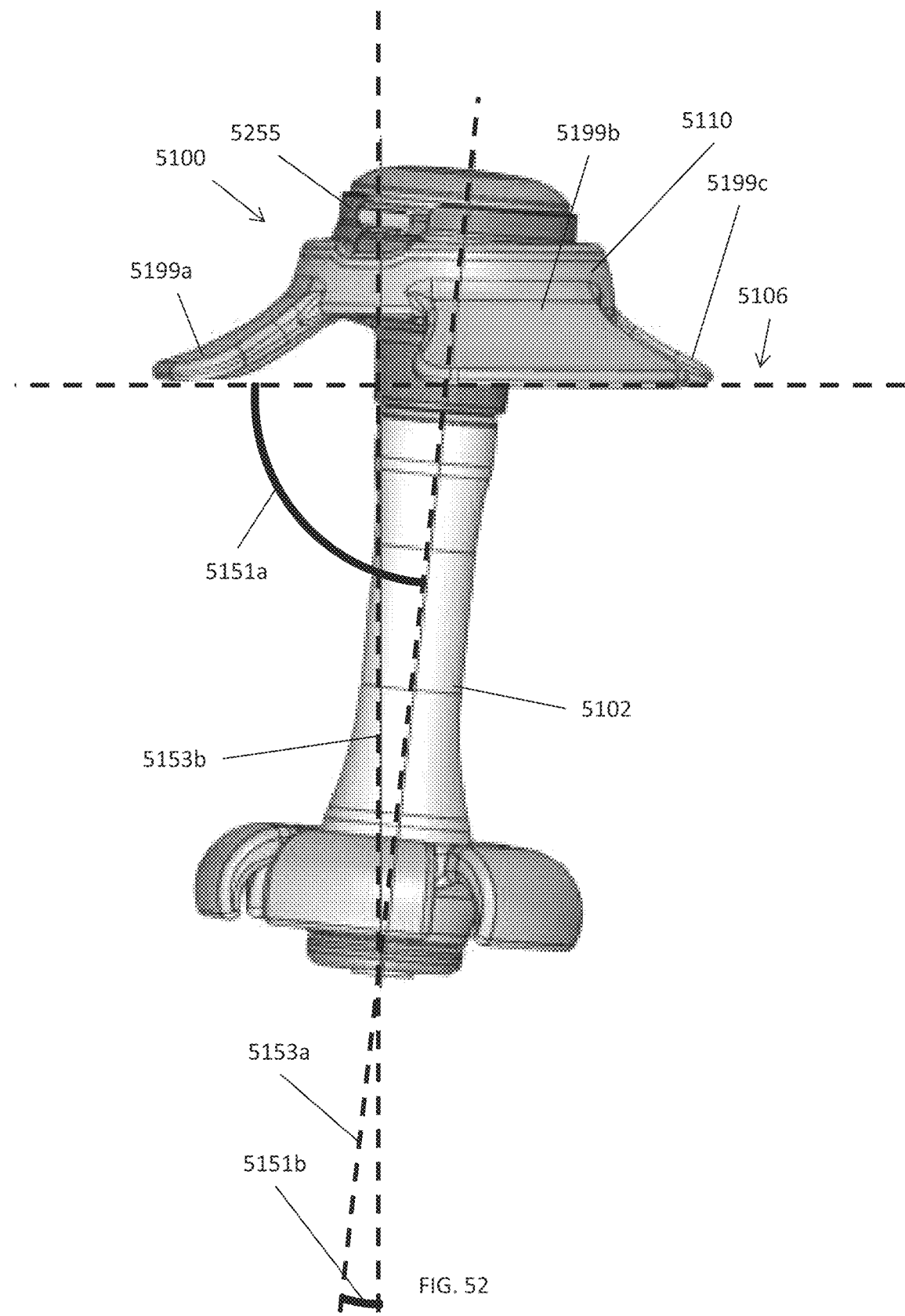
FIG. 52 is a simplified perspective view of a device with a pivoting external bolster inserted at an angle to an external body surface in accordance with some embodiments of the current invention.
Figure 53:
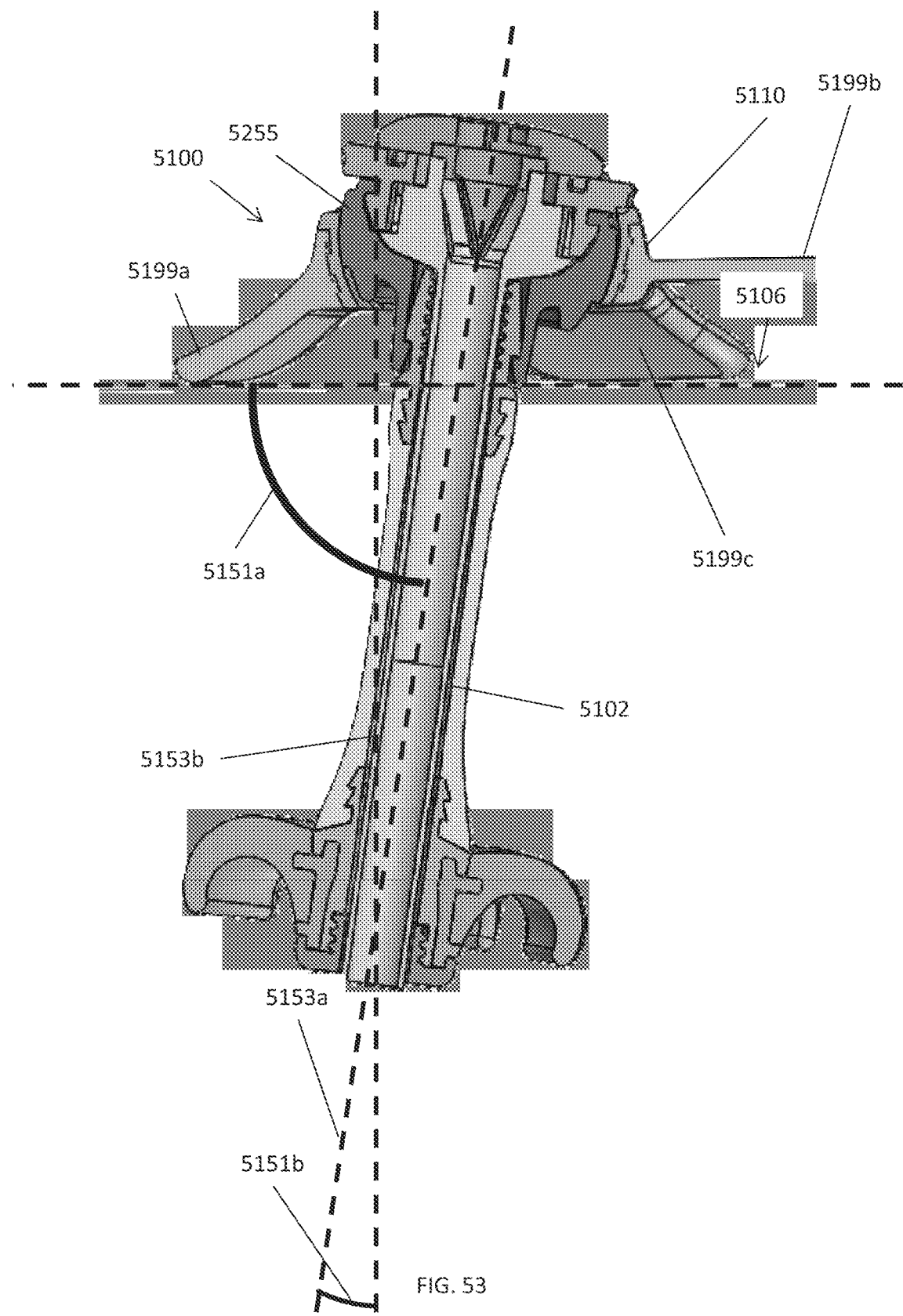
FIG. 53 is a cross sectional view of a device with a pivoting external bolster inserted at an angle to an external body surface in accordance with some embodiments of the current invention.

FIGS. 52 and 53 are perspective and cross sectional views of a device with a pivoting external bolster inserted at an angle to an external body surface in accordance with some embodiments of the current invention. In some embodiments bolster base 5110 has the form of a skirt that rotates over a ball joint 5255 over a range of angles.

In some embodiments angle 5151*b* may be passively adjusted to equalize the force on petals 5199*a*, 5199*b* and 5199*c*. For example, base 5110 may float freely on joint 5255. Optionally, when there is an increased force on one of the petals 5199*a*, 5199*b* or 5199*c* the excess force will create a torque rotating bolster 5100 away from that side. The resulting rotation optionally balances the forces on the petals 5199*a*, 5199*b* and 5199*c*. Optionally angle 5151*b* between bolster 5100 and axis 5153*a* may help compensate for short term changes in surface 5106, for example swelling on one side of the stoma. Alternatively or additionally, there may be a biasing mechanism that biases the bolster to a certain position, for example coaxial to the tube. For example an elastic element for example a spring and/or an elastomeric element may bias the angle such that deflections from the biased angle require progressively more force for progressively larger deflections.

In some embodiments, friction between bolster base 5110 and joint 5255 may be chosen to allow movement to compensate for variations in angle 5151*a* of axis 5153*a* of tube 5102 and surface 5106 but to avoid shifting of tube 5102. Optionally, friction between bolster base 5110 and joint 5255 may be low allowing compensation to short term movements for example due to movement of the patient and/or due to movement of internal organs of the patient. Alternatively or additionally, a variable angle joint may include an adjustment mechanism. For example, an adjustment mechanism may tighten the joint making it resist changing its angle once set. For example, the adjustment mechanism may include a tightening means such as a screw. For example the adjustment mechanism may limit the angular range of the bolster.

Figure 54:
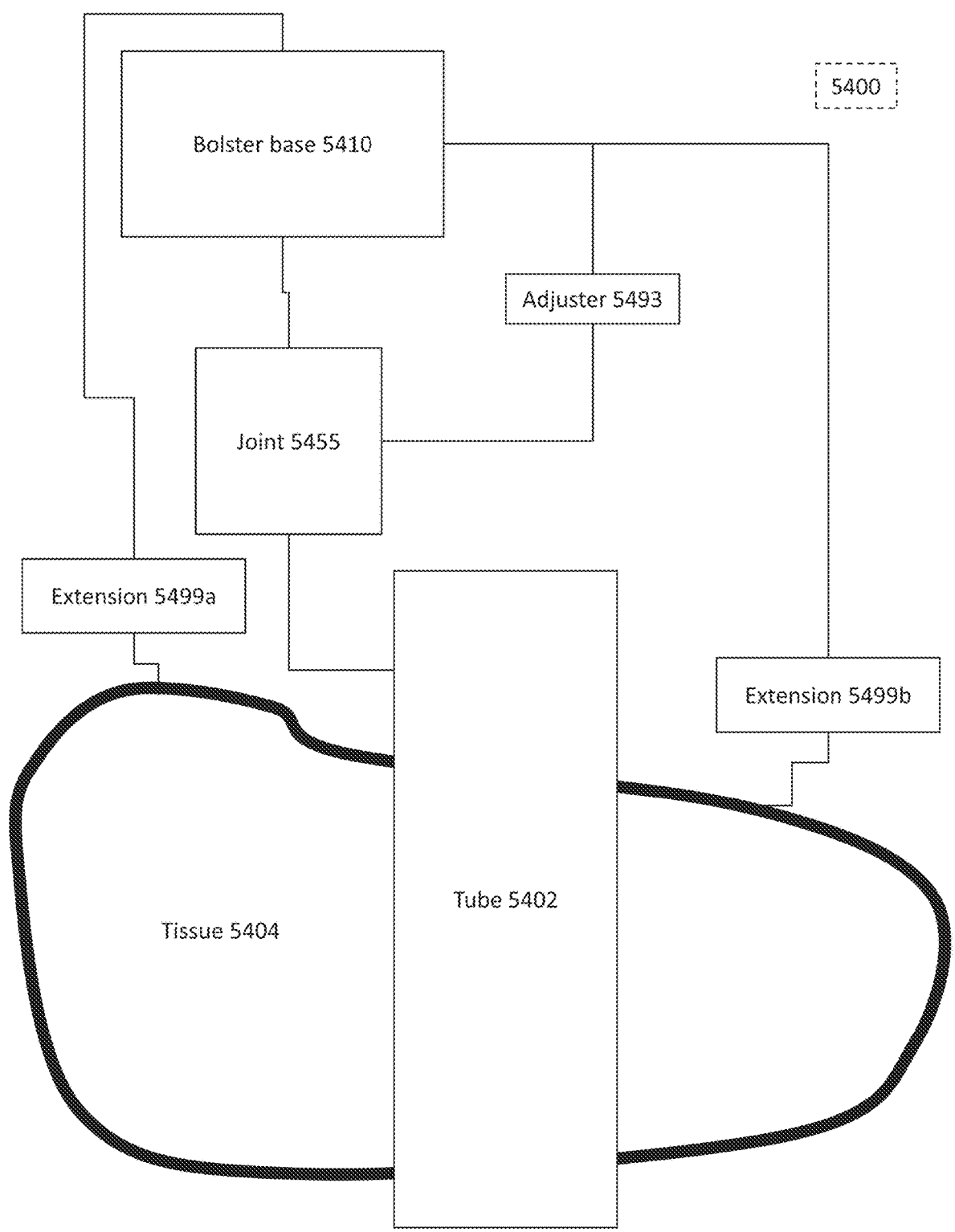
FIG. 54 is a block diagram of an adjustable bolster 5100 in accordance with an embodiment of the current invention.

FIG. 54 is a block diagram of an adjustable bolster 5100 in accordance with an embodiment of the current invention. In some embodiments, one or more extensions 5499*a*, 5499*b* are attached to a bolster base 5410. Base 5410 optionally swivels on a joint 5455. Joint 5455 is optionally attached to a tube 5402.

In some embodiments, when bolster 5400 is in use, tube 5402 passes through a stoma and/or an opening in tissue 5404. Optionally extensions 5499*a*, 5499*b* contact a surface of tissue 5404 and/or prevent bolster 5400 from being pulled into the stoma and/or the opening.

In some embodiments, swiveling bolster 5400 may allow it to adjust to a surface of tissue 5404. For example, if tube 5402 is at an angle to the surface of tissue 5404, bolster 5400 may swivel so that a plane of extensions 5499*a*, 5499*b* is parallel to the surface. For example, bolster 5400 may swivel so that an axis of bolster 5400 is perpendicular to the surface of tissue 5404.

Optionally an adjustor 5493 mediates the connection between bolster base 5410 and joint 5455. For example adjuster 5493 may include a screw that when tightened increase a force of contact and/or a coefficient of friction between joint 5455 and base 5410. Increasing friction may for example fix the position of base 5410 with respect to joint 5455 hindering further swiveling. Alternatively or additionally, adjuster 5493 may allow swiveling, but increase a resistance thereto.

In some embodiments, a tube 5402 may be flexible. For example, swiveling of bolster 5400 around joint 5455 may compensate for an angle between an outer axis of tube 5402 and a normal to the surface of tissue 5404. Alternatively or additionally, tube 5402 may be rigid and/or have a right cylindrical form.

Measuring Tissue Placing Outer Tube

Figure 55A:
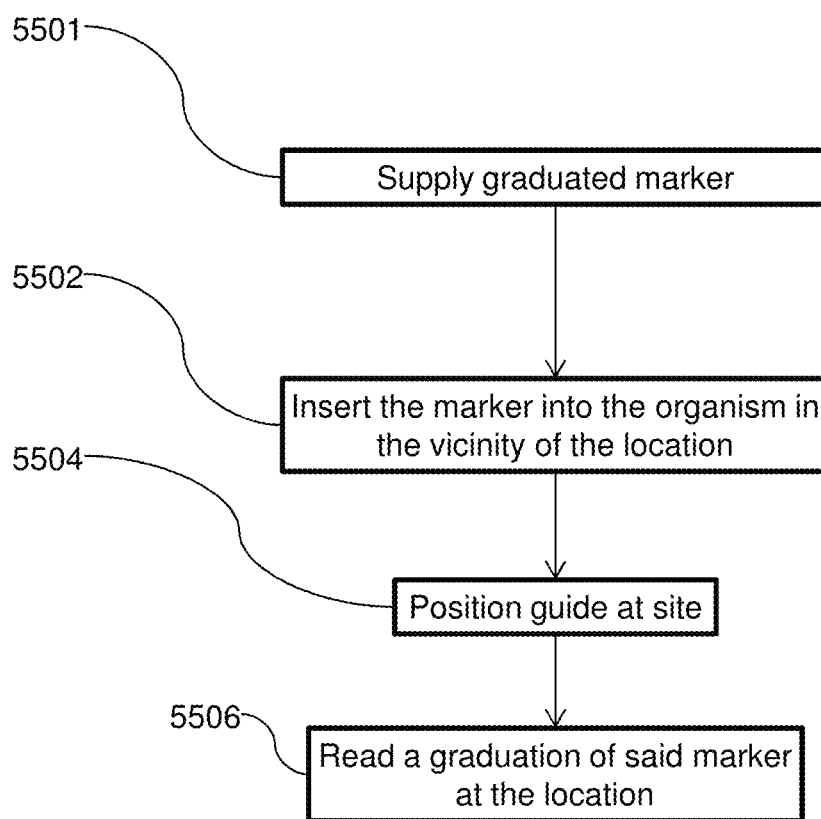
FIG. 55A is a flow chart illustration of a measuring the depth from a base site to a location inside a living organism in accordance with some embodiments of the current invention.

FIG. 55A is a flow chart illustration of a measuring the depth from a base site to a location inside a living organism in accordance with some embodiments of the current invention. For example the device may be used to measure a distance between two ends of a stoma and/or a port and/or a passageway into living tissue and/or a lumen of living organism. Optionally a marker (optionally including graduations) is inserted into the organism to the measurement location. For example, the marker may indicate a distance to a guide element. Optionally the guide element is placed at a base site. The marker may be positioned by viewing and/or sensing in the lumen. For example, placement of the marker may be without stressing the lumen tissue. The distance from the location in the organism to the base site is optionally measured by reading a graduation of the marker at the location inside the organism. For example, the method may be used to measure the length of a stoma and/or a port from an opening outside the lumen to an opening on the inner wall of the lumen.

In some embodiments, an instrument including the graduated marker and the guide may be supplied 5501. For example the graduated marker may be positioned on a distal portion of a stylet. The stylet optionally includes a pointed distal end. For example the graduated marker may be located on the stylet proximal to the point. Optionally the guide may be located on the stylet proximal to the marker. For example, the guide may include a shoulder of the stylet and/or the graduations may indicate a distance between the marker and the shoulder of the stylet. Optionally, the marker may be inserted 5502 into the organism. For example, distal point of the stylet and/or the marker may be inserted into the organism in a vicinity of the measurement location for example by piercing of and/or insertion through tissue surrounding the location.

In some embodiments, the guide may be positioned 5504 at the base site. A graduation on the marker nearest to the location is optionally read 5506, indicating the distance from the location to the guide and/or base site. For example, the stylet may be inserted until the shoulder is positioned 5504 at a skin insertion site including the base site. A graduation nearest the location to be measured inside the organism may be identified and/or read 5506 to indicate a distance between the internal location and the base site.

In some embodiments a single device may be used for forming and measuring a stoma. For example, the device may include an insertion needle and a graduated sleeve. The needle point may form the distal tip of the device. Proximal to the point graduations on the sleeve may indicate a distance to a guide connected to the sleeve proximal to the graduations. For example, the guide may include a shoulder. Optionally the needle is used to pierce tissue surrounding a lumen (for example the stomach and/or intestine). The needle and/or marker are optionally inserted into the lumen. Optionally piercing and inserting form a stoma between an insertion point on the skin and the lumen. In some embodiments, once the sleeve has entered the lumen, the needle point may be pulled back into the sleeve, for example to prevent the needle point from further puncturing the lumen.

In some embodiments, the sleeve is inserted until a guide of the device reaches an insertion point on an outer surface (e.g. skin) of the subject. For example, the guide may include a proximal shoulder of the device and/or the device may be fully inserted until the shoulder is adjacent to (e.g. flush to) the skin surface. Alternatively or additionally, a guide may include a second set of graduations (indicating, for example how far the sleeve has been inserted into the subject). The sleeve is optionally partially inserted into the subject until the second set of graduations is adjacent to the skin of the subject.

In some embodiments, the distal end of the sleeve protruding into the lumen may be viewed. For example, an viewing device may be supplied in the lumen (for example the imaging device may include a camera mounted on an endoscope). The viewing may optionally be from outside (e.g. through an opening during operation on the lumen). The viewing device may be used to identify and/or read a marking on the sleeve closest to the lumen wall. The marking may include graduation optionally indicates the length of the stoma from the skin surface to the inner wall of the lumen.

In some embodiments, the stoma created in the measuring process and/or the sleeve may be used for insertion of an ostomy device, for example as described hereinabove in FIGS. 50A-50B. For example, the graduated measurement sleeve may be used as a channel for inserting a drawstring into the lumen for drawing a pulling device and/or loop into the lumen (for example through a mouth and/or a trachea). For example, the ostomy device may be passed through and/or placed in the stoma created during the measuring. Optionally, a measurement of the length of the stoma, for example made as described in FIGS. 55A-55B, may be used to select a low profile ostomy device. For example, the first device inserted and/or anchored in the stoma (for example the first access port (e.g. PEG tube) inserted into the stoma) may be a low profile device. Optionally measuring the stoma and insertion of the initial port (e.g. PEG) may be accomplished in a single procedure.

In some embodiments, a stoma length may be measured without compressing the associated tissue. For example, the measurement of stoma length of uncompressed tissue may be used a safe length for a PEG. For example a PEG fitted to the safe length may fit snugly with no and/or minimal and/or negligible and/or small pressure on the tis sue.

In some embodiments, a stoma length may be measured before inserting a PEG device. For example, based on the measurement, an initial PEG device placed during the procedure producing the stoma may be a low profile device.

Figure 55B:
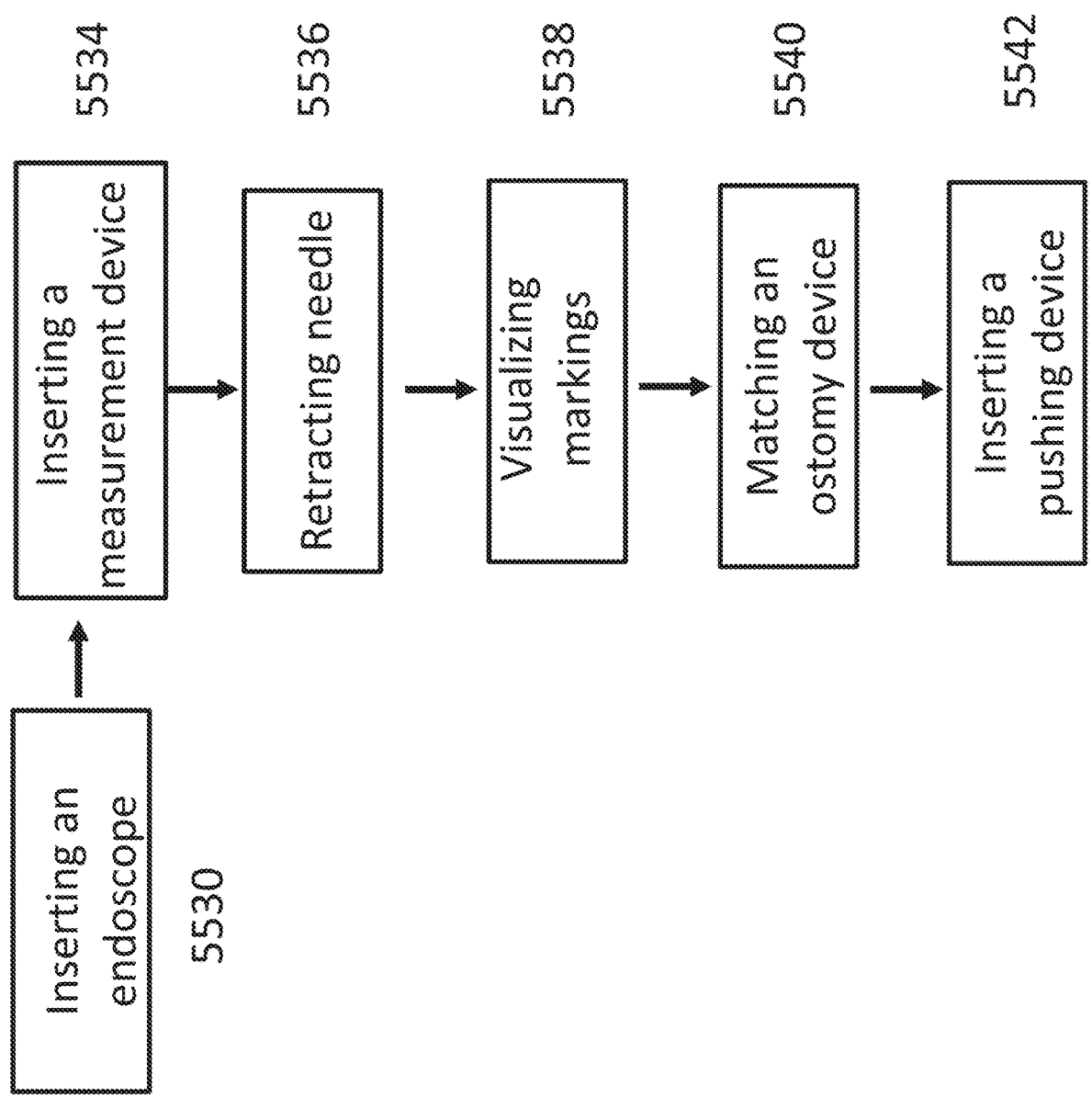
FIG. 55B is a flow chart of a process for measuring the depth from a base site on the outer surface of the skin to a location inside a stomach in accordance with some embodiments of the current invention.

Reference is now made to FIG. 55B depicting a process for measuring the depth of the stomach lumen from the outer surface of the skin, according to some embodiments of the invention.

According to some exemplary embodiments, an endoscope is inserted through the esophagus into the stomach at 5530. In some embodiments, the endoscope is connected to a camera for visualizing the inner surface of the stomach wall. In some embodiments, the endoscope is inserted to select a target site for creating a stoma at the stomach wall.

According to some exemplary embodiments, a measurement device having a needle is inserted through the outer surface of the stomach into the stomach lumen at 5534. In some embodiments, the measurement device punctures the stomach wall at a stoma target site that was selected using the endoscope. Optionally, the insertion of the measurement device creates the stoma opening. In some embodiments, the measurement device is inserted until reaching a stopping point on the measurement device. In some embodiments, the stopping point is positioned outside of the body and optionally marks a measuring reference.

According to some exemplary embodiments, once the stopping point on the measurement device is in contact with the outer surface of the skin, the needle within the measurement device is retracted at 5536. In some embodiments, retraction of the needle leaves an empty lumen within the measurement device.

According to some exemplary embodiments, the markings on the measurement device that are positioned within the stomach lumen are visualized at 5538. In some embodiments, the markings are visualized from within the stomach lumen by the endoscope. Alternatively, the markings are visualized by from outside using an imaging technique, for example an x-ray imaging technique, an MRI or CT. In some embodiments, the markings are color coded markings, optionally with dividing stripes between adjacent markings to allow, for example better visualization. In some embodiments each of the color markings encodes for a different depth or distance from the outer surface of the stoma. Optionally, each of the color markings encodes for a different depth or distance from the stopping point of the measurement device.

According to some exemplary embodiments, based on the marking that is positioned in the closest proximity to the inner surface of the stomach wall, an ostomy device is selected at 5540. In some embodiments, the length of the selected ostomy device matches the length of the marking, optionally the color coded marking that is visualized to be in the closest proximity to the inner surface of the stomach wall. In some embodiments, each color coded marking indicates a different length of an outer tube.

According to some exemplary embodiments, a pushing device is inserted into the stoma at 5542. In some embodiments, the pushing device is a guiding element which is sized and shaped to allow, for example to guide at least part of the ostomy device from the stomach lumen to the outer surface of the body through the stoma. In some embodiments, a leading thread or a leading wire is inserted from the outside through the stoma and the lumen of the measurement device into the stomach lumen. In some embodiments, the endoscope is connected to the leading thread and pulls the leading thread out from the mouth. In some embodiments, a loop positioned at a pushing device end is connected to the leading thread. In some embodiments, the leading thread is connected to a loop of a dilator of a pushing device, for example dilator 5880 shown in FIG. 58A. In some embodiments, after the connection of the pushing device to the leading thread, the leading thread pulls the pushing device through the esophagus and through the stoma. In some embodiments, the dilator is pulled through the stoma, while the inner bolster is kept inside the stomach lumen.

Figure 56A:
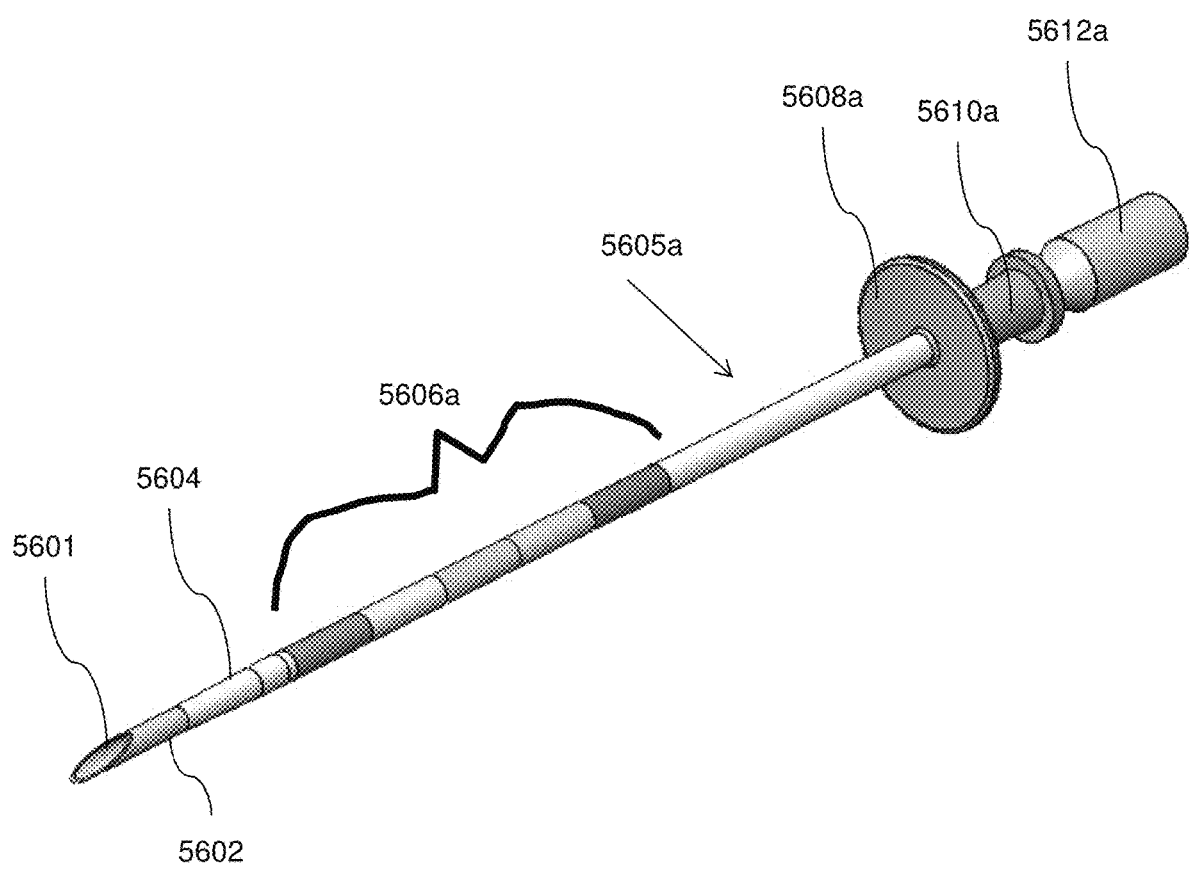
Figure 56B:
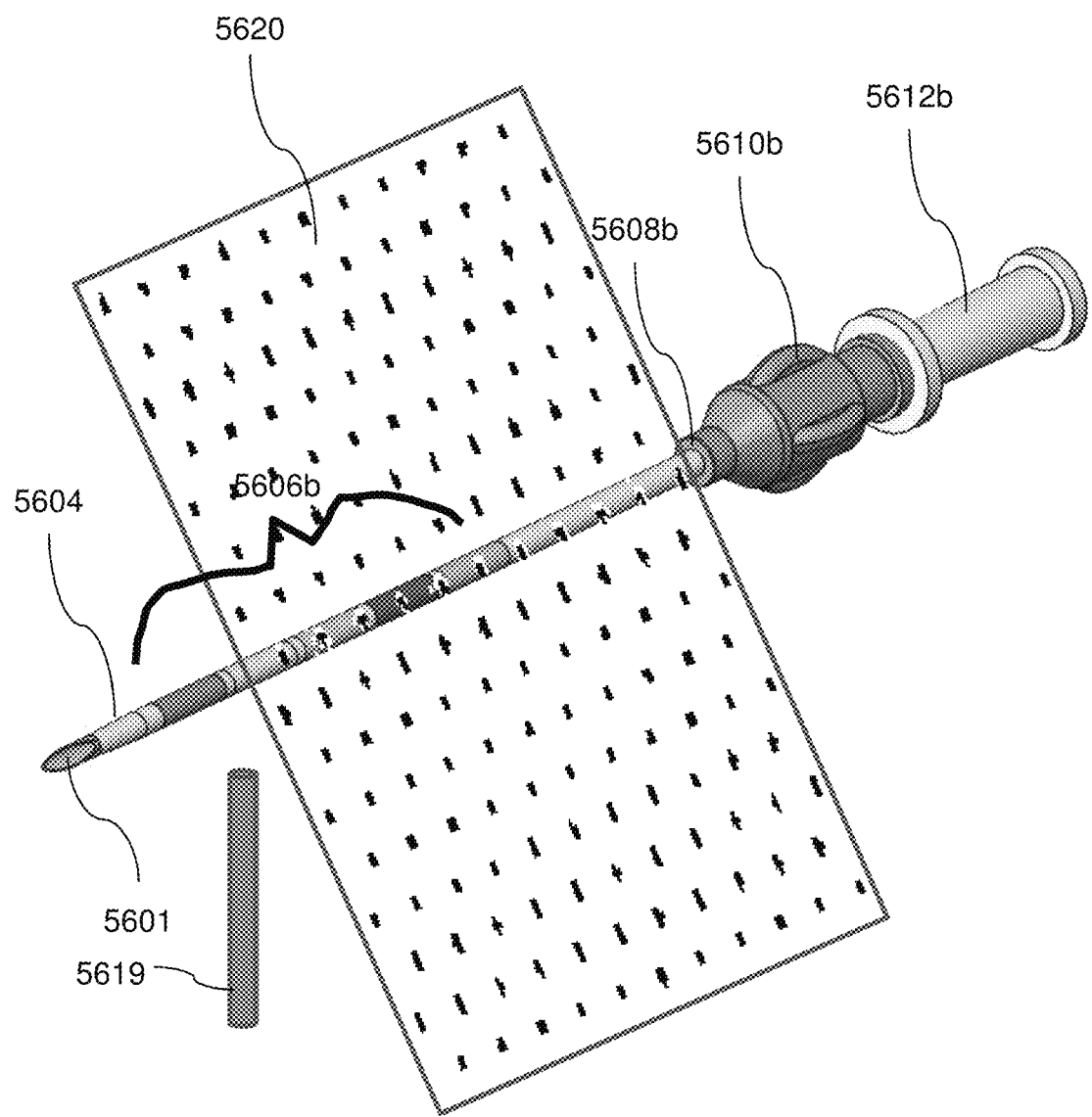

According to some exemplary embodiments, the leading thread is inserted through the lumen of the measurement device into the stomach and is connected to a pushing device already placed in the stomach. Alternatively, the pushing device is held within the stomach by the endoscope. FIGS. 56A-56C are perspective views of measurement sheaths and inserter needles in accordance with some embodiments of the current invention. In some embodiments a distal end of a measurement device forms a sharp tip 5601. Optionally the tip is connected to a needle shank 5602. For example, shank 5602 may pass through a sleeve 5605*a*. The sleeve optionally includes a tapered distal section 5604. Along the sleeve and/or needle, there may be a graduated section 5606*a*. Proximal to graduated section 5606*a* there is an optional guide 5610*a*.

In some embodiment pointed tip 5601 and/or shank 5601 are optionally hollow. Alternatively or additionally a pointed tip and/or shank may be solid.

In some embodiments, graduated section 5606*a* may include color coded bands. Optionally the bands may be one adjacent to another. Alternatively or additionally, there may be space between the bands. Alternatively or additionally other visible markers may be used such as lines and/or symbols and/or changes in the shape such as protrusions and/or etched portions and/or indentations. Active graduations may be supplied, for example visible and/or radio beacons may be used. Optionally a device may include multiple resolution graduations. For example low resolution color bands may be divided up by high resolution divisions for example lines. Multiple resolutions markings may allow for more precise measurements. Markers may include for example numbers and/or symbols.

In some embodiments a guide 5608*a* may include a shoulder. For example, at a time of measurement, sheath 5605*a* may be inserted through tissue into a lumen until the shoulder (e.g. guide 5608*a*) is flush with the skin of a user. Alternatively or additionally the proximal guide may include a graduated section. For example, the probe is inserted into tissue until a portion of the proximal graduated section is visible outside the organism and/or tissue being measured. The proximal graduation optionally will be read from outside the tissue to indicate what portion of the needle was passed into the tissue. Optionally, there may be a single internal marker (on the distal portion of the measurement device). The internal marker may be aligned with a location to be measured. For example, a viewing device (for example an endoscope) may be inserted into a lumen. The measurement device may be inserted through the wall of the lumen until the marker is seen through the endoscope flush with the wall of the lumen. With the marker located at the lumen wall the distance between the marker and the base site may be read from graduations on the proximal side of the measuring device.

In some embodiments a measurement device will be used to measure the length of a stoma for insertion of a PEG tube. For example, sharp tip 5601 and/or sleeve 5605*a* are inserted through abdominal skin and/or muscle and/or other tissue and/or through a stomach wall into a stomach cavity until a distal edge of guide 5608*a* is flush with the outer abdominal wall and/or part of graduated portion 5606*a* passes through the stomach wall into the stomach cavity. Optionally an imaging device in the stomach is used to identify the color band of graduated portion 5606*a* that is located at the edge of the inner wall of the stomach. For example, the length along sheath from guide 5608*a* to the color coded band may be the length of the stoma from the abdominal wall to the inner wall of the stomach. The needle may be removed from sheath 5605*a* and/or sheath 5605*a* may remain in the stoma for use in installing a PEG. For example a guidewire may be inserted through sheath 5605*a* into the stomach and/or pulled through the lumen to an opening (e.g. the mouth) where it may be connected to an insertion device (e.g. a dissector an obturator and/or a dilator) and/or a PEG tube which are optionally pulled into the stoma. Alternatively or additionally a marker may be on or in a needle. The marker may be visible through the sheath which is optionally transparent and/or translucent and/or made of a mesh through which the needle can be seen. The distance may be measured from the guide to the marker on the needle. In some embodiments, since the marker is position in the location through visual sighting and not by a force on the tissue, the tissue may be measured in an unstressed state.

Optionally in some embodiments measurement segments may be between 6 to 8 mm. For example, the length of the measurement segments may match the axial expandability of the PEG tube. For example for a PEG tube with a flexible bolster as described herein, the flexible bolster may adjust and/or compensate for changes of length of less than 10 mm. For a bolster with less ability to compensate, the graduations on the measurement tool (e.g. the measurement segments e.g. the color bands) may be smaller to get a more precise measurement. For example, the precision of the measurement may range between 30 to 50% of the axial compensation ability of the PEG and/or between 50 to 80% and/or between 80% to 100% and/or between 100% to 130% of the axial compensation ability of the PEG and/or bolsters. Alternatively or additionally a hollow needle may be used as a measuring device without a sheath. For example, bands may range between 0 and 1 mm long and/or between 1 to 4 mm long and/or between 4 to 8 mm long and/or between 8 to 10 mm and/or between 10 to 15 mm long.

In some embodiments a sheath handle 5610*a* is provided. For example, handle 5610*a* may be used for manipulation, insertion and/or extraction of sheath 5605*a*. In some embodiments a needle handle 5612*a* is provided. For example, handle 5612*a* may be used for manipulation, insertion and/or extraction of needle tip 5601 and/or shank 5602.

FIGS. 56B-56C illustrate an alternative embodiment of a measurement tool with a needle fully inserted and partially retracted respectively. For example the embodiment of FIGS. 56B-56C may include an alternative graduation portion 5606*b* guide 5608*b* and/or sheath handle 5610*b* and/or needle handle 5612*b*.

In some embodiments a measuring device, for example for a PEG stoma, may include a needle of 16G and ranging between 14 to 18 G. Optionally sheath may be 13 G and/or range between 11 to 15 G. Alternatively, a needle may be wider and thinner depending of the size of the lumen and the thickness and resistance of its walls for example the needle and sheath may differ for measuring different organs and/or lumens and/or the needle may be smaller for children than for adults. For example the needle may range between 10 to 13 G and/or 19 to 22 G and/or 22 to 28 G. The sheath may range between 1 to 3 G less than the needle. Optionally for a PEG stoma a needle and/or sheath may range between 80 to 100 mm in length and/or between 30 to 80 mm and/or between 100 to 130 mm.

In some embodiments, an endoscope is used to see a marker from inside the living organism. For example in FIG. 56B an endoscope 5619 is used to see that a marker is just protruding through in inside wall of a lumen. The distance between guide 5608b and the graduation is the length of the stoma formed through tissue 5620.

According to some exemplary embodiments, as shown in FIG. 56C each measurement segment of measuring device 5603, for example measurements segments 5632 and 5634 have a different distinctive color. In some embodiments, the distinctive color allows, for example to clearly visualize the measurement segment color using a visualization device placed in the stomach. Alternatively, each measurement segment has a distinctive pattern and/or shape and/or texture, for example to allow differentiation between the measurement segments. In some embodiments, a dividing zone 5636 is positioned between the measurement segments to allow, for example a better separation between adjacent segments. In some embodiments, the dividing zone is a gap between adjacent measurement segments. Alternatively the dividing zone has a visibly distinctive pattern and/or shape and/or color to indicate a separation region between the adjacent measurement segments.

In some embodiments, the width of each measurement segment is between 2 millimeters to 12 millimeters, for example between 2-6 millimeters or between 5-8 millimeters.

In some embodiments, the measuring device 5603, in inserted through the stoma until measuring point 5630 is attached to the outer surface of the skin.

In some embodiments, visualizing the measurement segments, allows to match an ostomy device with a length that matches the length indicated by the measurement segment.

In some embodiments, as explained above the, having wide measurement segments allows, for example to match ostomy device with a length that matches a range of measured lengths between the inner surface of the stomach lumen and the outer surface of the skin and not a specific length. In some embodiments, this allows for example to fix the ostomy device between the stomach lumen and the outer surface of the skin with a partial movement range to prevent stretching of the tissue or application of tension forces on the ostomy device after fixation.

Details of Flexible Resistant Outer Bolster

Figure 57A:
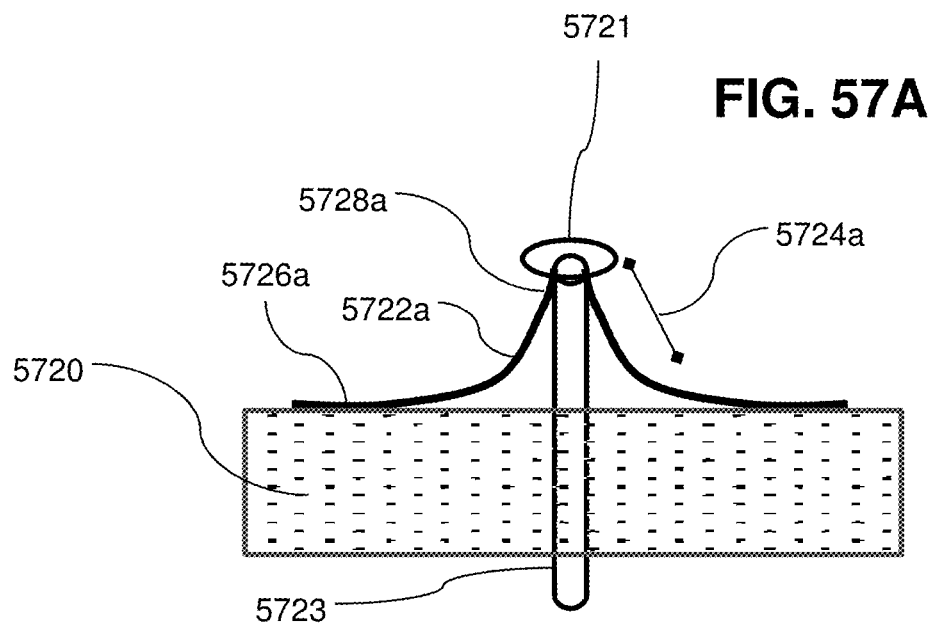
FIGS. 57A-57B are schematic views of elastic distancers in accordance with some embodiments of the current invention.
Figure 57B:
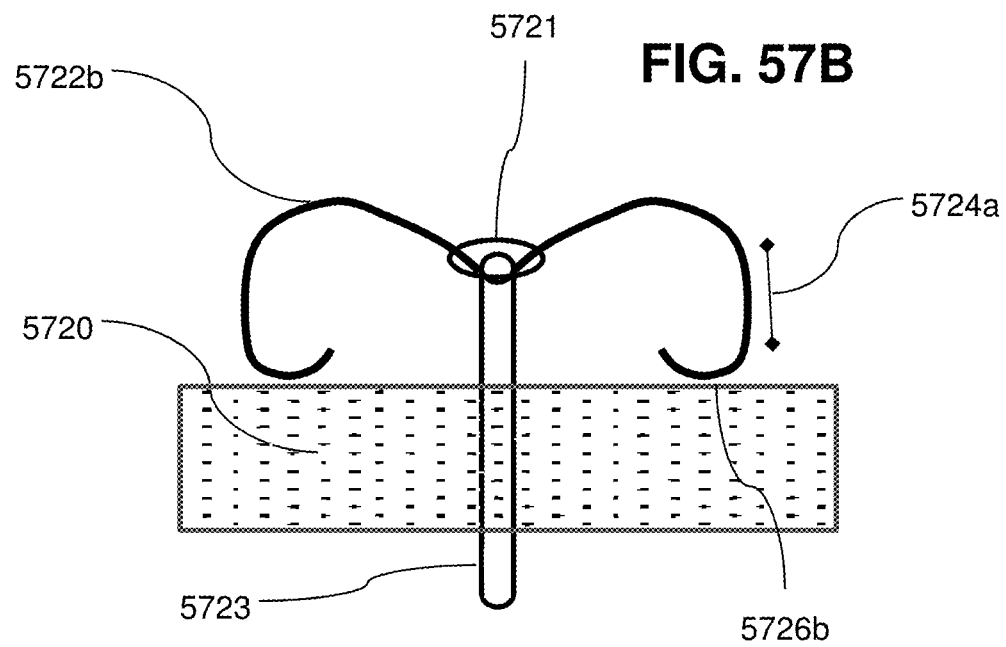

FIGS. 57A-57B are schematic views of elastic distances in accordance with some embodiments of the current invention. In some embodiments elastic distances are sized and shaped to provide even pressure between a bolster and tissue of a subject over significant axial and/or rotational displacements. Optionally, an elastic element may have a form that distributes stresses evenly along the element. For example, the distance may have the shape of a petal. The distancer is optionally curved. For example the distance may be concave towards a tissue interface and/or concave away from the tissue interface.

In some embodiments, three independent spacers may interact with tissue independently at contact interfaces distributed radially around a bolster. The elastic elements optionally leave a large portion of the area around the bolster open to allow air circulation. Alternatively or additionally he bolster may tilt optionally providing compensation for irregular swelling and/or twisting movements and the like. Alternatively or additionally there may be more or fewer than three spacers. For example in some cases a single elastic element may contact the tissue in locations distributed around the tube. Alternatively or additionally a rigid or flexible spacer may be connected to a flexible central bolster (for example the central bolster may be tiltable and/or move axially and/or it may be mounted to an elastic member such as a spring. Optionally the flexible central bolster and/or extender may compensate for tilting of the tube in respect to the tissue, regular or irregular swelling of the tissue and/or axial movement of the tube with respect to the tissue.

In some cases, movements of a person having a port opening to an internal tissue or lumen (e.g. a PEG) cause the position of the port to move with respect to the skin. Alternatively or additionally changes in the tissue (for example swelling) may cause displacements and tilting between the tissue of a subject and a PEG and/or a bolster. In some embodiments, an elastic spacer is designed to compensate for displacements and/or provide even interactive forces between the bolster and the skin. The compensation is optionally adjusted according to the shape, thickness and/or material properties of the flexible element. Optionally, the elastic element is shaped and sized to allow airflow around the stoma and/or to space the interface between the skin and the elastic element radially away from the stoma. Examples of elastic spacer elements in accordance with some embodiments are supplied for example by petals and/or extensions as described herein (for example in FIGS. 18A-18C, 28A-28D, 29A-29B, 30, 31A-31B, 51, 52, 53, 54, 57A and 57B).

FIGS. 57A-57B are schematic illustrations of a tube 5723 (e.g. a PEG tube) passing through tissue 5720 of a user and having an external bolster 5721 including elastic distancing elements 5722a and 5722b in accordance with an embodiment of the current invention. Optionally, elastic elements 5722a, 5722b are curved. For example, the curvature may distribute stresses evenly along the element. For example stresses may be caused by displacements of a tissue interface 5726a, 5726b with respect to bolster 5721 and/or tube 5723.

In some embodiments, elastic elements 5722a and/or 5722b have a significant portion 5724a and/or 5724b that is aligned to the axis of tube 5723. For example, an aligned portion may be oriented at an angle ranging between 0 to 10 degrees and/or between 10 to 30 degrees and/or 30 to 60 degrees to the axis of tube (e.g. tube 5723) at a connection (e.g. connection 5728a or 5728b) between the tube and the element. For example, an aligned portion may include between 10 to 30% and/or between 30% to 60% and/or between 60% to 100% of the elastic element. Optionally, axial displacements and/or tilting between tissue 5720 and tube 5723 may be absorbed as axial stress on aligned portion 5724a or 5724b.

In some embodiments, an elastic element (for example element 5722a) may be concave away from tissue 5720. Alternatively or additionally an elastic element (for example element 5722b) may be concave towards tissue 5720. Alternatively or additionally a elastic element may be wavy and/or angled for example with some sections concave upwards and/or downward and/or undefined concavity.

In some embodiments, a surface of flexible element (e.g. element 5722a or 5722b) may make a non-right angle with an axis of a tube (e.g. 5721) at a connection (for example connection 5728a or 5728b). For example, the angle between the flexible element and the axis of the tube at the connection may range between 0 to 20 degrees and/or between 20 to 45 degrees and/or between 45 to 70 degrees and/or between 70 to 80 degrees. For example the angle between the flexible element and a mean outer surface of tissue 5720 at the insertion location may range between 10 to 20 degrees and/or between 20 to 45 degrees and/or between 45 to 70 degrees and/or between 70 to 90 degrees.

In some embodiments, a flexible element may be curved. Optionally, a curved element may distribute stress and/or strain more evenly than a straight and/or horizontal element (for example similarly to an arch that may distribute stress more evenly than a horizontal lintel). For example a path between two points along a curved element may be longer than a straight line path between the points. For example, a distance along element 5722a between connection 5728a and interface 5726a is longer than a straight line between connection 5728a and interface 5726a. For example, a distance along element 5722b between connection 5728b and interface 5726b is longer than a straight line between connection 5728b and interface 5726b. For example, the path along a flexible element between the interface and a connector to a tube and/or a bolster may range between 10% to 15% and/or between 15% to 25% and/or between 25% to 50% and/or between 50% to 100% and/or greater than 100% longer than a straight line path between the connection and the interface. In some embodiments, distributing the stress along a longer element may allow an element to compensate for larger displacements (for example like a coil spring). Distributing the stress may allow the elastic element to compensate for larger displacements without buckling.

In some embodiments a flexible element may have an even thickness. For example an elastic element may be long and slender and/or flat and thin. Alternatively or additionally, the flexible element may be thickened a certain locations. For example, the element may become thicker where there is higher strain. For example, the elastic element may be thicker at a joints and/or a bend. Optionally, the elastic element may be thicker near the connection between the elastic element and the tube (for example element 5722a may be thicker near connection 5728a and/or element 5722b may be thicker near connection 5728b). Optionally an elastic element may become thinner as it spreads radially away from the tube.

In some embodiments an elastic element (e.g. element 5722a and/or 5722b) may be made of silicon. For example an elastic element thickness (for example the maximum thickness, minimum thickness and/or mean thickness) may range between 1 to 3 mm and/or between 0 to 1 mm and/or between 3 to 6 mm and/or between 6 to 10 mm. For example, an element having a stiff skeleton (for example a skeleton of metal optionally including spring steel and/or nitinol) may be thinner for example a silicon element may fit towards the middle of the spectrum for example a foam element may be towards the thick end of the spectrum and/or thicker.

In some embodiments a significant portion of the surface of tissue in a circular area around tube between the tube and an interface area with the tissue (for example in a circular area around tube 5723 between tube 5723 and interface area 5726a and/or 5726b) may be exposed to air and/or may not be covered by spacers. For example, the area exposed and/or uncovered area may range between 5 to 10% of the area of the circular region and or between 10 to 20% and/or between 20 to 40% and/or between 40 to 70%.

Figure 58A:
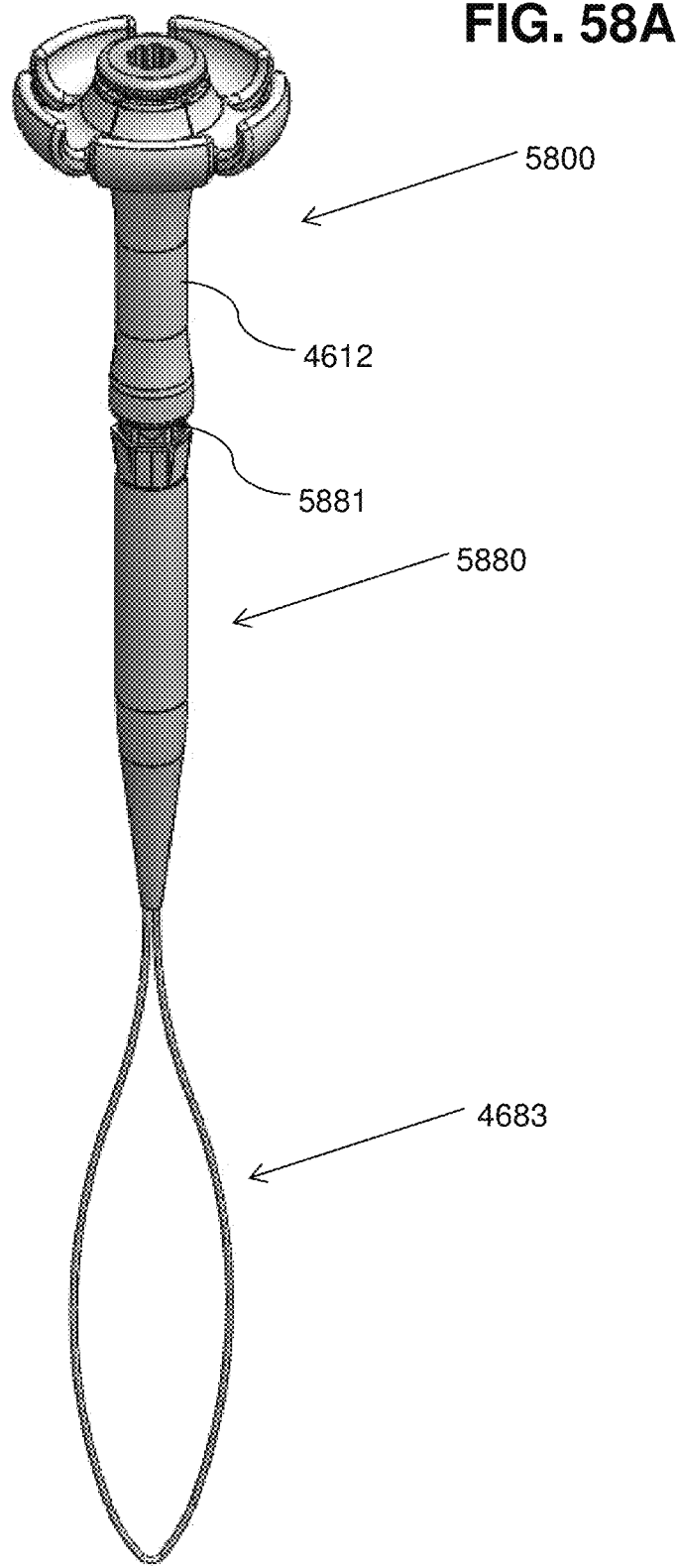
FIGS. 58A-58B are perspective views of a pushing device in accordance with some embodiments of the current invention.
Figure 58B:
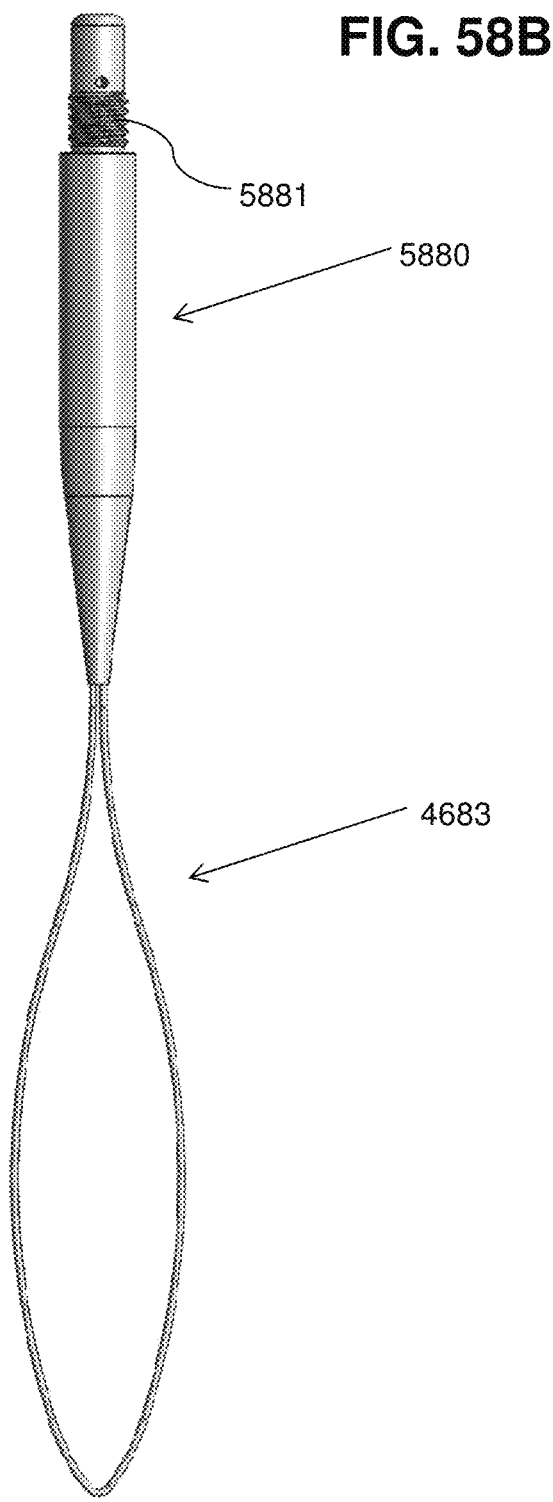

FIGS. 58A-58B are perspective views of a pushing device in accordance with some embodiments of the current invention. For example a dilator 5880 is connected to an ostomy device 5800 by a connector, for example a screw thread 5881. Optionally screw thread 5881 attaches to a proximal portion of device 5800. No rigid parts (for example no part of dilator is inserted into the middle and distal end of tube 4612. Tube 4612 and/or the distal portion of device 5800 are optionally flexible making them more easily inserted through the mouth, trachea etc. to the stomach or intestines. The less of dilator 5880 is inside tube 4612, the more flexible is tube 4612 and the easier it may be to insert tube 4612 into the lumen. For example when dilator 5880 is connected to device 5800, dilator 5880 may be inserted through less than $\frac{1}{10}$ of tube 4612 and/or between $\frac{1}{10}$ to $\frac{1}{5}$ and/or between $\frac{1}{5}$ to $\frac{1}{2}$ and/or between $\frac{1}{2}$ to $\frac{3}{5}$. Optionally thread 5881 on dilator 5880 is an external thread which connects to an internal thread on device 5800.

A Disassembly Tool

Figure 59A:
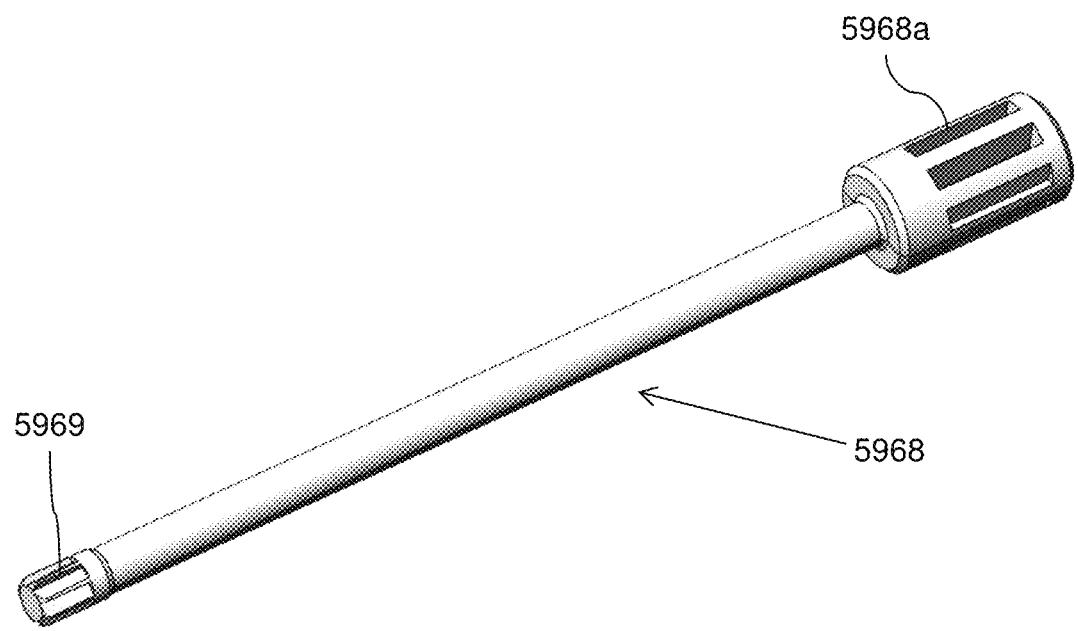
FIGS. 59A-59C are perspective views of a disassembly tool 5968 and socket in accordance with some embodiments of the current invention.
Figure 59B:
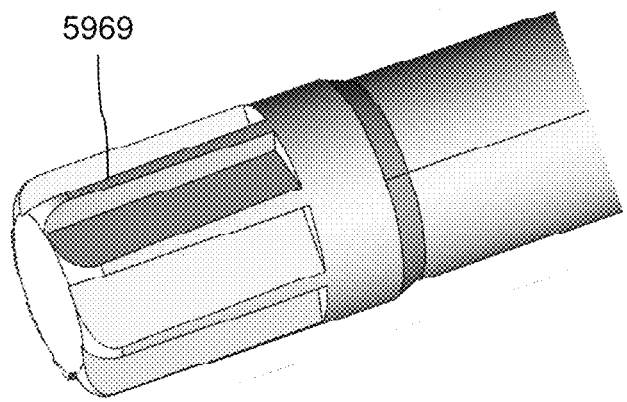
Figure 59C:
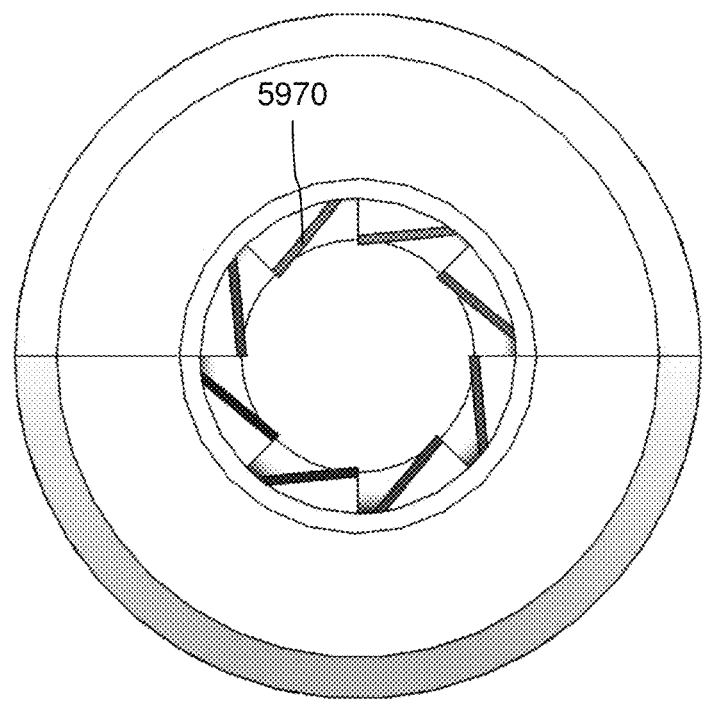

FIGS. 59A-59C are perspective views of a disassembly tool 5968 and socket in accordance with some embodiments of the current invention. The form of tool 5968 is optionally a wrench head 5969 on a long rod. The teeth of wrench head 5969 are optionally inclined (for example like a ratchet) such that wrench head can be used to turn socket 5970 in one direction only. For example, this facilitates disassembly, but avoids erroneously tightening the inner bolster making it harder to remove. Socket 5970 is fit on an inner lip and/or ledge of an ostomy device. The inner lip is small enough to avoid blocking flow and large enough to ensure good grip. Optionally the ledge may not completely surround the lumen of the ostomy device thereby allowing good grip for disassembly but also allowing an inner tube to pass by the lip while still contacting the inner walls of the ostomy device lumen at least in some places.

An Anti Rotational Bolster Connector

Figure 60:
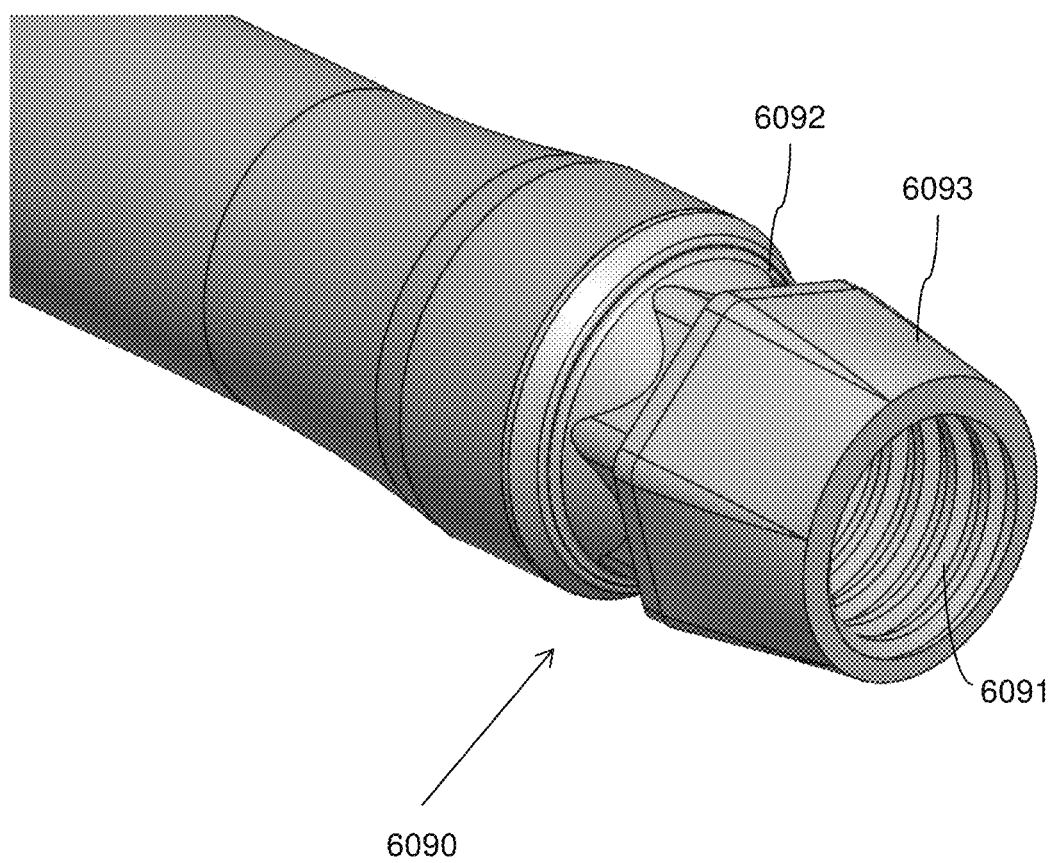
FIG. 60 is a perspective view of an anti rotational connector for an outer bolster to a tube in accordance with some embodiments of the current invention.

FIG. 60 is a perspective view of an anti rotational connector 6090 for an outer bolster to a tube in accordance with some embodiments of the current invention. For example the connector has an internal screw thread 6091 (for example for connecting to a dilator during insertion tool, an interference element (e.g. a ledge 6092) for connecting to a plastic snap connector on the outer bolster and/or a self aligning beveled non-slip head (for example a beveled hex head 6093 for preventing rotation of the bolster with respect to the tube.

Exemplary Ostomy Device with a Flared Tube

Figure 61B:
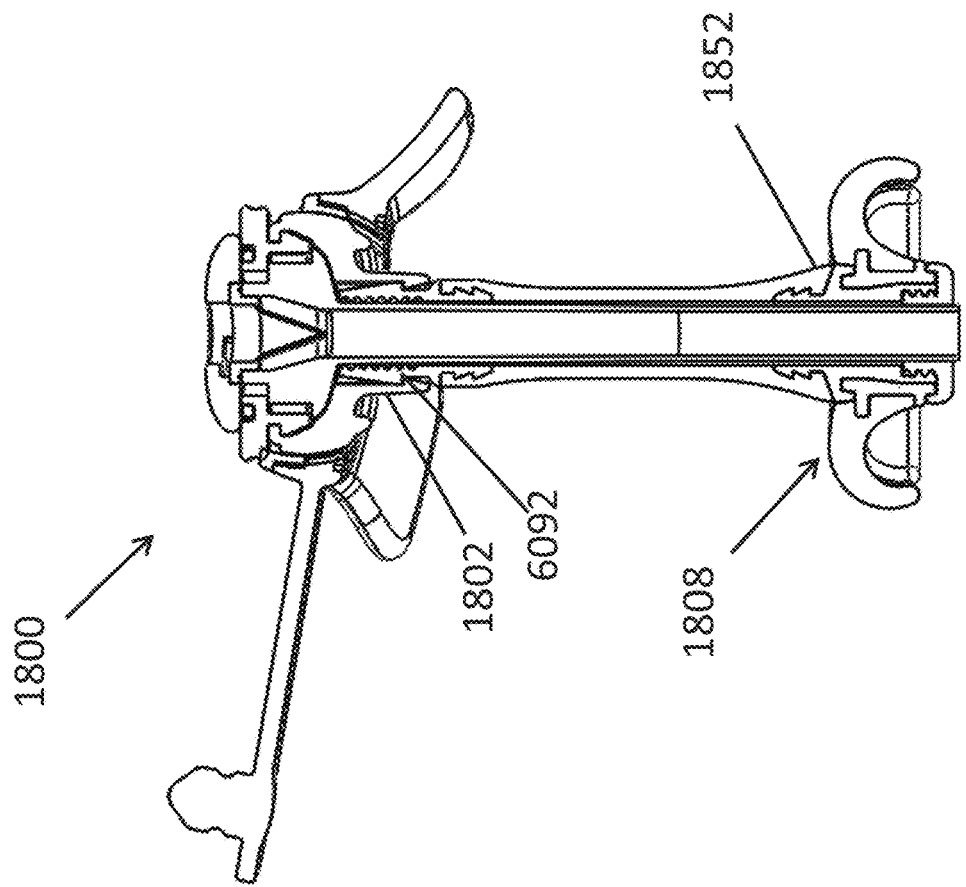
FIGS. 61A and 61B are schematic views of an ostomy device with an outer tube having a flared internal section in accordance with some embodiments of the current invention.
Figure 61A:
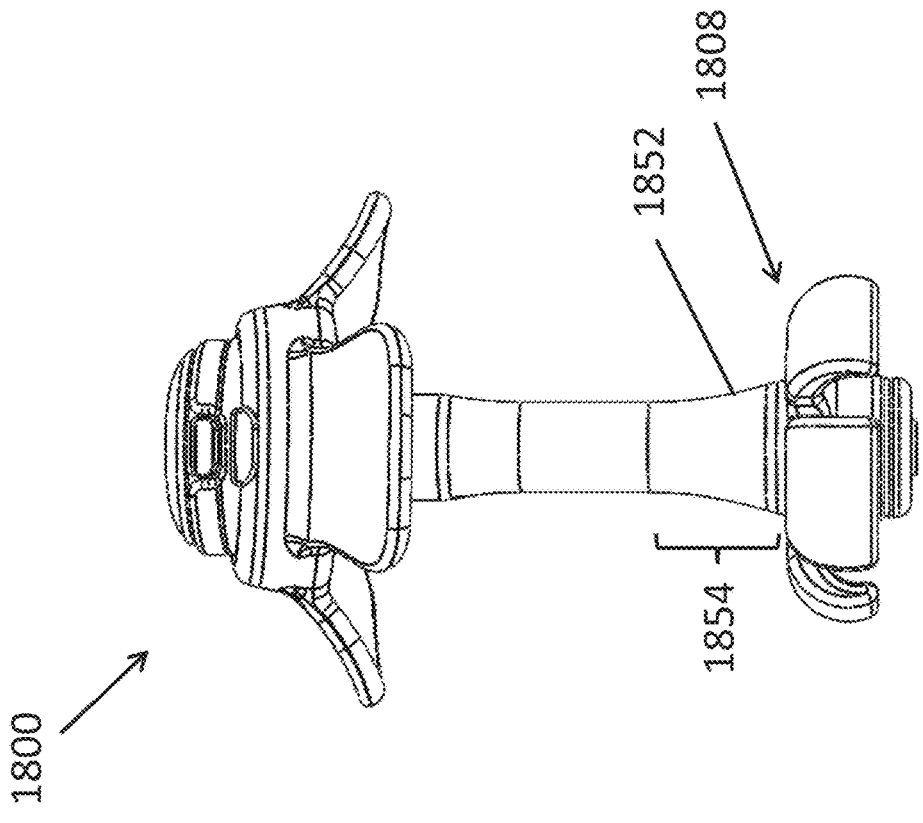

Reference is now made to FIGS. 61A and 61B depicting a simplified isometric view of an ostomy device having a flared outer tube, according to some embodiments of the invention.

According to some exemplary embodiments, an ostomy device, for example ostomy device 1800 comprises flared outer tube 1852 with a larger diameter at the distal end 1854, placed inside the stomach. In some embodiments, the flared outer tube positioned at least partially within the body allows, for example to minimize the possibility of the flared tube to be pulled outside from the body by having a tube ending inside the stomach lumen that is wider than the stoma. In some embodiments, the diameter of the tube ending within the stomach is at least 4% larger than stoma diameter, for example 5%, 10%, 15% larger.

Exemplary Inner Bolster of an Ostomy Device

Figures 62A, 62B, 62C:
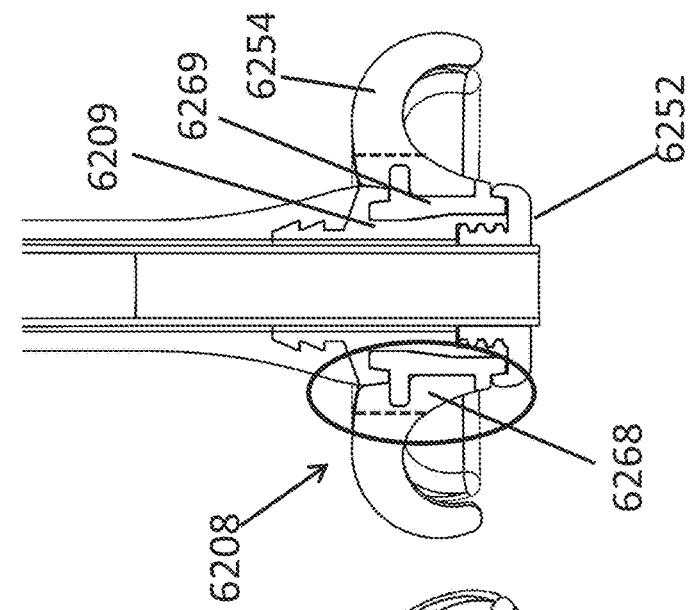
FIGS. 62A-62C are schematic views of an internal bolster in accordance with some embodiments of the current invention.

Reference is now made to FIGS. 62A-62C depicting an internal bolster with at least partly rigid shaft, according to some embodiments of the invention.

According to some exemplary embodiments, internal bolster 6208 comprises petals 6254 that are placed in contact with an internal bolster shaft 6266, optionally by cap 6252. In some embodiments, the internal bolster shaft 6266 is a rigid shaft. In some embodiments, the internal bolster shaft 6266 hardness level is at least 40 shore A, for example 50 shore A, 60 shore A or 70 shore A. In some embodiments, a partly rigid internal bolster shaft allows, for example to push the internal bolster out from the body with minimal damage to the body tissues. According to some exemplary embodiments, when attached to internal bolster shaft 6266, petals 6254 are spaced apart from each other. In some embodiments, the spacing between adjacent petals allows, for example each petal to apply minimal or no pressure on adjacent petals when the petals are in a collapsed and/or in a relaxed state. In some embodiments, each petal of petals 6254 comprises an at least partly rigid section 6268 at the attachment point of the petal to the internal bolster shaft. In some embodiments, the rigidity of section 6268 is at least 5% rigidity, for example 10%, 15%, 20%, 25%, 30%, 40% rigidity. In some embodiments, the rigidity of section 6268 allows to limit the bending of petals 6254, for example to ensure that the internal bolster and petals will not be permanently collapsed when the internal bolster is pushed through the esophagus.

According to some exemplary embodiments, rib 6265 is positioned between each adjacent petals of petals 6254, when they are connected to the internal bolster 6208. In some embodiments, the rib 6265 is shaped and sized to at least partially reduce application of forces, for example friction forces or torque forces applied by the petals on cap 6252, for example when the petals bend or twist.

According to some exemplary embodiments, each petal of petals 6254 comprises at least a partially rigid section 6269. In some embodiments, the section 6269 is connected to the external bolster 6208 between grooves in cap 6252 and grooves in connecting section 6209 of the internal bolster. In some embodiments, when cap 6252 is released, each petal of petals 6254 are release from the connecting section 6209 and the internal bolster 6208.

Exemplary Inner Tube Portion

Reference is now made to FIGS. 63A-63D depicting an inner tube portion of an ostomy device, according to some embodiments of the invention.

According to some exemplary embodiments, an inner tube portion, for example inner tube portion 6316 comprises an inner tube upper segment 6321 connected to the proximal section 6330 of an inner tube 6314. In some embodiments, a ring 6324 is connected to the inner tube cap 6322. In some embodiments, ring 6324 comprises buttons 6332, on the circumference of ring 6324. Optionally, the buttons 6332 are extending out from the circumference of ring 6324. In some embodiments the buttons 6332 are elastic buttons or springy buttons. In some embodiments, when the buttons are bend or pressed, ring 6324 is twisted and the inner tube portion is deflected from the outer tube of the ostomy device. In some embodiments, the buttons 6332 are shaped and sized to be placed within gaps 6326 in the circumference of the inner tube upper segment 6321. In some embodiments, an inner tube cap 6322, having an opening 6334 is placed on top of the inner tube section.

In some embodiments, a valve, for example a duckbill valve 6320 is positioned within ring 6324. In some embodiments, duckbill valve 6320 is configured to allow food to be inserted into the inner tube 6314 and into the stomach lumen, and prevents food to leak outside from the inner tube. In some embodiments, the duckbill valve is positioned between the inner tube of a low-profile ostomy device and an external feeding tube that can be attached and detached from the low-profile ostomy device. In some embodiments, a low-profile ostomy device is an ostomy device that protrudes 10 centimeters at most from the outer surface of the skin, for example 2, 4, 6 centimeters.

In some embodiments, an outer tube of an ostomy device comprises a valve, for example a duckbill valve. In some embodiments, the duckbill valve of the outer tube prevents food to leak out from the outer tube, for example to prevent leakage of food out from the stomach when inner tube is not in place.

Exemplary External Bolster

Reference is now made to FIGS. 64A-64E, depicting an external bolster of an ostomy device, according to some embodiments of the invention.

According to some exemplary embodiments, external bolster 6450 is placed inside an external petals ring 6452 which comprises external petals 6499 around the circumference of the rigid ring. In some embodiments, external bolster 6450 comprises at least one protruding section 6458 extending out from the circumference of the external bolster. In some embodiments, protruding section 6458 of the external bolster 6450 have an outer surface, shaped and sized to increase friction between the external bolster 6450 and external petals ring 6452. In some embodiments, increasing the friction between protruding sections 6458 and the external petals ring 6452 allows for example, the rotation of the external bolster and the ostomy device when rotating the petals ring 6452. In some embodiments, the friction between protruding sections 6458 and the external petals ring 6452 prevents, for example a relative rotation of the external petals ring 6452 in relation to the external bolster and/or the ostomy device.

In some embodiments, a cap 6454 is connected to the rigid ring 6452 via an elastic strap 6456. Optionally cap 6454 is shaped to fit and close opening 6334 shown in FIG. 63D when an external feeding tube is not connected.

According to some exemplary embodiments, external bolster 6450 comprises openings 6460 at the top circumference. In some embodiments, openings 6460 are shaped and sized to allow, for example the attachment and locking of elastic buttons 6332 of the inner tube portion 6316 shown in FIG. 63C. In some embodiments, the position of openings 6460 allows for example, to direct the insertion of the elastic buttons 6332, optionally to a desired position. In some embodiments, each of the openings 6460 have a different geometrical shape that match at least one specific elastic button of elastic buttons 6332, to allow for example a specific orientation connection between the elastic buttons 6332 and openings 6460.

According to some exemplary embodiments, for example as shown in FIG. 64E, the inner circumference of the external bolster has a geometrical shape that allow, for example to prevent the rotation of the outer tube connected to the external bolster. In some embodiments, the inner circumference 6462 of the external bolster 6450 is shaped as a polygon, for example as a hexagon. In some embodiments, the inner circumference of the external bolster has a matching geometrical shape to the anti-rotation connector of the outer tube, for example the anti-rotation connector 6090. In some embodiments, when connecting the external bolster to the anti-rotation connector, a snap connector of the external bolster, for example snap connector 1802 shown in FIG. 61B snaps underneath ledge 6092, shown in FIGS. 61B and 60. The interconnection between snap connector 1802 and ledge 6092 prevents the release of the external bolster from the outer tube.

In some exemplary embodiments of the invention, the anti-rotation connector includes an inclined portion which is also shaped, to match the geometry of the external bolster inner circumference 6462, so as to orientationally guide the bolster to be aligned with the interconnection. Optionally, the matching geometries are polygonal, optionally with rotational symmetry.

Exemplary High-Profile Ostomy Device

Reference is now made to FIGS. 65A and 65B, depicting a high-profile ostomy device, according to some embodiments of the invention. In some embodiments a high-profile ostomy device is an ostomy device that protrudes at least 10 centimeters from the outer surface of the body, for example 20 centimeters, 30 centimeters, or intermediate or greater protrusions. In some embodiments, a high-profile ostomy device is an ostomy device where the connector to the feeding element is located on the distal of a tube protruding out of the ostomy device or the external bolster.

According to some exemplary embodiments, a feeding tube is connected to an ostomy device 6510. In some embodiments, the feeding tube is connected to ostomy device 6510 by an irreversible locking mechanism. In some embodiments, to disconnect the feeding tube 6512 from the ostomy device 6510, elastic sections of a snap-fit locking mechanism between the inner tube portion and the external bolster are pressed and the feeding tube 6512 is released together with the inner tube portion 6520 from the ostomy device 6510.

According to some exemplary embodiments, the connection between an external feeding tube to the ostomy device is weaker than the connection of the ostomy device to the body. In some embodiments, the connection of the elastic buttons 6332 of the inner tube portion to the external bolster of the ostomy device is weaker than the connection between the feeding tube and the inner tube portion. In some embodiments, the weaker connection between the inner tube portion and the external bolster acts for example, as a safety mechanism to allow the disconnection of the feeding tube and the inner tube portion before the ostomy device is pulled out from the ostomy opening in the abdomen. In some embodiments, the connector or the locking mechanism of the outer tube and the internal and/or external bolsters connects the outer tube to the bolster with a greater pull-out resistance force compared to the connector or the locking mechanism between the inner tube portion and the ostomy device.

Exemplary Kit for Direct Stomach Feeding

According to some exemplary embodiments, a kit for direct stomach feeding comprises an ostomy device and an external feeding tube. In some embodiments, the ostomy device comprises a tube and an internal and/or external bolsters for fixing the tube between a stomach lumen and the outer surface of the skin. In some embodiments, the kit comprises an inner tube, configured to be place within the tube. In some embodiments, the external feeding tube is connected to the external bolster or to the outer tube or to the inner tube.

Exemplary Device for Small Intestine Feeding or Stomach Decompression

Reference is now made to FIGS. 65C-65G depicting an ostomy device with an elongated inner tube for small intestine feeding and/or for stomach decompression, according to some embodiments of the invention.

Figure 65E:
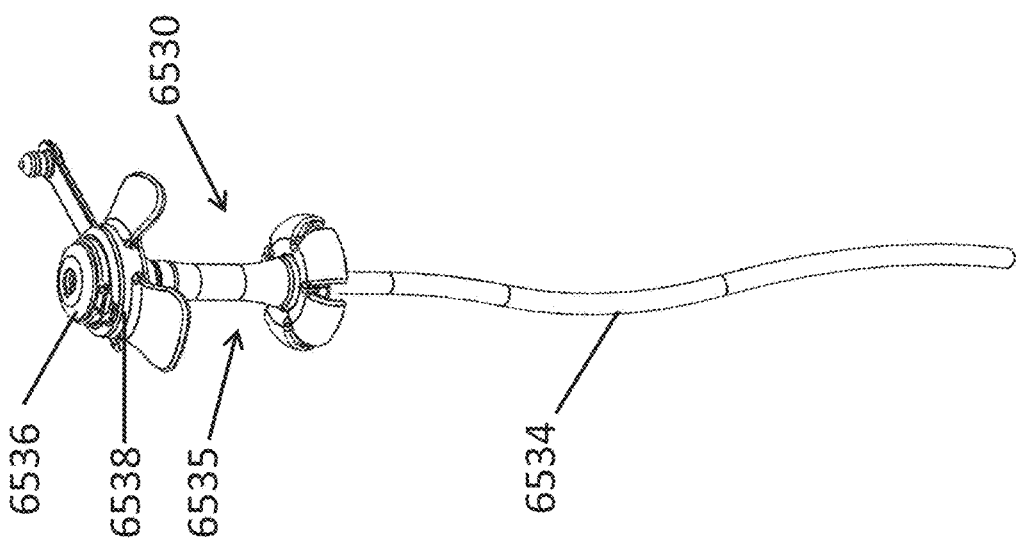
FIGS. 65C-65E are schematic views of an ostomy device with an elongated inner tube in accordance with some embodiments of the current invention.
Figure 65D:
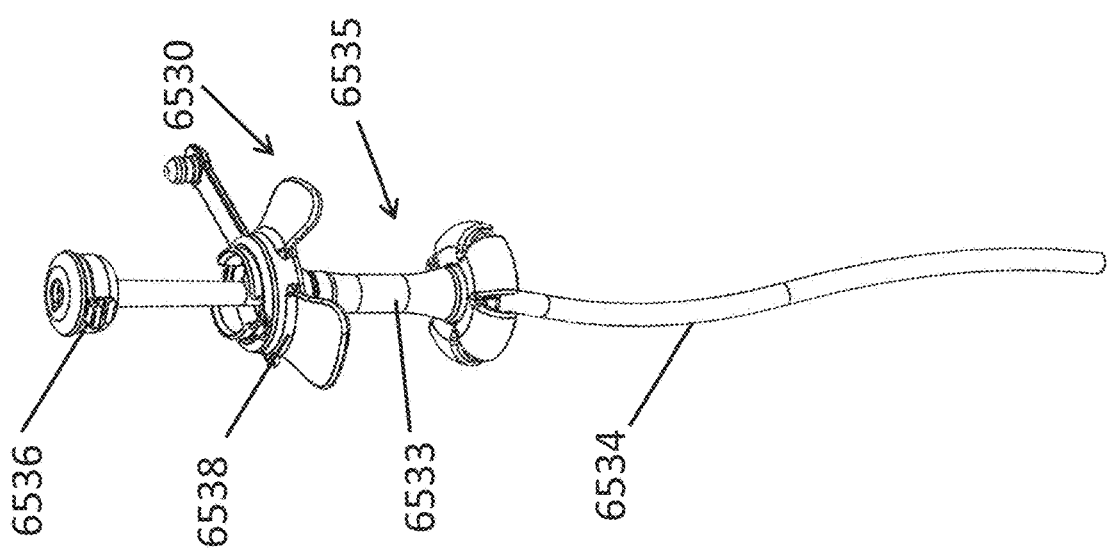
Figure 65C:
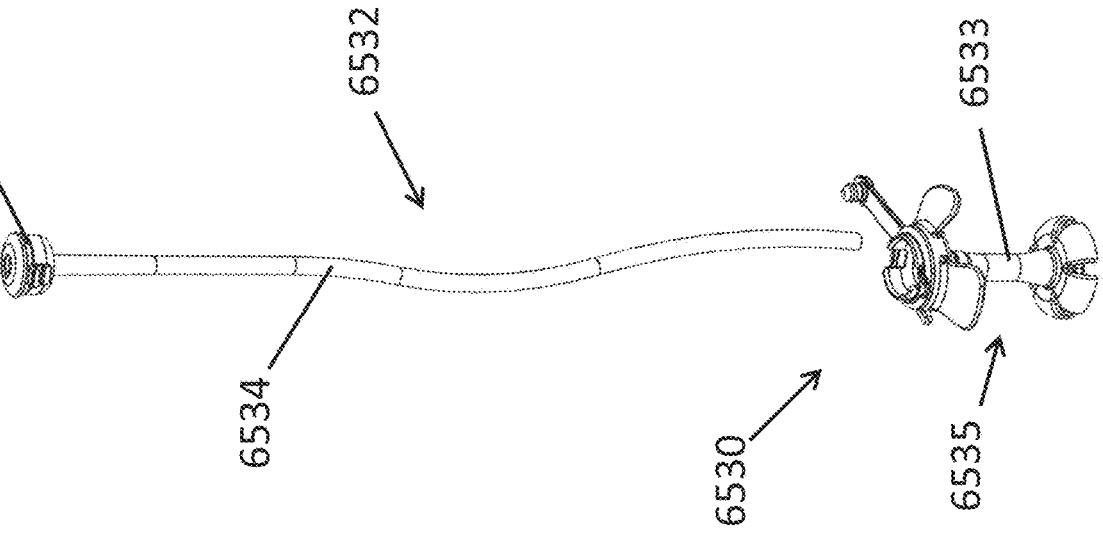
Figure 65F:
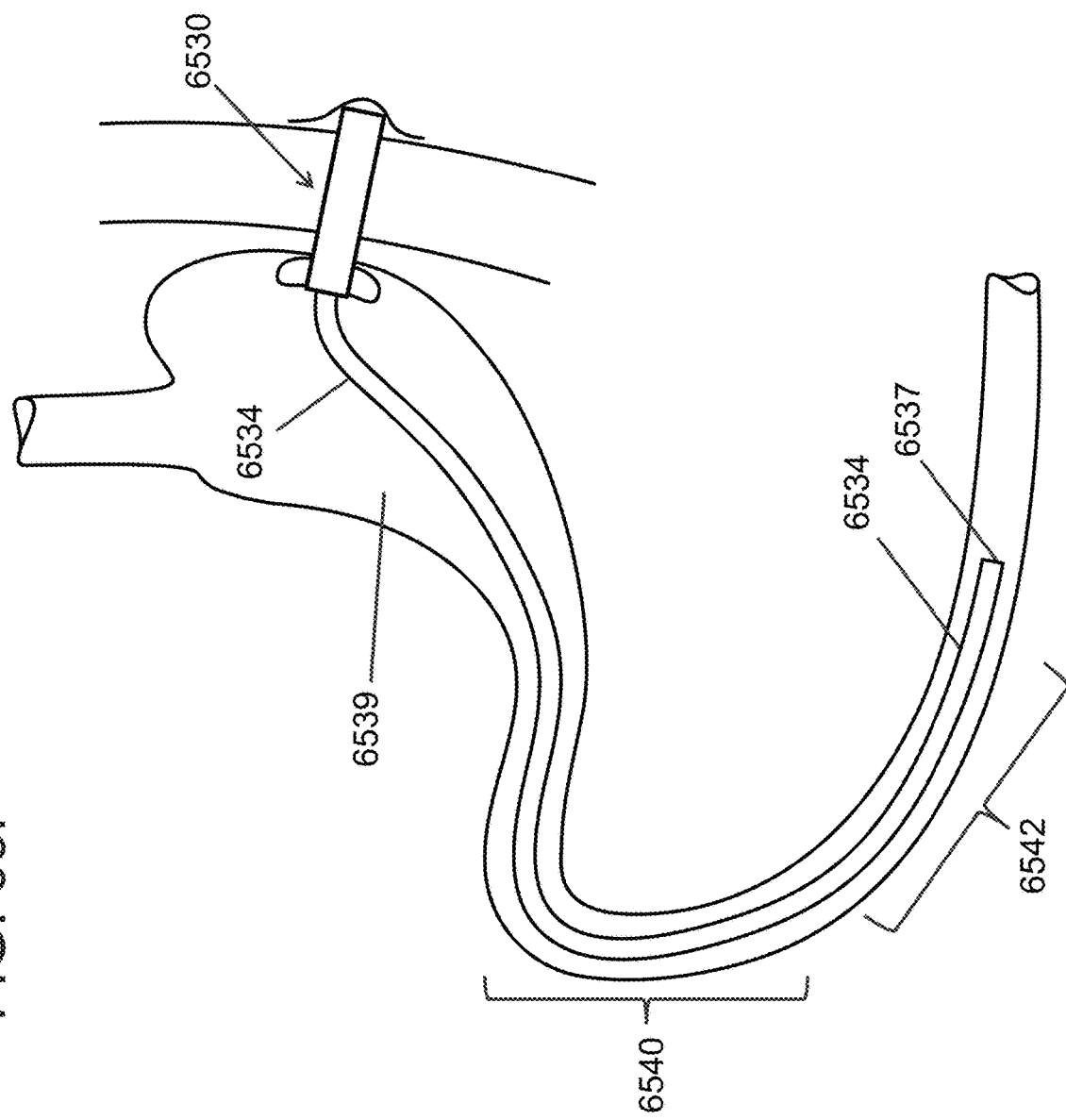
FIG. 65F is a schematic illustration of an ostomy device with an elongated inner tube extending into the small intestine in accordance with some embodiments of the invention.

According to some exemplary embodiments, ostomy device comprises an inner tube portion 6532 having an elongated inner tube 6534 and an external tube portion 6536. In some embodiments, the inner tube portion 6532 is pushed through the outer tube 6533, until the inner tube portion 6532 extends out from the outer tube 6533, for example as shown in FIG. 65D. In some embodiments, the inner tube portion is pushed until an inner tube cap 6536 is locked within an external bolster 6538, for example as shown in FIG. 65E. In some embodiments, the length of the elongated inner tube is at least 5 centimeters, for example 5, 10, 15, 30, centimeters.

According to some exemplary embodiments, the inner tube 6534 of the ostomy device 6530 is shaped and sized to extend from stomach 6539 into the small intestine. In some embodiments, the inner tube 6534 is placed within the small intestine, with the inner tube end 6537 is positioned in the jejunum 6542 or in the duodenum 6540. In some embodiments, placing the end of the inner tube within the small intestine allows, for example feeding directly into the small intestine, optionally bypassing the stomach.

Figure 65G:
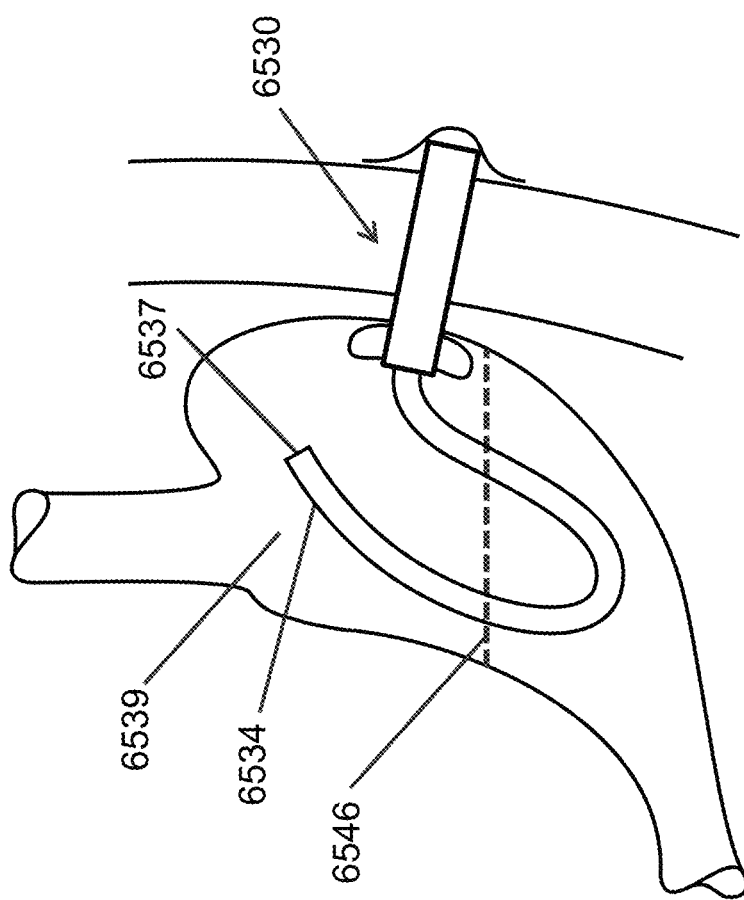
FIG. 65G is a schematic illustration of an ostomy device with an elongated inner tube ending positioned above the stomach content in accordance with some embodiments of the current invention.

According to some exemplary embodiments, the inner tube 6534 of the ostomy device, is positioned with the inner tube end 6537 inside the stomach. In some embodiments, the inner tube end 6537 is positioned above stomach content level 6546, for example as shown in FIG. 65G. In some embodiments, placing the inner tube end 6537 above the stomach content level allows, for example to decompress the stomach optionally by allowing gas to exit from the body through the ostomy device.

Exemplary Process of Stomach Content Aspiration

Figure 66A:
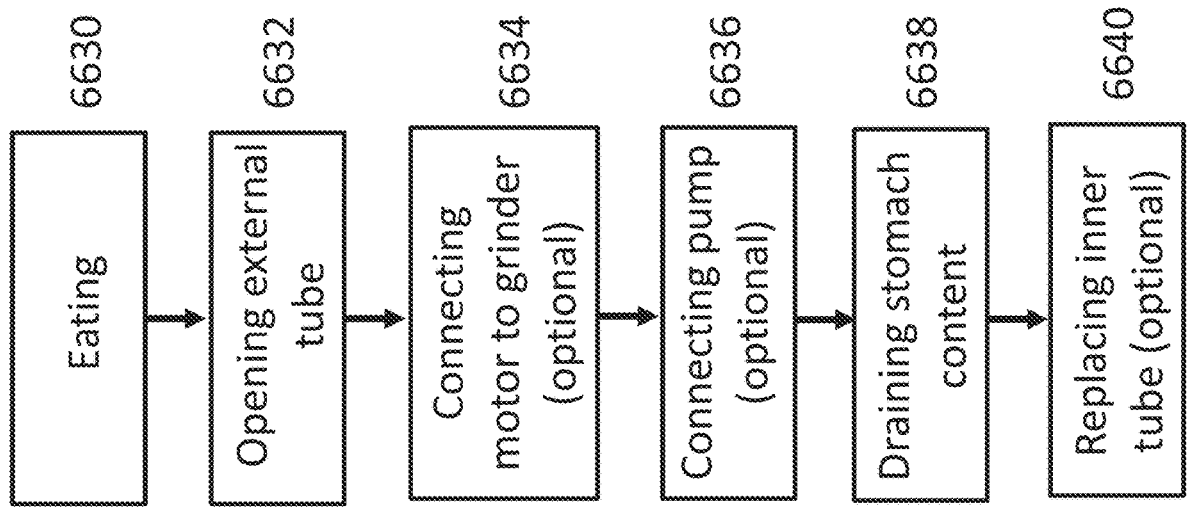
FIG. 66A is a flow chart of a process for draining the content of a stomach in accordance with some embodiments of the current invention.

Reference is now made to FIG. 66A depicting a process of stomach content aspiration, according to some embodiments of the invention.

According to some exemplary embodiments, a subject is eating at 6630. In some embodiments, after the subject finishes eating, the external end of an ostomy device is opened at 6632. In some embodiments, the external end of the ostomy device is opened during eating. In some embodiments, the external tube of an ostomy device is opened at 6632. In some embodiments, the external tube is opened after a pre-determined time from the eating. In some embodiments, the pre-determined time is adjusted according to the composition of food that the subject ate and/or according to nutritional parameters of the food. Optionally, the pre-determined time is adjusted according to the amount of food the subject ate.

According to some exemplary embodiments, a motor is connected to a grinder of the inner tube at 6634. In some embodiments, the motor activates the grinder, for example to grind the stomach content. In some embodiments, the motor activates the grinder for a pre-determined time period. In some embodiments, the grinding time period is adjusted according to the amount of food and/or according to the stomach content composition. Optionally, the grinding time is adjusted according to the time passed from the finishing of the eating at 6630. In some embodiments, the motor pumps out the stomach content.

According to some exemplary embodiments, a pump is connected to the inner tube at 6636, for example to allow pumping out the stomach content.

According to some exemplary embodiments, the stomach content is drained at 6638. In some embodiments, the stomach content is drained through the inner tube. Optionally the stomach content is drained through a draining tube connected to the inner tube. In some embodiments, the stomach content is drained into a waste reservoir connected to the draining tube. In some embodiments, the stomach content is drained until the desired amount and/or weight of content is drained out from the body.

According to some exemplary embodiments, the inner tube is replaced at 6640. In some embodiments, the inner tube is replaced, for example if food at least partly blocks the inner tube lumen.

Exemplary Stomach Content Aspiration Device

Figure 66B:
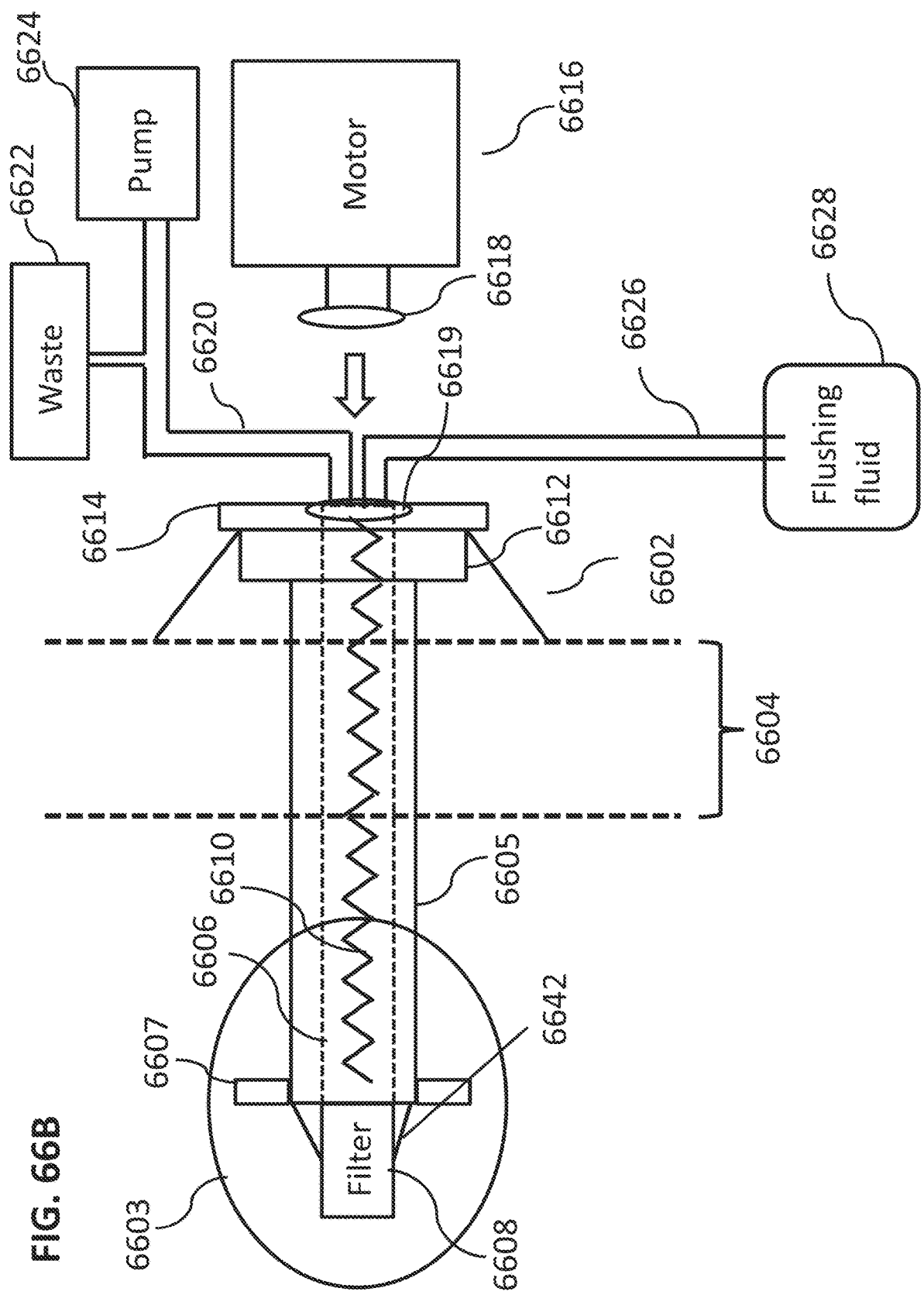
FIG. 66B is a block diagram of a device for draining the content of the stomach, in accordance with some embodiments of the current invention.
Figure 67C:
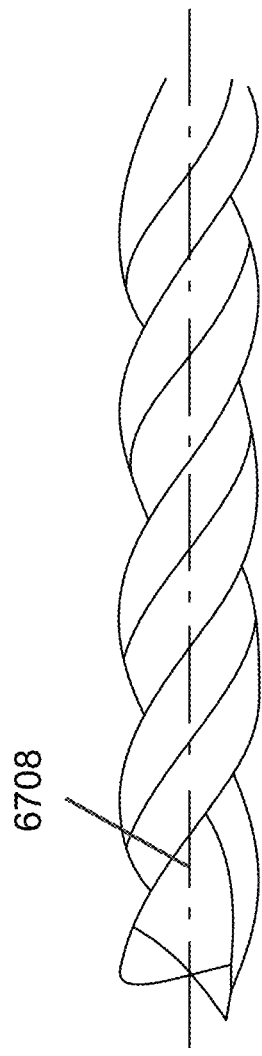
Figure 67D:
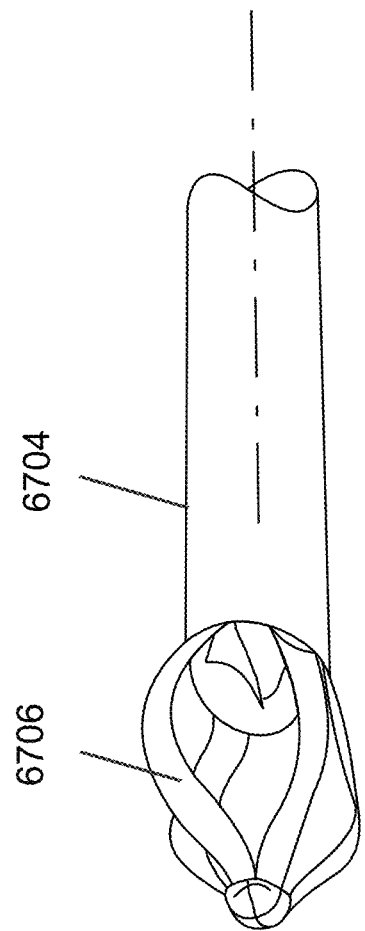

Reference is now made to FIG. 66B, depicting a stomach content draining device, according to some embodiments of the invention.

According to some exemplary embodiments, a stomach content draining device 6602 comprises an outer tube 6605 inserted through body wall 6604 into stomach 6603, and an inner tube 6606 positioned within the outer tube 6605. In some embodiments, the inner tube 6606 comprises a filter 6608, for example a basket connected to the distal end of the inner tube 6606 that is placed inside the stomach 6603. In some embodiments, the filter is at least partially permeable to food.

According to some exemplary embodiments, inner tube 6606 is at least 5% more rigid compared to the outer tube 6605, for example 10%, 20%, 30%, 50% more rigid. In some embodiments, inserting a rigid inner tube into a flexible outer tube stretches the outer tube.

According to some exemplary embodiments, the outer tube 6605 comprises an inner stomach valve 6642. In some embodiments, the inner stomach valve comprises a flat valve configured to prevent food from entry into the outer tube 6605 if inner tube 6606 is not present. In some embodiments, when inner tube 6606 is pushed through outer tube 6605, inner tube 6606 opens the valve towards the stomach lumen.

According to some exemplary embodiments, a grinder 6610 is positioned within the inner tube 6606. In some embodiments, upon activation the grinder grinds the content of the stomach and/or the content of the stomach that is found within the inner tube 6606. In some embodiments, the grinder 6610 is partly positioned outside of the inner tube 6606, for example to grind the content of the stomach. In some embodiments, the grinder part which extends into the stomach lumen is placed within filter 6608. Optionally, filter 6608 prevents direct contact of grinder 6610 with the stomach inner wall. In some embodiments, the grinder 6610 is a spiral shaft, optionally with sharp leading edges, for example to allow slicing of food within the inner tube.

According to some exemplary embodiments, the outer tube 6605 is connected to an internal bolster 6607 placed within the stomach 6603 and to an external bolster 6612 placed outside of the body.

According to some exemplary embodiments, inner tube 6606 is connected to an external connector 6614. In some embodiments, the external connector 6614 is configured to lock the inner tube 6606 within the outer tube 6605. In some embodiments, the external connector 6614 comprises a motor connector 6619. In some embodiments, the motor connector 6619 is coupled to the grinder 6610, for example to allow the rotation of the grinder 6610. In some embodiments, a motor 6616, for example an electric motor is connected through a motor adaptor 6618 to the motor connector 6619. In some embodiments, upon activation motor 6616 rotates the grinder 6610 optionally by rotating motor adaptor 6618 and/or motor connector 6619. In some embodiments, turning grinder 6610, for example by motor 6616 moves food out from the stomach.

According to some exemplary embodiments, a draining tube 6620 is connected to the inner tube, optionally through external connector 6614. In some embodiments, the stomach content is drained through the draining tube 6620 into waste reservoir 6622. Optionally a pump 6624, for example a peristaltic pump is connected to draining tube 6620. In some embodiments, the pump 6624 actively pumps the stomach content through the inner tube and the draining tube into waste reservoir 6622. In some embodiments, pump 6624 rotates grinder 6610.

According to some exemplary embodiments, flushing fluid 6628 is passed into the inner tube 6606, for example when parts of the stomach content are stuck within the inner tube. In some embodiments, the flushing fluid 6628 is passed through flushing tube 6626. Alternatively, flushing fluid is passed through draining tube 6620. In some embodiments, flushing fluid 6628 comprises enzymes and/or digestive chemicals, for example to allow digestion of food within the stomach and/or within the inner tube.

According to some exemplary embodiments, flushing tube 6626 and/or draining tube 6620 are connected to the inner tube 6606 through motor connector 6619 which allows, for example co-centric connection between motor connector 6619 and motor adaptor 6618. Alternatively, motor adaptor 6618 is connected to motor connector 6619 from an upper or a lower side while flushing tube 6626 and/or draining tube 6620 are connected directly to the center of tube 6606

According to some exemplary embodiments, grinder 6610 is placed within an inner tube, for example inner tube 6314, 1714 or 1814. In some embodiments, the inner tube is placed within an outer tube, for example outer tube 1812. In some embodiments, the outer tube is connected to an internal bolster of an ostomy device placed within the stomach, for example inner bolster 1808 and to an external bolster, for example external bolster 3110, or 5100.

Exemplary Stomach Content Draining Device within the Body

Reference is now made to FIG. 66C depicting a stomach content draining device within the body, according to some embodiments.

According to some exemplary embodiments, a draining device 6650 is inserted into the body wall 6604 into a stomach 6603. In some embodiments, the draining device 6650 comprises a tube 6652 with a grinder 6658 positioned within the tube. In some embodiments, a filter, for example basket 6654 is connected to the distal end of the tube 6652, and is positioned within the stomach 6603. In some embodiments, an internal bolster 6656 is connected to tube 6652 at the distal end of the tube 6652 within stomach 6603. Additionally, an external bolster 6655 is connected to tube 6652 at the proximal end outside of the body. In some embodiments, the internal bolster 6656 prevents pushing tube 6652 outside of the body. In some embodiments, the external bolster 6655 stabilizes the tube 6652 when the body moves and/or prevents the internalization of tube 6652 through the abdominal opening.

According to some exemplary embodiments, tube 6652 is placed within an outer tube. In some embodiments, the internal bolster 6656 and/or the external bolster 6655 are connected to the outer tube.

Exemplary Inner Tube with a Grinder

Reference is now made to FIGS. 67A-67D, depicting an inner tube and a grinder of a stomach content draining device, according to some embodiments of the invention.

According to some exemplary embodiments, inner tube 6704 comprising a distal end 6716 configured to be placed within a stomach and a proximal end 6720, configured to be placed outside of the body. In some embodiments, a filter, for example elastic basket 6706 is connected to the distal end 6716 of the inner tube 6704. In some embodiments, basket 6706 is configured to be in a collapsed state, for example when basket 6706 is moved through the outer tube into the stomach, and in a relaxed state when basket 6706 is pushed out from the inner tube 6704. In some embodiments, the basket comprises voids or openings that allow the basket, for example to collapse. Alternatively or additionally, the basket is made from an elastic material or an elastomer.

According to some exemplary embodiments, basket 6706 comprises is made from wires placed in a distance from one another, or from a mesh of wires. Optionally, the wires are elastic, for example to allow the collapse of the basket 6706. In some embodiments, the maximal distance between two adjacent wires, for example wires 6707 and 6709 determine the size of food particles that can enter into the inner tube 6704. Alternatively, the maximal size of the pores within the mesh of wires determine the size of the food that can enter the inner tube.

According to some exemplary embodiments, an external bolster, for example external bolster 6712 is connected to the proximal end 6720 of the inner tube 6704. Alternatively or additionally an inner tube cap 6710 is connected to proximal end 6720 of the inner tube 6704.

General

As used herein the term "about" refers to ±20%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural refers unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A measuring device for sizing a distance between an outer surface of a subject and a lumen in said subject, comprising:
   a. a needle configured to make a passageway from said outer surface to said lumen; said needle comprising an elongated body, a proximal end, a distal end comprising a retractable needle point, said needle having a length adapted to reach said lumen;
   b. a shoulder located on said proximal end of said elongated body of said needle;
   c. a plurality of markings located on said elongated body of said needle and configured to be seen from within said lumen.

2. The measuring device according to claim 1, wherein said plurality of markings are color coded markings.

3. The measuring device according to claim 1, further comprising a transparent and/or a translucent sheath sized to include said needle within.

4. The measuring device according to claim 1, wherein said needle is hollow.

5. The measuring device according to claim 1, wherein said markings are one or more of lines, symbols, changes in shape, protrusions, etched portions and indentations.

6. The measuring device according to claim 1, wherein said needle comprises a length in the range of from about 30 mm to about 130 mm.

7. The measuring device according to claim 1, wherein said passageway is large enough for insertion of one or more of: a loop of a pushing device, a pushing device, an outer tube of a feeding device and an outer tube of a PEG feeding device.

8. A method of measuring a distance between two ends of a passageway into a living tissue of a subject, comprising:
 a. inserting a measuring device, said measuring device comprising a needle, a shoulder on said needle and a plurality of markings on said needle, said inserting is at a location on an external surface so as to reach a lumen and until said shoulder meets said location on said external surface;
 b. visualizing from an inside of said lumen, at least one marking from said plurality of markings;
 c. assessing a distance between said at least one marking and said shoulder; and
 d. inserting a chosen tube comprising an internal bolster according to said measuring via a mouth of said subject into said lumen until a proximal end of said chosen tube exits an external end of said passageway.

9. The method according to claim 8, wherein said inserting generates said passageway.

10. The method according to claim 8, further comprising inserting a viewing device from an opening into said lumen to perform said visualizing.

11. The method according to claim 8, wherein previously to said inserting, the method further comprises, visualizing an inner surface of said lumen, selecting a target site for said inserting, and visualizing said target site on said external surface of said subject.

12. The method according to claim 8, wherein said assessing is performed without applying a force axially towards an external side, on the tissue of said lumen.

13. The method according to claim 8, wherein said measurement of said distance between two ends of a passageway is used as a safe length for installing a feeding device.

14. The method according to claim 8, wherein said visualizing is performed using an imaging technique.

15. The method according to claim 8, wherein said measuring device further comprises a sheath sized to include said needle within, and said plurality of markings are on said sheath.

16. The method according to claim 8, wherein said passageway is a pre-existing passageway.

17. The method according to claim 8, further comprising attaching an external bolster on said proximal end of said chosen tube.

18. A method of installing a feeding device in a passageway in a living tissue of a subject, the method comprising:
 a. measuring a distance between two ends of a passageway and inserting a chosen tube into said lumen according to the method of claim 8, wherein said chosen tube comprises an adaptor on its proximal end;
 b. attaching an external bolster on said adaptor in said proximal end of said tube.

* * * * *